US012635992B2

(12) United States Patent　　(10) Patent No.:　US 12,635,992 B2
Lonky　　　　　　　　　　　　　　　(45) Date of Patent:　May 26, 2026

(54) SCRAPE AND SWEEP FRICTIONAL TISSUE SAMPLING AND COLLECTION METHOD AND DEVICE

(71) Applicant: Histologics LLC, Anaheim, CA (US)

(72) Inventor: Neal Marc Lonky, Yorba Linda, CA (US)

(73) Assignee: HISTOLOGICS LLC, Anaheim, CA (US)

( * ) Notice: Subject to any disclaimer, the term of this patent is extended or adjusted under 35 U.S.C. 154(b) by 223 days.

(21) Appl. No.: 18/109,630

(22) Filed: Feb. 14, 2023

(65) Prior Publication Data

US 2023/0210505 A1　　Jul. 6, 2023

Related U.S. Application Data

(63) Continuation-in-part of application No. 16/573,920, filed on Sep. 17, 2019, now abandoned.

(Continued)

(51) Int. Cl.
*A61B 10/02*　　　(2006.01)
(52) U.S. Cl.
CPC ...... *A61B 10/02* (2013.01); *A61B 2010/0216* (2013.01)
(58) Field of Classification Search
CPC ........ A61B 2010/0216; A61B 10/0291; A61B 2017/320008; A61B 2017/320012; A61B 2017/320004
See application file for complete search history.

(56) References Cited

U.S. PATENT DOCUMENTS 1,795,500 A　　3/1931　Omundson
2,675,572 A　　4/1954　Nomiya
(Continued)

FOREIGN PATENT DOCUMENTS

AT　　　392411　　5/1988
CH　　　653880　　1/1986
(Continued)

OTHER PUBLICATIONS

Blute, Renal brush biopsy: Survey of indications, techniques and results, J Urol., Aug. 1981, vol. 126(2), pp. 146-149.
(Continued)

*Primary Examiner* — Jennifer Robertson
*Assistant Examiner* — H.Q. Nguyen
(74) *Attorney, Agent, or Firm* — SCI-LAW STRATEGIES, PC

(57)　　　　　　ABSTRACT
In an embodiment of the invention, a frictional tissue sampling device for obtaining a histological sample from an epithelial layer includes a platform with an axis, an abrasive material comprising a plurality of fibers associated with the platform, where the abrasive material is adapted to abrade the epithelial layer to dislodge the histological sample, where rotation of the platform around the axis rotates the abrasive material, and a collector material comprising a plurality of loops associated with the platform, where rotation of the platform around the axis rotates the collector material, where the collector material is adapted to collect the histological sample dislodged by the abrasive material, where contacting the platform with the epithelial layer and rotation of the platform moves the abrasive material and the collector material over the epithelial layer thereby obtaining the sample.

10 Claims, 31 Drawing Sheets

Related U.S. Application Data

(60) Provisional application No. 62/840,354, filed on Apr. 29, 2019, provisional application No. 62/782,178, filed on Dec. 19, 2018, provisional application No. 62/733,933, filed on Sep. 20, 2018.

(56) References Cited

U.S. PATENT DOCUMENTS

| | | | | |
|---|---|---|---|---|
| 2,701,559 | A | 2/1955 | Cooper | |
| 2,717,437 | A | 9/1955 | De Mestral | |
| 2,811,969 | A | 11/1957 | Shubert | |
| 2,839,049 | A | 6/1958 | Maclean | |
| 2,847,005 | A | 8/1958 | Bourne | |
| 2,955,591 | A | 10/1960 | Maclean | |
| 3,018,498 | A | 1/1962 | Wasserman | |
| 3,126,890 | A * | 3/1964 | Deming, Sr. | A61B 17/4208 |
| | | | | 2/161.7 |
| 3,263,681 | A | 8/1966 | Nechtow | |
| 3,511,242 | A | 5/1970 | Agnone | |
| 3,554,185 | A | 1/1971 | Kohl | |
| 3,559,226 | A | 2/1971 | Burns | |
| 3,628,522 | A | 12/1971 | Kato | |
| 3,774,590 | A | 11/1973 | McDonald | |
| 3,777,743 | A | 12/1973 | Binard | |
| RE27,915 | E | 2/1974 | Kohl | |
| 3,796,211 | A | 3/1974 | Kohl | |
| 3,877,464 | A | 4/1975 | Vermes | |
| 3,945,372 | A | 3/1976 | Milan | |
| 3,995,629 | A | 12/1976 | Patel | |
| 4,016,865 | A | 4/1977 | Fredericks | |
| 4,061,146 | A | 12/1977 | Baehr | |
| 4,127,113 | A | 11/1978 | Nollan | |
| 4,168,698 | A | 9/1979 | Ostergard | |
| 4,227,537 | A | 10/1980 | Suciu | |
| 4,245,653 | A | 1/1981 | Weaver | |
| 4,384,587 | A | 5/1983 | Milgrom | |
| 4,396,022 | A | 8/1983 | Marx | |
| 4,430,076 | A | 2/1984 | Harris | |
| 4,465,072 | A | 8/1984 | Taheri | |
| 4,467,816 | A | 8/1984 | Schluter | |
| 4,620,548 | A | 11/1986 | Hasselbrack | |
| 4,641,662 | A | 2/1987 | Jaicks | |
| D289,926 | S | 5/1987 | Lonky | |
| 4,700,713 | A | 10/1987 | Kist | |
| 4,754,764 | A | 7/1988 | Bayne | |
| 4,757,826 | A | 7/1988 | Abdulhay | |
| 4,759,376 | A | 7/1988 | Stormby | |
| 4,762,133 | A | 8/1988 | Bayne | |
| 4,763,669 | A | 8/1988 | Jaeger | |
| 4,777,947 | A | 10/1988 | Zwick | |
| 4,781,202 | A | 11/1988 | Janese | |
| 4,872,243 | A | 10/1989 | Fischer | |
| 4,873,992 | A | 10/1989 | Bayne | |
| 4,892,831 | A | 1/1990 | Wong | |
| 4,932,857 | A | 6/1990 | Nishino | |
| 4,946,389 | A | 8/1990 | Weissenberger | |
| 4,951,684 | A | 8/1990 | McMillan | |
| 4,961,430 | A | 10/1990 | Sheahon | |
| 4,965,725 | A | 10/1990 | Rutenberg | |
| 5,022,408 | A | 6/1991 | Mohajer | |
| 5,067,195 | A | 11/1991 | Sussman | |
| 5,069,224 | A | 12/1991 | Zinnanti, Jr. | |
| 5,092,345 | A | 3/1992 | Sakita | |
| 5,121,752 | A | 6/1992 | Canna | |
| 5,133,361 | A | 7/1992 | Cox | |
| 5,154,694 | A | 10/1992 | Kelman | |
| 5,184,626 | A | 2/1993 | Hicken | |
| 5,191,899 | A | 3/1993 | Strickland | |
| 5,195,964 | A | 3/1993 | Kletzky | |
| 5,197,949 | A | 3/1993 | Angsupanich | |
| 5,250,061 | A | 10/1993 | Michelson | |
| 5,253,652 | A | 10/1993 | Fast | |
| 5,257,182 | A | 10/1993 | Luck | |
| 5,259,391 | A | 11/1993 | Altshuler | |
| 5,287,272 | A | 2/1994 | Rutenberg | |
| 5,315,740 | A | 5/1994 | Provost | |
| 5,329,938 | A | 7/1994 | Lonky | |
| 5,370,128 | A | 12/1994 | Wainwright | |
| 5,421,346 | A | 6/1995 | Sanyal | |
| 5,445,164 | A | 8/1995 | Worthen | |
| 5,456,265 | A | 10/1995 | Yim | |
| 5,462,063 | A | 10/1995 | Kist | |
| 5,464,409 | A | 11/1995 | Mohajer | |
| 5,470,308 | A | 11/1995 | Edwards | |
| 5,476,104 | A | 12/1995 | Sheahon | |
| 5,535,756 | A | 7/1996 | Parasher | |
| 5,544,650 | A | 8/1996 | Boon | |
| 5,549,563 | A | 8/1996 | Kroner | |
| 5,623,941 | A | 4/1997 | Hedberg | |
| 5,643,307 | A | 7/1997 | Turkel | |
| 5,649,943 | A | 7/1997 | Amoils | |
| 5,713,369 | A | 2/1998 | Tao | |
| 5,722,423 | A | 3/1998 | Lind | |
| 5,738,109 | A | 4/1998 | Parasher | |
| 5,761,760 | A | 6/1998 | Dumler | |
| 5,785,785 | A | 7/1998 | Chesley | |
| 5,792,160 | A | 8/1998 | Weiss | |
| 5,794,774 | A * | 8/1998 | Porcelli | A46B 11/0003 |
| | | | | 206/369 |
| 5,800,362 | A | 9/1998 | Kobren | |
| 5,807,282 | A | 9/1998 | Fowler | |
| 5,857,982 | A | 1/1999 | Milliman | |
| 5,865,765 | A | 2/1999 | Mohajer | |
| 5,868,509 | A | 2/1999 | Crutcher | |
| 5,868,668 | A | 2/1999 | Weiss | |
| 5,882,329 | A | 3/1999 | Patterson | |
| 5,899,850 | A | 5/1999 | Ouchi | |
| 5,913,857 | A | 6/1999 | Ritchart | |
| 5,916,228 | A | 6/1999 | Ripich | |
| 5,937,870 | A | 8/1999 | Gueret | |
| 5,951,550 | A | 9/1999 | Shirley | |
| 6,053,877 | A | 4/2000 | Banik | |
| 6,110,130 | A | 8/2000 | Kramer | |
| 6,132,421 | A | 10/2000 | Clapham | |
| 6,193,674 | B1 | 2/2001 | Zwart | |
| 6,258,044 | B1 | 7/2001 | Lonky | |
| 6,297,044 | B1 | 10/2001 | Eisen | |
| 6,302,853 | B1 | 10/2001 | Sak | |
| 6,336,905 | B1 | 1/2002 | Colaianni | |
| 6,346,086 | B1 | 2/2002 | Maksem | |
| 6,376,905 | B2 | 4/2002 | Hisano | |
| 6,379,315 | B1 | 4/2002 | Claren | |
| 6,387,058 | B1 | 5/2002 | Wallach | |
| 6,394,966 | B1 | 5/2002 | Gill | |
| 6,402,700 | B1 | 6/2002 | Richards | |
| 6,408,492 | B1 | 6/2002 | Sparks | |
| 6,494,845 | B2 | 12/2002 | Rutenberg | |
| 6,595,947 | B1 | 7/2003 | Mikszta | |
| 6,676,609 | B1 | 1/2004 | Rutenberg | |
| 6,730,085 | B2 | 5/2004 | George | |
| 6,740,049 | B2 | 5/2004 | Wallach | |
| 6,790,654 | B2 | 9/2004 | Malinge | |
| 6,860,738 | B2 | 3/2005 | Bachmann | |
| 7,004,913 | B1 | 2/2006 | Rutenberg | |
| 7,137,956 | B2 | 11/2006 | Nishtalas | |
| 7,156,814 | B1 | 1/2007 | Williamson, IV | |
| 7,157,233 | B2 | 1/2007 | Fischer | |
| 7,413,551 | B2 | 8/2008 | Decker | |
| 7,517,323 | B2 | 4/2009 | Ng | |
| D605,407 | S | 12/2009 | Wagner | |
| 7,749,173 | B2 | 7/2010 | Larkin | |
| 7,836,539 | B2 | 11/2010 | Moskovich | |
| 7,871,574 | B2 | 1/2011 | Peltier | |
| 8,152,739 | B1 | 4/2012 | McCully | |
| 8,348,856 | B1 | 1/2013 | Malanowska | |
| 8,439,847 | B2 | 5/2013 | Larkin | |
| 8,517,956 | B1 | 8/2013 | Malanowska | |
| 8,617,183 | B2 | 12/2013 | Schneider | |
| 8,652,067 | B2 | 2/2014 | Lonky | |
| 8,795,197 | B2 | 8/2014 | Lonky | |
| 9,028,484 | B2 | 5/2015 | Craig | |
| 9,044,213 | B1 | 6/2015 | Lonky | |
| 9,282,950 | B2 | 3/2016 | Klein | |
| 9,282,951 | B2 | 3/2016 | Lonky | |

(56)                    References Cited

U.S. PATENT DOCUMENTS

| | | |
|---|---|---|
| 9,393,394 B2 | 7/2016 | Lonky |
| 9,421,346 B2 | 8/2016 | Callahan |
| 9,687,642 B2 | 6/2017 | Lonky |
| 9,895,140 B1 | 2/2018 | Lonky |
| 10,201,332 B1 | 2/2019 | Lonky |
| 10,258,780 B2 | 4/2019 | Lonky |
| 11,013,466 B2 | 5/2021 | Lonky |
| 11,083,631 B2 | 8/2021 | Dunn |
| 11,571,188 B1 | 2/2023 | Lonky |
| 2001/0022063 A1 | 9/2001 | Korteweg |
| 2002/0068881 A1 | 6/2002 | Kobren |
| 2002/0165467 A1 | 11/2002 | Rutenberg |
| 2003/0055373 A1 | 3/2003 | Sramek |
| 2003/0109804 A1 | 6/2003 | Auerbach |
| 2003/0203119 A1* | 10/2003 | Witter .................... B05C 17/00 |
| | | 15/227 |
| 2004/0029658 A1 | 2/2004 | Howe |
| 2004/0116827 A1 | 6/2004 | Tiberio |
| 2004/0120989 A1 | 6/2004 | Vadas |
| 2004/0138642 A1 | 7/2004 | Fischer |
| 2004/0181170 A1 | 9/2004 | Wallach |
| 2004/0181185 A1 | 9/2004 | Lee |
| 2004/0220478 A1 | 11/2004 | Wallace |
| 2004/0236247 A1 | 11/2004 | Rizvi |
| 2004/0260199 A1 | 12/2004 | Hardia |
| 2004/0260201 A1 | 12/2004 | Mueller |
| 2004/0267191 A1 | 12/2004 | Gifford |
| 2005/0059905 A1 | 3/2005 | Boock |
| 2005/0074269 A1 | 4/2005 | Asselin |
| 2005/0085845 A1 | 4/2005 | Hilaire |
| 2005/0215920 A1 | 9/2005 | Isa |
| 2005/0251093 A1 | 11/2005 | Abou-Kansoul |
| 2005/0261603 A1 | 11/2005 | Witenberg |
| 2006/0052805 A1 | 3/2006 | Cwik |
| 2006/0122641 A1 | 6/2006 | Eberle |
| 2006/0200043 A1 | 9/2006 | Jannetty |
| 2007/0060839 A1 | 3/2007 | Richardson |
| 2007/0073186 A1 | 3/2007 | Decker |
| 2007/0093727 A1 | 4/2007 | Feuer |
| 2007/0100335 A1 | 5/2007 | Fischer |
| 2007/0107155 A1 | 5/2007 | Kacher |
| 2007/0118947 A1 | 5/2007 | Lorenzo |
| 2007/0135731 A1 | 6/2007 | Ward |
| 2007/0161042 A1 | 7/2007 | Zuk |
| 2007/0255177 A1 | 11/2007 | Pronovost |
| 2007/0270715 A1 | 11/2007 | Ng |
| 2007/0282222 A1 | 12/2007 | Larkin |
| 2007/0282223 A1 | 12/2007 | Larkin |
| 2008/0188769 A1 | 8/2008 | Lu |
| 2008/0216763 A1 | 9/2008 | Ebert |
| 2008/0262384 A1 | 10/2008 | Wiederkehr |
| 2009/0012424 A1 | 1/2009 | Huschmand |
| 2009/0024155 A1 | 1/2009 | Lee |
| 2009/0043224 A1 | 2/2009 | Lundkvist |
| 2009/0112239 A1 | 4/2009 | To |
| 2009/0149860 A1 | 6/2009 | Scribner |
| 2009/0275859 A1 | 11/2009 | Kim |
| 2009/0326414 A1 | 12/2009 | Peltier |
| 2010/0011483 A1 | 1/2010 | Pinkart |
| 2010/0210968 A1 | 8/2010 | Lonky |
| 2010/0249649 A1 | 9/2010 | Larkin |
| 2010/0306945 A1* | 12/2010 | Methfessel .......... A61B 17/244 |
| | | 15/208 |
| 2011/0152881 A1 | 6/2011 | Conner |
| 2011/0172557 A1 | 7/2011 | Lonky |
| 2011/0268610 A1 | 11/2011 | Recknor |
| 2013/0066233 A1 | 3/2013 | Klein |
| 2013/0158429 A1 | 6/2013 | Sepsick |
| 2013/0267870 A1 | 10/2013 | Lonky |
| 2014/0128773 A1 | 5/2014 | Lonky |
| 2014/0358158 A1 | 12/2014 | Einarsson |
| 2016/0100862 A1 | 4/2016 | Parys |
| 2017/0021151 A1 | 1/2017 | Lonky |

| | | |
|---|---|---|
| 2017/0112477 A1 | 4/2017 | Benning |
| 2018/0035983 A1 | 2/2018 | Lonky |
| 2018/0296800 A1 | 10/2018 | Kato et al. |

FOREIGN PATENT DOCUMENTS

| | | | |
|---|---|---|---|
| EP | 2166965 | | 7/2008 |
| GB | 2332367 | * | 6/1999 |
| WO | WO2007101994 | | 9/2007 |
| WO | WO2009012392 | | 1/2009 |
| WO | WO2012125757 | | 9/2012 |
| WO | WO2015134568 | | 9/2015 |

OTHER PUBLICATIONS

Boon et al., "Confocal Sectioning of Thick, Otherwise Undiagnosable Cell Groupings in Cervical Smears" Acta Cytol., vol. 37, pp. 40-48 (1991).

Boon et al., "Exploiting the "Toothpick Effect" of the Cytobrush by Plastic Embedding of Cervical Samples" Acta Cytol., vol. 35, pp. 57-63 (1991).

Boon, "A model for quantitative follow-up studies of cervical lesions," Diagn Cytopathol., 1992, vol. 8(1), pp. 8-17.

Butler, B., "Kuper brush in the diagnosis of endometrial lesions," The Lancet, Dec. 1971, vol. 298(7739), pp. 1390-1392.

DeGirolami, "Histo-brush technic for endometerial tissue study," Obstet Gynecol., Dec. 1961, vol. 28(6), pp. 861-866.

Dowlatshahi et al., "Evaluation of brush cytology as an independent technique for detection of esophageal carcinoma" J Thoracic and Cardiovascular Surgery, vol. 89, No. 6, pp. 848-851, Jun. 1985.

Fennessy, "Transbronchial biopsy of peripheral lung lesions," Radiology, May 1967, vol. 88(5), pp. 878-882.

Firestone, "Needle lung biopsy, bronchial brushing and mediastinoscopy in Management of Chest Diseases," Calif Med., Sep. 1973, vol. 119(3), pp. 1-5.

Gahres et al., "Histo-brush technic for Endometrial Tissue Study", Obstet Gynecol vol. 28, pp. 861-866 (1966)—Front Page Only.

Goldstein, "Esophageal biopsy utilizing a flexible brush," Gastrointest Endosc., Aug. 1968, vol. 15(1), pp. 53-55.

Granqvist, "Colonoscopic biopsies and cytological exam in chronic ulcerative colitis," J Gastroenterology, Apr. 1980, vol. 15(3), pp. 283-288.

Hardwick, "Brush biopsy in the diagnosia of neoplasia in Bartlett's esophagus," Disease Esophagus, Oct. 1997, vol. 10(4), pp. 233-237.

Iaccarino, "Percutaneous intralesional brushing of cystic lesions of bone: a technical improvement of diagnostic cytology," Skelatal Radiol, 1990, vol. 19(3), pp. 187-190.

Johnsson, "Cytological brush techniques in malignant disease of the endometrium," Acta Obstet Gynecol Scand, Jan. 1968, vol. 47, issue 1, pp. 38-51.

Johnsson, "Cytological diagnosis of endometrial disorders with a brush technique," Acta Obstet Gynecol Scand., 1971, vol. 50(2), pp. 141-148.

Kovnat, "Bronchial brushing through the flexible fiberoptic bronchoscope in the diagnosis of peripheral pulmonary lesions," Chest, Feb. 1975, vol. 67(2), pp. 179-184.

Liu, "Transcervical chorionic villus biopsy with a brush," Prenat Diagn., Sep.-Oct. 1985, vol. 5(5), pp. 349-355.

Maksem, "Endometrial brush cytology of advanced postmenopausal endometrium . . . ," Diagn Cytopathol., Nov. 1998, vol. 19(5), pp. 338-343.

Matsuda, "Bronchial brushing and bronchial biopsy: comparison of diagnostic accuracy and cell typing reliability in lung cancer," Thorax, Jun. 1986, vol. 41(6), pp. 475-479.

Meulman, "Predictions of various grades of cervical neoplasia on plastic-embedded cytobrush samples," Anal Quant Cytol Histol., Feb. 1992, vol. 14(1), pp. 60-72.

Mills, "Transcatheter brush biopsy of intravenous tumor thrombi," Radiology, Jun. 1978, vol. 127(3), pp. 667-670.

Morteza, "Brush and forceps biopsy of billary ducts via percutaneous transhepatic catheterization," Radiology, Jun. 1980, vol. 135, pp. 777-778.

(56)         References Cited

OTHER PUBLICATIONS

Moskowitz, "To brush or not to brush is there really a question?," Chest, Jun. 1971, vol. 59(6), pp. 648-650.

Mullins, "A new technique for transbronchial biopsy in infants and small children," Pediatr Pulmonol, Oct. 1995, vol. 20(4), pp. 253-257.

Parasher V.K. and Huibregtse, K., Endoscopic retrograde wire-guided cytology of malignant biliary strictures using a novel scraping brush, Gastrointestinal Endoscopy, (1998) 48 (3) 288-290.

Payne, "Diagnostic accuracy of cytology and biopsy in primary bronchial carcinoma," Thorax, Jun. 1979, vol. 43(3), pp. 294-299.

Pipkorn, "A brush to harvest cells from the nasal mucosa for microscopic and biochemical analysis," J Immunol Methods, Aug. 9, 1988, vol. 112(1), pp. 37-42.

Portner, "New devices for biliary drainage and biopsy," Radiology, Jun. 1982, vol. 138, pp. 1191-1195.

Raney, "Detection of carcinoma of upper urinary tract with steerable brush biopsy," Urology, Jul. 1979, vol. 14(1), pp. 77-78.

Ravinsky, "Cytologic features of primary adenoid cystic carcinoma of the uterine cervix. A case report," Acta Cytol., Nov.-Dec. 1996, vol. 40(6), pp. 1304-1308.

Riise et al., "Bronchial brush biopsies for studies of epithelial inflammation in stable asthma and nonobstructive chronic bronchitis" Eur Respir J vol. 9, pp. 1665-1671 (1996).

Riise, "A bronchoscopic brush biopsy study of large airway mucosal pathology in smokers . . . ," Eur Respir J., Apr. 1992, vol. 5(4), pp. 382-386.

Roth et al., "Cytologic Detection of Esophageal Squamous Cell . . . ." Cancer, vol. 80, No. 11, Dec. 1, 1997.

Sanderson, "Use of a new controllable-tip brush with the flexible fiber bronchoscope," Chest, Jun. 1974, vol. 65(6), pp. 620-621.

Sheline, "Fluoroscopically guided retrograde brush biopsy in the diagnosis of transitional cell carcinoma of the upper urinary tract . . . ," Am J Roentgenology, Sep. 1989, vol. 153(2), pp. 313-316.

Willson, "Bronchial brush biopsy with a controllable brush," Am J Roentgenology, Jul. 1970, vol. 109(3), pp. 471-477.

Zavala, "Use of Bronchofiberscope for bronchial brush biopsy: diagnostic results and comparison with other brushing techniques," Chest, Jun. 1973, vol. 63(6), pp. 889-892.

Zeppa, "A model for quantitative follow-up studies of cervical lesions," Diagn Cytopathol, 1992, vol. 8(1), pp. 8-17.

ISR of Application No. 08796246, PCT/US2008/70341 published as WO2009012392 dated Oct. 22, 2008, 6 pages.

Extended ESR of Application No. 08796246, PCT/US2008/070341, May 11, 2012, 6 pages.

Extended ESR of Application No. 17744713.3, PCT/US2017/014190, Aug. 19, 2019, 7 pages.

ISR of PCT/US2017/014190, Apr. 10, 2017, 7 pages.

Australian Patent Exam Report 20130806, Aug. 6, 2013, 5 pages.

Communication under Article 94 of Application No. 08796246, PCT/US2008/070341, Jun. 6, 2015, 5 pages.

Article 94(3) European Communication, Application No. 08796246, PCT/US2008/070341, Jul. 4, 2016, 4 pages.

International Search Report of PCT/US17/14190, published as WO2017/132051, dated Apr. 10, 2017, 13 pages.

International Preliminary Report on Patentability of PCT/US17/14190, published as WO2017/132051, dated Jul. 31, 2018, 7 pages.

* cited by examiner

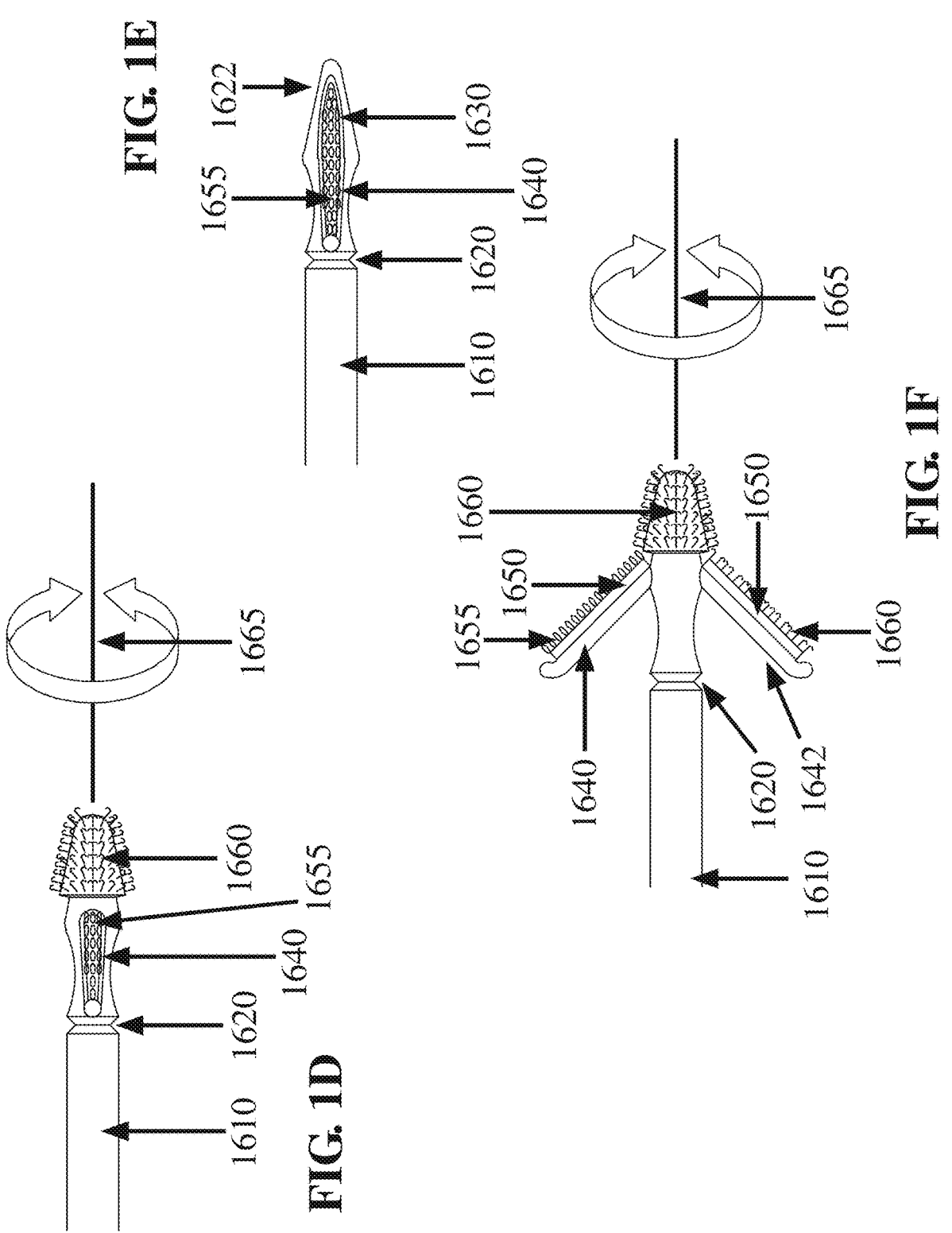

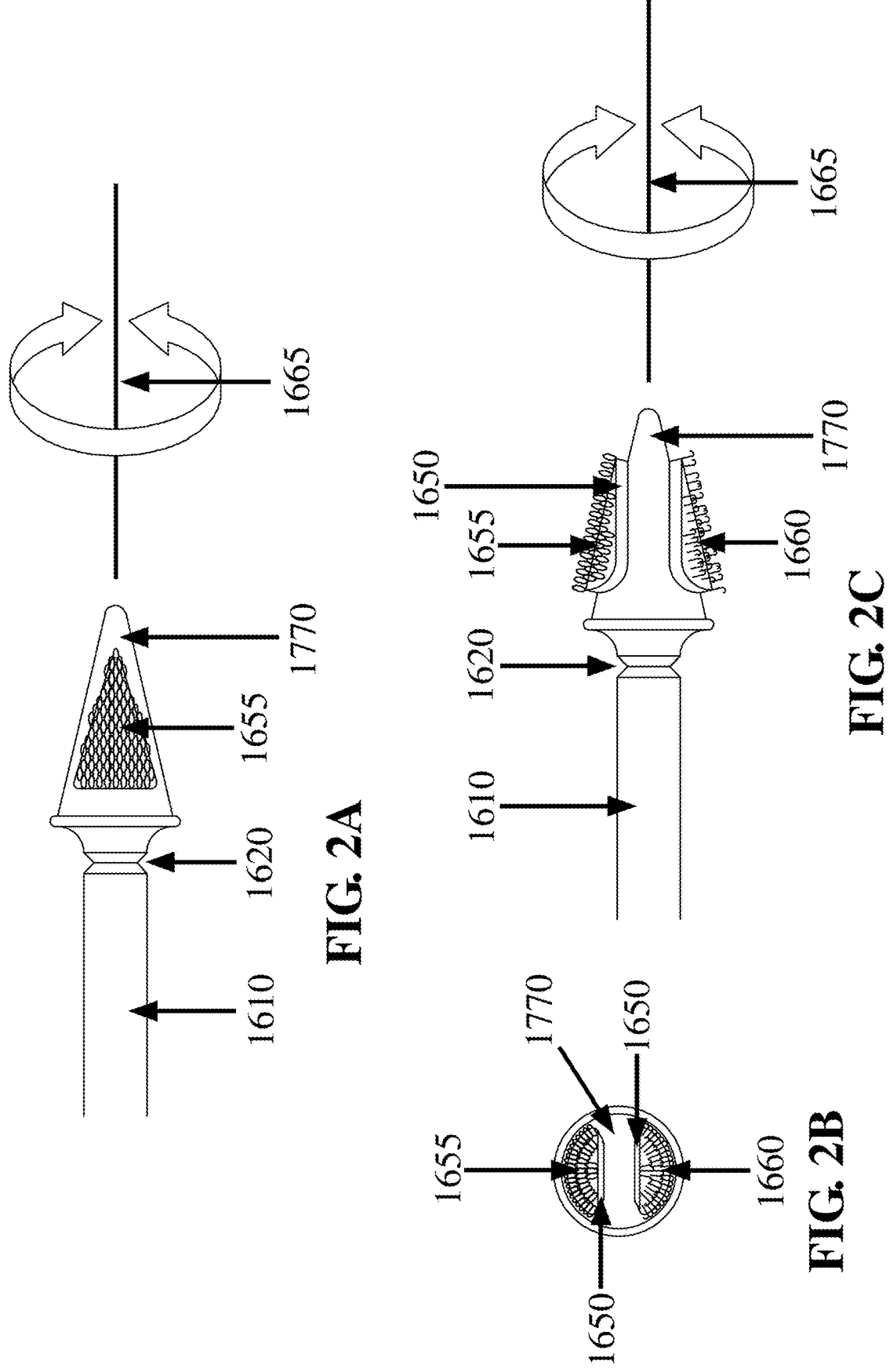

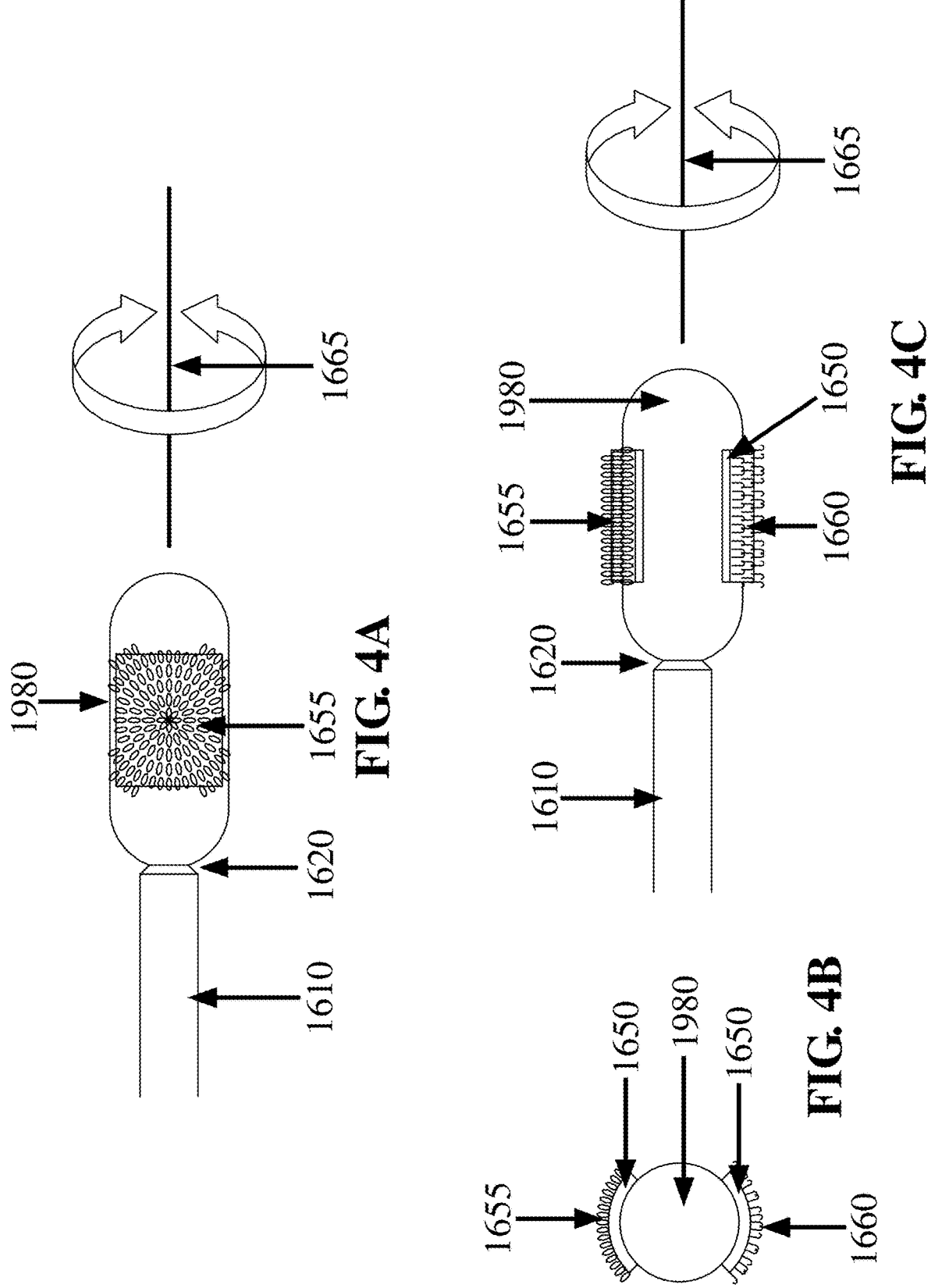

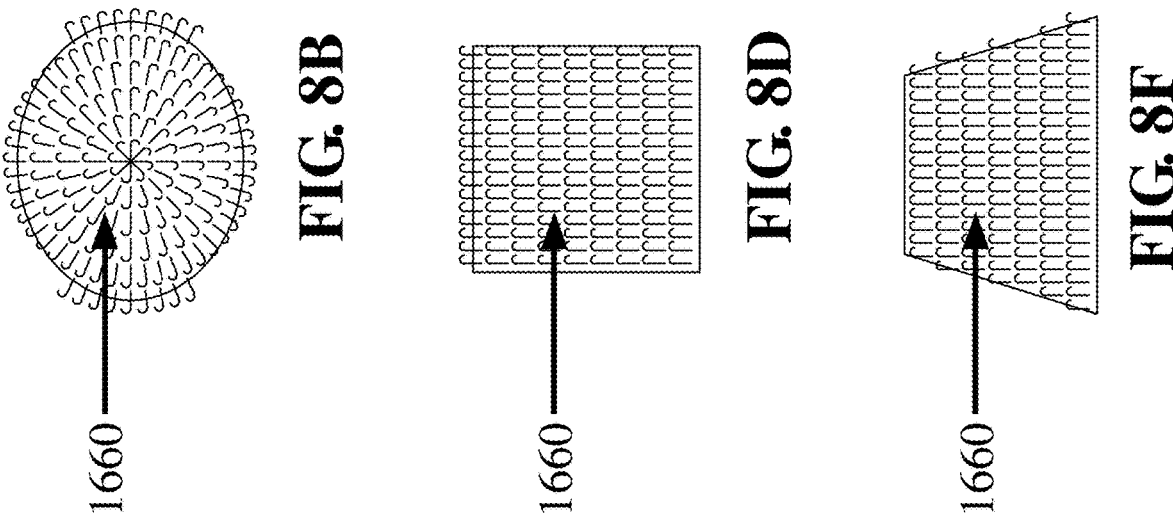
1660
FIG. 8B
1660
FIG. 8D
1660
FIG. 8F
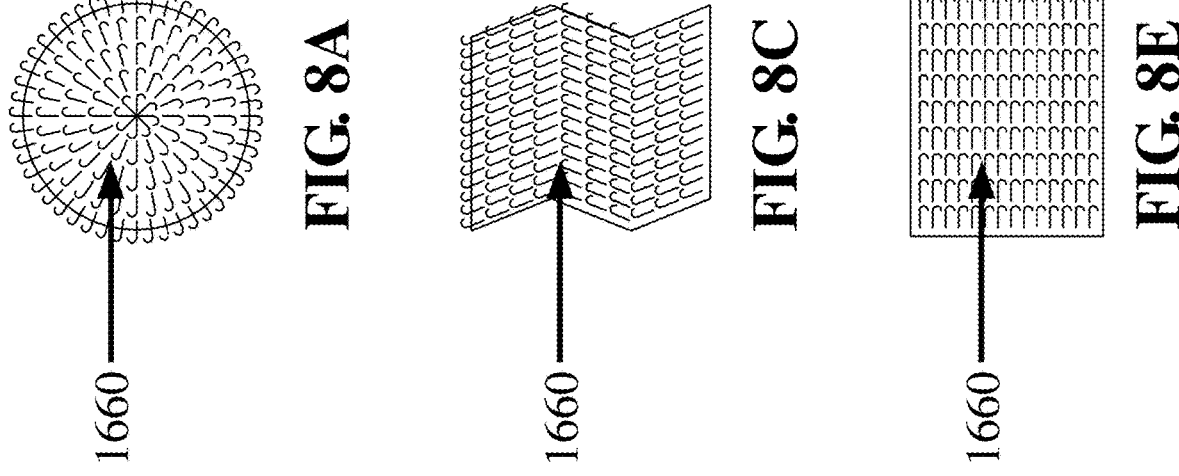
1660
FIG. 8A
1660
FIG. 8C
1660
FIG. 8E

1655

1660

2593

2593

1655

1660

1650

2593

1650

1660

1655

2593

1655

1660

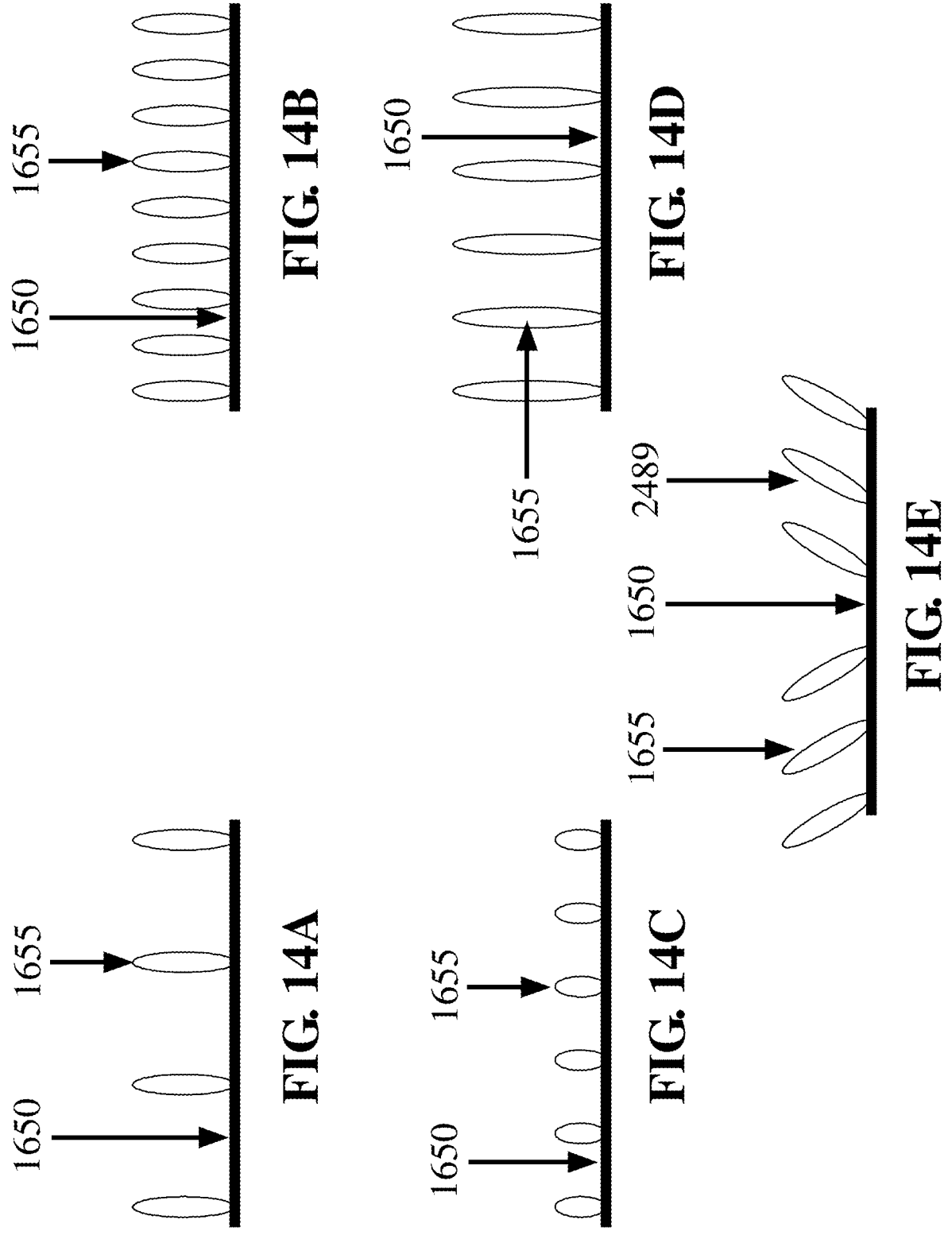

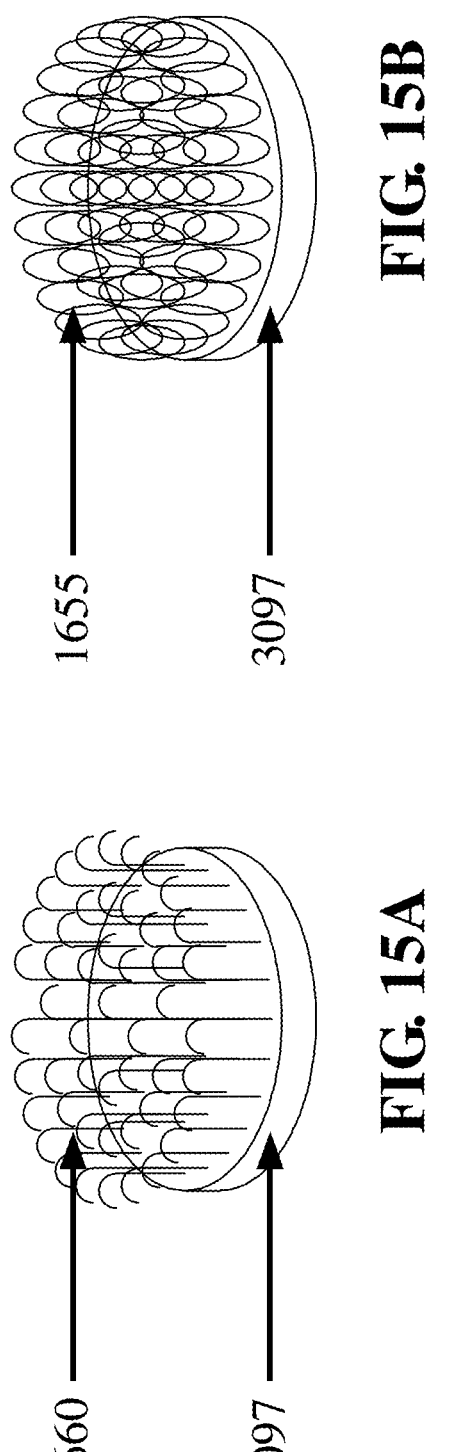
1655
3097
FIG. 15B
1660
3097
FIG. 15A
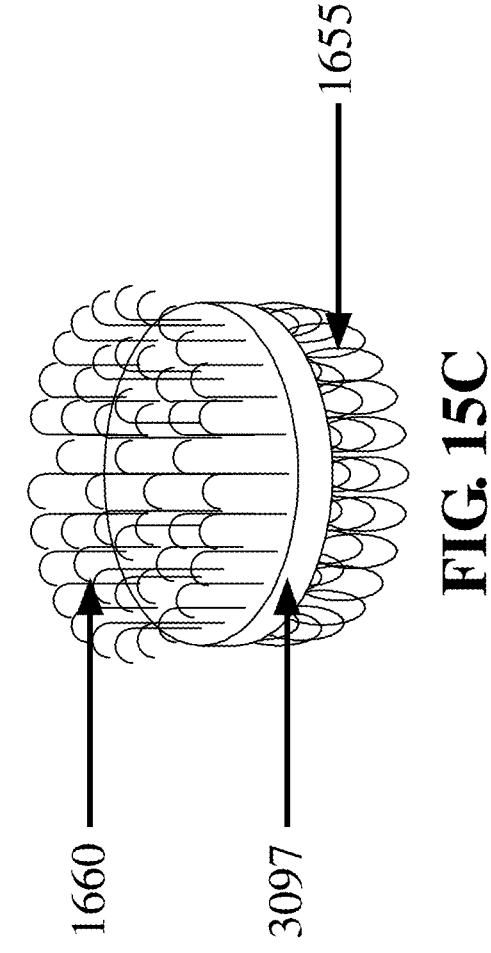
1655
FIG. 15C
1660
3097

SCRAPE AND SWEEP FRICTIONAL TISSUE SAMPLING AND COLLECTION METHOD AND DEVICE

PRIORITY CLAIM

This application is a continuation in part of and claims priority to (1) U.S. Utility application Ser. No. 16/573,920 entitled "SCRAPE AND SWEEP FRICTIONAL TISSUE SAMPLING AND COLLECTION METHOD AND DEVICE" filed Sep. 17, 2019 which claims priority to (2) U.S. provisional application No. 62/733,933, filed Sep. 20, 2018, inventor Neal M. Lonky entitled "SCRAPE AND SWEEP FRICTIONAL TISSUE SAMPLING AND COL-LECTION METHOD AND DEVICE", (3) U.S. provisional application No. 62/782,178, filed Dec. 19, 2018, inventor Neal M. Lonky entitled "SCRAPE AND SWEEP FRIC-TIONAL TISSUE SAMPLING AND COLLECTION METHOD AND DEVICE", and (4) U.S. provisional appli-cation No. 62/840,354, filed Apr. 29, 2019, inventor Neal M. Lonky entitled "SCRAPE AND SWEEP FRICTIONAL TISSUE SAMPLING AND COLLECTION METHOD AND DEVICE". Each of these applications (1)-(4) are herein expressly incorporated by reference in its entirety and for all purposes.

CROSS REFERENCE TO RELATED APPLICATION

This application is related to the following applications: (5) U.S. Utility patent application Ser. No. 12/669,638, entitled 'FRICTIONAL TRANS-EPITHELIAL TISSUE DISRUPTION AND COLLECTION APPARATUS AND METHOD OF INDUCING AND/OR AUGMENTING AN IMMUNE RESPONSE' inventor Neal M. Lonky et al., filed Jan. 19, 2010 which issued as U.S. Pat. No. 8,652,067; (6) U.S. Utility patent application Ser. No. 13/072,775, entitled 'FRICTIONAL TISSUE SAMPLING AND COLLECTION METHOD AND DEVICE' inventor Neal M. Lonky, filed Mar. 28, 2011 which issued as U.S. Pat. No. 9,044,213 and (7) U.S. Utility patent application Ser. No. 15/709,790, entitled 'CELL AND TISSUE COLLECTION METHOD AND DEVICE' inventor Neal M. Lonky, filed Sep. 20, 2017. Each of these applications (5)-(7) are herein expressly incorporated by reference in their entirety and for all pur-poses.

FIELD OF THE INVENTION

This invention relates to a method of and device for removing tissue from a body surface suitable for biopsy tissue, tissue culture, or molecular test analysis.

BACKGROUND OF THE INVENTION

A lesion is caused by any process that alters or damages tissue. A lesion can be defined as any pathological or traumatic discontinuity of tissue with partial loss of tissue function. The concept of a lesion includes wounds, sores, ulcers, tumors, cataracts and any other tissue damage. Lesions can range from areas of suspected neoplastic change, denuded skin or wound sites, skin sores associated with eczema to the changes in lung tissue that occur in tuberculosis. Generally, a lesion can be characterized by the epithelium covering the connective tissue becoming fragile, leading to ulceration and bleeding. Subsequent changes could include infection of the associated areas with bacterial or viral organisms.

Human papillomaviruses (HPV) are responsible for many cutaneous and mucosal lesions. Some viral genotypes are considered to be the causal agents of cervical cancer. Some viral genotypes are considered to be the causal agents of oropharyngeal cancers as well. Natural genital HPV infec-tion seems to be poorly immunogenic because of its non-productive and non-inflammatory characteristics and also because of mechanisms developed by the virus to counteract the immune response. Cervicovaginitis refers to inflamma-tion of the squamous epithelium of the vagina and cervix caused by an inflammatory reaction to an infection. This damage leads to desquamation and ulceration, which can cause a reduction in the epithelial thickness due to loss of superficial and part of the intermediate layers of cells. In the deeper layers, the cells are swollen with infiltration of neutrophils in the intercellular space. The surface of the epithelium is covered by cellular debris and inflammatory mucopurulent secretions. The underlying connective tissue is congested with dilatation of the superficial vessels and with enlarged and dilated stromal papillae. Rare and uncom-mon cervical infections, due to tuberculosis, schistosomiasis and amoebiasis, cause extensive ulceration and necrosis of the cervix with symptoms and signs mimicking invasive cancer. Herpes simplex virus (HSV) can be present on the mucosal lining of the mouth or genitals. A large coalesced ulcer due to HSV can also mimic the appearance of invasive cancer. Chronic inflammation causing recurrent ulceration and healing of the cervix can result in a distortion of the cervix. Infections with the pathogenic fungi *Cryptococcus neoformans, Histoplasma capsulatum,* and *Coccidioides immitis* can be disseminated and some, e.g., *C. neoformans,* can result in pneumonia or meningitis. Longstanding viral, bacterial, fungal or protozoal infection and inflammation may lead to white or pink appearance as a result of fibrosis.

Neoplastic lesions of the oral or pharyngeal mucosa may develop secondary to immortalization of cell lines following human papilloma virus infection, or neoplastic changes induced by carcinogens such as tobacco. The tendency of oral mucosa to undergo neoplastic transformation towards malignancy can be reflected in cells exfoliated from its surface. Sometimes keratin may preclude proper exfoliation to the tissue surface. Simple swabs of oral mucosa may not reflect the neoplastic grade of the tissues below. The aim of the invention is to dislodge cells and shallow fragments of tissue using the rigid hooks with mild to moderate pressure and then sweep the dislodged cellular and tissue originating from below the tissue surface to approximately mid-way into the epithelium, into the loop array for collection and later analysis.

Neoplastic lesions exist within body cavities that can be accessed using catheters, flexible probes, or catheters that deploy balloons. Specifically, those intra-uterine cavity lesions that are not amenable to suction biopsy due to atrophy or other characteristics that make them less likely to detach or exfoliate could be amenable to a scrape and sweep methodology with rigid hooks and fabric loops, respectively.

Lesions resulting in wound generation and denudation and necrosis of epithelium may occur as a result of diabetes, chronic compression in paralyzed/bed-ridden patients, or patients with vascular insufficiency to the associated tissues, or colonization with pathogens. The resulting wounds often are slow to repair or heal, and require debridement to revitalize the tissues, induce the micro-circulation to bring in a healing immune response, and clear away pathogens.

Occasionally the wound may need tissue sampling to evaluate the wound biome or any evidence of neoplasia.

Previous devices to obtain a biopsy sample include brushes with rigid bristles that puncture and shear epithelial surfaces (U.S. Pat. No. 5,535,756 'Catheter with simultaneous brush cytology and scrape biopsy capability', U.S. Pat. No. 6,258,044 'Apparatus and method for obtaining transepithelial specimen of a body surface using a non-lacerating technique', U.S. Pat. No. 6,494,845 'Retractable brush for use with endoscope for brush biopsy' and U.S. Pat. No. 6,132,421 'Integrated epithelial removal tool'), single metal or plastic curettes that extend in a parallel direction to the applicator handle and are much larger than the innovation (U.S. Pat. No. 4,641,662 'Endocervical curette system' and U.S. Pat. No. 6,730,085 'Surgical biopsy instrument'), scalpels or similar bladed sharp cutting tools (U.S. Pat. No. 5,857,982 'Apparatus and method for removing tissue', U.S. Pat. No. 5,800,362 'Cervical biopsy device', U.S. Pat. No. 3,774,590 'Uterine Specimen Collecting Method', U.S. Pat. No. 5,092,345 'Uterine cell sampler', U.S. Pat. No. 4,061,146 'Tissue macerating instrument', U.S. Pat. No. 5,868,668 'Surgical instrument', U.S. Pat. No. 6,053,877 'Movable sample tube multiple biopsy sampling device', U.S. Pat. No. 5,470,308 'Medical probe with biopsy stylet', U.S. Pat. No. 7,137,956 'Endoscopic submucosal core biopsy device', U.S. Pat. No. 4,168,698 'Endocervical strip biopsy instrument' and U.S. Pat. No. 4,757,826 'Endocervical biopsy instrument'; and U.S. Publication Nos. 2005/0059905 'Tissue extraction and maceration device' and 2007/0093727 'Cervical tissue biopsy system and methods of use'), or very large electrified metal loops used to produce excisional biopsies (U.S. Pat. No. 5,913,857 'Methods and devices for collection of soft tissue' and U.S. Pat. No. 5,951,550 'Endocervical conization electrode apparatus'). One device performs simultaneous brush cytology and scrape biopsy on structures with an organic duct (U.S. Pat. No. 5,535,756, 'Catheter with simultaneous brush cytology and scrape biopsy capability'). U.S. Pat. No. 5,643,307 'Colposcopic Biopsy Punch with Removable Multiple Sample Basket' has also been proposed to obtain biopsy samples when examining the cervix.

SUMMARY OF THE INVENTION

There is significant incentive for being able to remove tissue from body surfaces, and obtain a biopsy sample along with collecting cells from a lesion in a manner which involves minimal pain and in the least intrusive manner. In an embodiment of the present invention, an apparatus for obtaining a tissue or biopsy sample includes a handle, a flat, concave or convex surface at a distal end of the handle, and a fabric for functionally abrading tissue surfaces applied to the surface. In an embodiment of the present invention, an apparatus for obtaining a histological sample includes a handle, a flat, concave or convex facet surface on the head at a distal end of the handle, and a fabric for functionally abrading epithelial surfaces. In an alternative embodiment of the present invention, an apparatus for obtaining a histological sample includes a handle, a flat, concave or convex facet surface on the head at a distal end of the handle, and a fabric for functionally abrading epithelial surfaces including a backing material and a plurality of fenestrated loops attached to the backing material. A concave facet surface with an adherent abrasive fabric allows the handle to be rotated and remain on the desired location to collect a biopsy from convex tissue surfaces. A convex facet surface with an adhered abrasive fabric allows the hand to be rotated and remain on the desired location to collect a biopsy from concave tissue surfaces. A flat facet surface with an adherent abrasive fabric allows the hand to be rotated and pressed completley without allowing gaps between the abrasion material and a flat surface tissue to be sampled when collecting a biopsy.

In an embodiment of the present invention, the device and the fabric are made of materials that allow the fabric to be ultrasonically welded to the device. In an alternative embodiment of the present invention, the fabric is attached to the device using an adhesive. In various embodiments of the present invention, an ultra violet (UV) light activated adhesive can be used to affix the fabric to the device. A railing or dam can be introduced onto the facet of the head of the device and the UV light activated adhesive is placed within the confines of the dam made on the facet by the railing.

In an embodiment of the invention, the means of applying the frictional fabric to the tissue surface can be the examiner's finger. The finger tip convex surface covered with a cot or glove with the fabric adhered to the ventral finger print area, mounted to the flat sides of the finger, or mounted to the concave dorsal side atop the finger nail can rescess into body cavities or wounds that are ulcerated craters, lie in tunnels, or lie flat on the body surface. With pressure of the finger applied to the tissue, the hooks will depress exposing the frictional hook tips to the target allowing for them to embed into tissue. With rotation or stroking motions, tissue can be abraded and trapped inside the fabric hook array.

In an unexpected result, the utilization of both an abrasive material e.g., hooks and a collector material i.e., an array of loops can result in a more consistent and reliable sampling method and apparatus. The utilization of an abrasive material e.g., hooks can dislodge tissue and entrap large tissue fragments. In an embodiment of the invention, the utilization of a collector material i.e., an array of loops entrap tissue fragments. In an embodiment of the invention, the utilization of hooks and loops enables the large histogical biopsy material isolated by the abrasive hooks and enables the further/additional smaller histogical biopsy material collected by the loops to be trapped. Without being bound to a particular theory, it is possible that this dual approach to retention of differing size fragments enables a more consistent and reliable sampling method and apparatus.

The term 'collector' means a loop, a spatula and/or a sponge. The length of the collector extending from the surface to which the collector is affixed is approximately 3-9 mm. In this range, approximately means plus or minus twenty percent (20%). A bristle is not a collector.

BRIEF DESCRIPTION OF THE DRAWINGS

This invention is described with respect to specific embodiments thereof. Additional features can be appreciated from the Figures in which:

FIG. 1D shows a side view of a propeller FTSC device with one blade 1640 with loops 1655 visible and a patch of hooks 1660 on the nose cone, in accordance with an embodiment of the invention;

FIG. 1E shows a side view of a propeller FTSC device with one blade 1640 with loops 1655 visible where the blade extends from a point closer to the nose cone 1622, in accordance with an embodiment of the invention;

FIG. 1F shows a side view of a propeller FTSC device with two blades visible (1640, 1642), where a first surface on a first blade 1642 presents hooks and acts to frictionally abrade a tissue surfaces while a second surface on a second separate blade 1640 which is not in contact with the first surface presents loops 1655 and a patch of hooks 1660 on the nose cone, in accordance with an embodiment of the invention;

FIG. 2A shows a side view of a tapered FTSC cone shaped biopsy device 1770 attached to a rigid handle 1610 with an etched groove 1620 allowing for detachment, with one surface with loops 1655 visible, in accordance with an embodiment of the invention;

FIG. 2B shows a frontal view of a tapered FTSC cone shaped biopsy device 1770 as shown in FIG. 2A with backing material 1650 of two surfaces visible, where a first surface presents hooks 1660 and acts to frictionally abrade a tissue surfaces while a second surface which is not in contact with the first surface presents loops 1655 and acts to collect the tissue and cell sample that has been abraded at least in part by the first surface, in accordance with an embodiment of the invention;

FIG. 2C shows a side view of a tapered FTSC cone shaped biopsy device (e.g., FIGS. 2A-2B) rotated about the longitudinal axis 1665 ninety (90) degrees from the position shown in FIG. 2A, with backing material 1650 of two surfaces visible, where a first surface presents hooks 1660 and acts to frictionally abrade a tissue surface while a second surface which is not in contact with the first surface presents loops 1655 and acts to collect the tissue and cell sample that has been abraded at least in part by the first surface, in accordance with an embodiment of the invention;

FIG. 4A shows a side view of a capsule FTSC biopsy device 1980 (also known as a capsule cell and tissue sampling device) attached to a rigid handle 1610 with an etched groove 1620 allowing for detachment, with one surface presenting loops 1655 visible, in accordance with an embodiment of the invention;

FIG. 4B shows a frontal view along longitudinal axis 1665 (FIG. 4A) of a capsule FTSC biopsy device 1980 with backing material 1650 of two surfaces visible, where a first surface presents hooks 1660 and acts to frictionally abrade a tissue surfaces while a second surface which is not in contact with the first surface presents loops 1655 and acts to collect the tissue and cell sample that has been abraded at least in part by the first surface, in accordance with an embodiment of the invention;

FIG. 4C shows a side view of a capsule FTSC biopsy device 1980 rotated ninety (90) degrees about longitudinal axis 1665 from the position shown in FIG. 4A, with backing material 1650 of two surfaces visible, where a first surface presents hooks 1660 and acts to frictionally abrade a tissue surface while a second surface which is not in contact with the first surface presents loops 1655 and acts to collect the tissue and cell sample that has been abraded at least in part by the first surface, in accordance with an embodiment of the invention.

FIG. 8A depicts the FTSC device where the fenestrations 1660 are arranged as circles, in accordance with an embodiment of the invention;

FIG. 8B depicts the FTSC device where the fenestrations 1660 are arranged as ovals, in accordance with an embodiment of the invention;

FIG. 8C depicts the FTSC device where the fenestrations 1660 are arranged as zig-zags, in accordance with an embodiment of the invention;

FIG. 8D depicts the FTSC device where the fenestrations 1660 are arranged as squares, in accordance with an embodiment of the invention;

FIG. 8E depicts the FTSC device where the fenestrations 1660 are arranged as rectangles, in accordance with an embodiment of the invention;

FIG. 8F depicts the FTSC device where the fenestrations 1660 are arranged as trapezoids, in accordance with an embodiment of the invention;

In FIG. 13A, a region of hooks 1660 is depicted at the distal fingerprint side of the middle finger of the glove. A region of loops 1655 can be found on the distal palmar region of the thumb. After removal of tissue or cells by the hooks 1660, the tissue or cells can be transferred to the loops 1655 by touching of the thumb and third finger;

In FIG. 13B, a region of hooks 1660 is depicted at the distal fingerprint side of the middle finger of the glove. A region of loops 1655 is positioned proximal to the region of hooks 1660;

FIG. 14A depicts low density loops 1655 on backing material 1650, in accordance with an embodiment of the invention;

FIG. 14B depicts high density loops 1655 on backing material 1650, in accordance with an embodiment of the invention;

FIG. 14C depicts small loops 1655 on backing material 1650, in accordance with an embodiment of the invention;

FIG. 14D depicts large loops 1655 on backing material 1650, in accordance with an embodiment of the invention;

FIG. 14E depicts loops with a first orientation 1655 on backing material 1650 and loops with a second orientation 2489 on the same backing material 1650, in accordance with an embodiment of the invention;

FIG. 15A depicts a scrubbing brush 3097 with hooks 1660 on one face, in accordance with an embodiment of the invention;

FIG. 15B depicts a scrubbing brush 3097 with loops 1655 on one face, in accordance with an embodiment of the invention. The face may include a patch which can comprise either hooks or loops (see FIGS. 15A and 15B) or both hooks and loops on the one face, in accordance with an embodiment of the invention;

FIG. 15C depicts a scrubbing brush 3097 with hooks 1660 on one face and loops 1655 on the opposite face, in accordance with an embodiment of the invention;

DETAILED DESCRIPTION OF THE INVENTION

Definitions

Figures 1A, 1B, 1C:
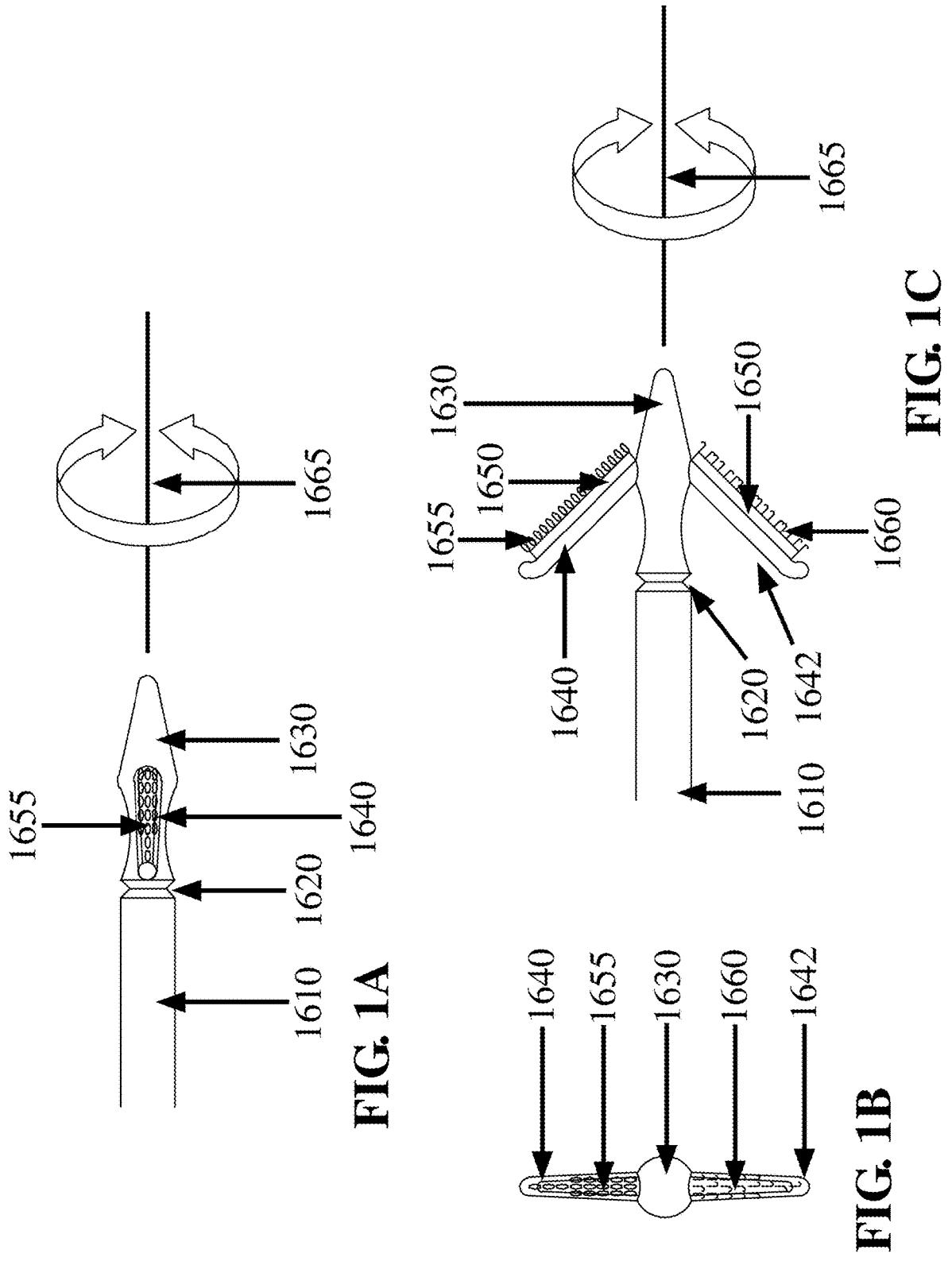
FIG. 1A shows a side view of a propeller FTSC device 1630 attached to a rigid handle 1610 with an etched groove 1620 allowing for detachment, with one blade visible 1640, in accordance with an embodiment of the invention.
FIG. 1B shows a frontal view (i.e., along longitudinal axis 1665 of FIG. 1A of a propeller FTSC device with two blades visible (1640, 1642), where a first surface on a first blade 1642 presents hooks 1660 and acts to frictionally abrade a tissue surfaces while a second surface on a second separate blade 1640 which is not in contact with the first surface presents loops 1655 and acts to collect the tissue and cell sample that has been abraded at least in part by the first surface, in accordance with an embodiment of the invention.
FIG. 1C shows a side view of a propeller FTSC device rotated ninety (90) degrees about the longitudinal axis 1665 (not shown) from the position shown in FIG. 16A, with two blades visible (1640, 1642), where a first surface on a first blade 1642 presents hooks and acts to frictionally abrade a tissue surfaces while a second surface on a second separate blade 1640 which is not in contact with the first surface presents loops 1655 and acts to collect the tissue and cell sample that has been abraded at least in part by the first surface, in accordance with an embodiment of the invention.

The transitional term 'comprising' is synonymous with 'including', 'containing', or 'characterized by', is inclusive or open-ended and does not exclude additional, unrecited elements or method steps. The transitional phrase 'consisting of' excludes any element, step, or ingredient not specified in the claim, but does not exclude additional components or steps that are unrelated to the invention such as impurities ordinarily associated with a composition. The transitional phrase 'consisting essentially of' limits the scope of a claim to the specified materials or steps and those that do not materially affect the basic and novel characteristic(s) of the claimed invention.

As used herein 'Velcro' refers to the hook portion of VELCRO® hook and loop fasteners (Velcro BVBA, U.K.). As used herein 'Kylon' refers to fenestrated loops (with sickle-shaped candy cane ends) as disclosed herein (KYLON®, Histologics LLC, Anaheim, CA) and 'Kylon material' refers to the fenestrated loops and short arm (generated by fenestrating an attached loop) each woven in a fabric base. A fabric base includes a woven nylon strip, a woven nylon area, a plastic strip, a plastic area, and a GORE-TEX® (W. L. Gore and Associates, Newark, DE) strip or area. A loop can be attached to the fabric base by weaving (i.e., a woven fenestrated loop), thermal bonding, light activated bonding, chemical bonding or other methods well known in the art.

As used herein, the term 'abrasive material' means a fiber, spatula, and or hook that is able to separate a tissue fragment from an epithelial layer. For example an abrasive material can include but is not limited to 'toothbrush' bristle brush type design, cytology spatula, cytology broom, twisted strands of metal wire, twisted strands of plastic fibers, steel wool, corrugated plastic, Velcro® hooks and Kylon® fenestrated loops. The term 'hook material comprising an abrasive' means a hook material as disclosed herein suitable for abrading tissue to provide a tissue and/or cell sample. As used here the term 'fenestrated loop' refers to a hooked, 'candy-cane' shape formed by severing a loop, wherein a short, hooked end is less than approximately 50% of the length of the loop, e.g., Kylon® fenestrated loops. In some embodiments, a fenestrated loop is formed by severing a loop once, leaving a short arm adjacent to the fenestrated loop. A 'hook' is a structure with two ends with a curved shape in which the two ends do not cross, or meet, and one end is not connected to the other end, where one end of a 'hook' is curved or bent back at an angle for abrading or serrating contacted tissue. As used herein, the phrase 'hook array' means three (3) or more hooks where each hook is within a distance of at least one (1) other hook, where the distance results in a density of between approximately 50 loops per square inch to approximately 1000 loops per square inch. In this instance, approximately means plus or minus twenty (20) percent.

A 'loop' is a structure with two ends with a curved shape in which the two ends either cross, meet, or one end is connected to the other end, where the loop is curved for catching and holding tissue fragments. The terms 'collector material', 'loop array', or 'loop device comprising a collection device' means a plurality of loops extending approximately perpendicular or at an angle from a sheet, a fabric, or woven material, where the plurality of loops are positioned on a device to allow collection of tissue fragments. In this instance, approximately means plus or minus twenty (20) percent. That is the plurality of loops extend approximately perpendicular plus or minus twenty (20) degrees (i.e., the angle can be in a range of between seventy (70) degrees and to one hundred and ten (110) degrees). A collection device can collect cells in addition to tissue fragments. The loops can vary in shape and diameter. A collector material can include one or more fenestrated loops in what is otherwise an array of loops, i.e., a collector material with only loops can with time accumulate one or more fenestrated loops due to wear and tear, sterilization and handling. A collector material including one or more fenestrated loops in an array of loops remains a collector material provided it retains a significant number of loops and the loops are able to retain tissue fragments (e.g., a single platform finger cot with an area of both fenestrated loops 1660 and intact loops 1655 comprises both an abrasive material and a collector material, see FIG. 11C and FIG. 11D. As used herein, the phrase 'loop array' means three (3) or more loops where each loop is within a distance of at least one (1) other loop, where the distance results in a density of between approximately 50 loops per square inch to approximately 1000 loops per square inch. In this instance, approximately means plus or minus twenty (20) percent. In various embodiments of the invention, a loop array can be positioned either adjacent to or opposite to a hook array (see FIG. 6A, FIG. 6B, FIG. 6D, FIG. 7A, FIG. 7B, FIG. 11C and FIG. 11D.

A 'finger cot', a 'covered finger' or a 'gloved finger' means a medical supply used to cover one finger. A 'glove' means a medical supply used to cover two or more fingers.

A 'histological sample' means a fragment of tissue spanning two or more endothelial layers of the tissue. A histological sample requires an abrasive material in order to dislodge the sample. In contrast, a cytological sample includes cells that are sloughed from a tissue surface.

The term 'palmar' refers in the usual and customary manner to the fingerprint side of a finger. As used herein the term finger is synonymous with the term thumb. The phrase 'distal palmar aspect' refers in the usual and customary manner to the distal phalange of the palmar aspect. The term 'dorsal' in the context of a finger, refers in the usual and customary manner to the fingernail side of a finger. The phrase 'side of a finger' and the like refer to the aspect of a finger between the palmar and the dorsal aspects, including the distal phalange and/or the intermediate phalange. The phrase 'proximal palmar aspect' refers in the usual and customary manner to the fingerprint side of the intermediate phalange of a finger and/or extending towards the proximal phalange.

The term 'fenestration' means an opening created in a loop to form a 'hook'. The terms 'paddle' or 'blade' refer to a surface upon which abrasive material and/or collector material can be attached. Both a 'paddle' and a 'blade' can have two or more locations upon which either abrasive material and/or collector material can be disposed, see e.g., FIG. 4B and FIG. 4C where collector material 1655 and abrasive material 1660 are each located around approximately forty (40) degrees (included angle) of the circular profile of the columnar paddle (where the collector material 1655 and the abrasive material 1660 are symmetrically opposed on opposite aspects of the circular profile). In various embodiments of the invention, the included angle of the collector material 1655 is larger than the included angle of the abrasive material 1660. In various embodiments of the invention, the included angle of the collector material 1655 is smaller than the included angle of the abrasive material 1660. In various embodiments of the invention, the included angle of the collector material 1655 and the included angle of the abrasive material 1660 can be non-overlapping (i.e., collector material is not in contact with the abrasive material), contiguous (i.e., collector material is adjacent to the abrasive material) and or overlapping (i.e., collector material is interdispersed with the abrasive material). A location side of a 'paddle' or a 'blade' is smooth means that contact between the smooth side and a tissue surface does not result in abrasion of the tissue surface. A 'propeller' refers to a device with two or more 'paddles' or 'blades', where each of the two or more 'paddles' or 'blades' each have two sides.

A 'propeller FTSC device' refers to a rigid head with two (2) or more blades (1640, 1642) projecting from a shaft 1610 or central body 1630, see e.g., FIGS. 1A-1C. A tapered FTSC biopsy device refers to a rigid head 1630 attached to a shaft 1610, the rigid head 1630 having two (2) or more surfaces including hooks 1660 and/or loops 1655; see e.g., FIGS. 2A-2C. The propeller FTSC can have a central nose cone 1622 that can also have one or more surfaces including 1660 and/or loops 1655. With prior FTSC devices, the aim is to dislodge both tissue and cells from the target, and sweep them both into the hooks. There is much less cellular material in the hooked fabric than what can be swept into the flocked fabric loops 1655, which act like a 'mop'. The term covered finger FTSC biopsy device refers to a finger cot 1875 (e.g., covering one or more fingers or even a glove) which presents facets including 1660 and/or loops 1655; see e.g., FIGS. 3A-3C. The term 'capsule FTSC biopsy device' 1980 refers to a rigid head attached to a shaft 1610, the rigid head 1980 having a generally spherocylindrical shape which includes patches of hooks 1660 and/or loops 1655; see e.g., FIGS. 4A-4C.

Figures 6A, 6B:
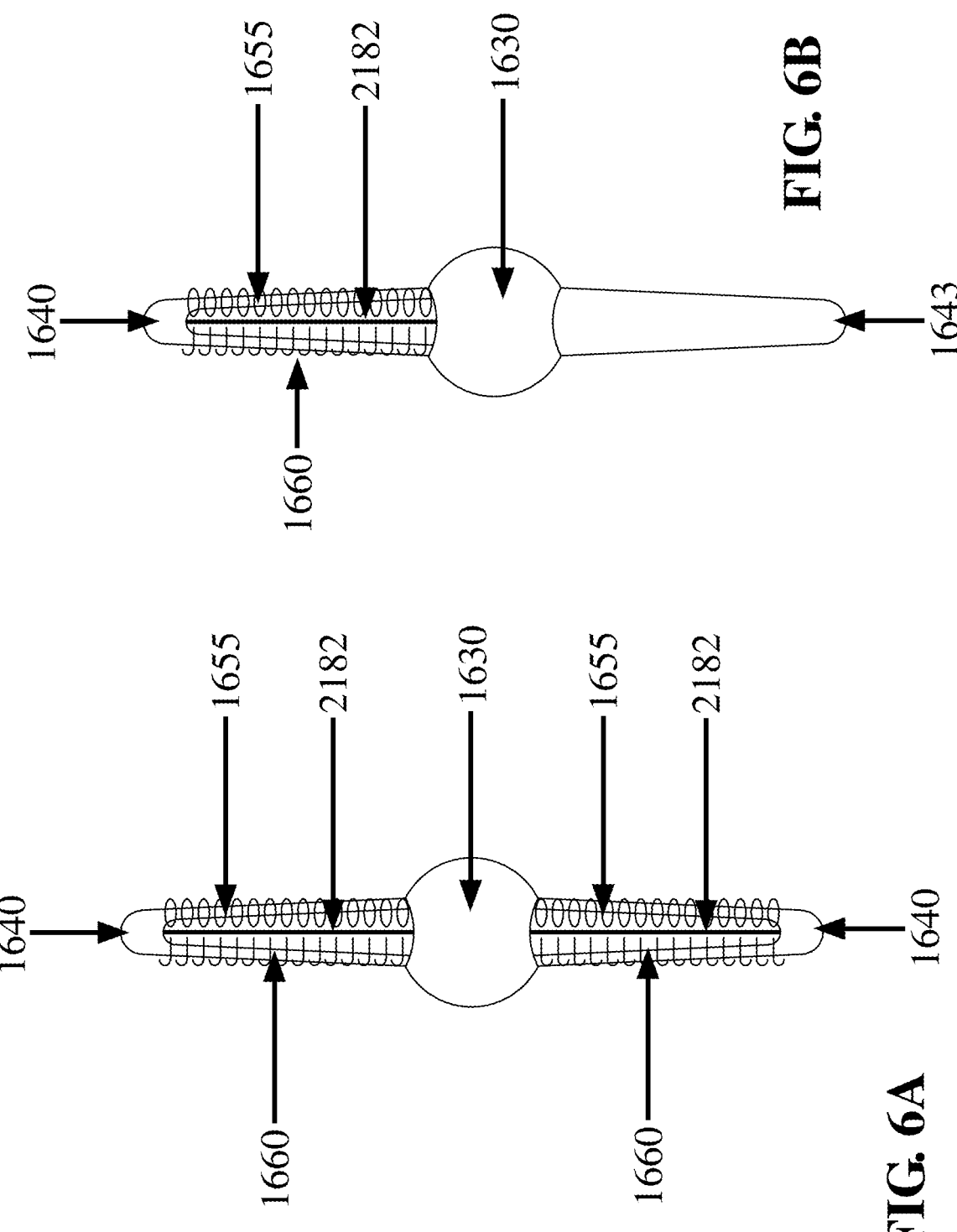
FIG. 6A is a variation on FIG. 1B, wherein where each sampling propeller blade 1640 emanating from the nose cone 1630 of the FTSC device is split along the local long axis into two (2) sections, one with hooks 1660 on one side and loops 1655 on the other side, and having a vertical gap 2182 in between the hooks 1660 and loops 1655, in accordance with an embodiment of the invention.
FIG. 6B is a variation on FIG. 1B, where one sampling propeller blade 1640 emanating from the nose cone 1630 of the FTSC device is split along the local long axis into two (2) sections, one with hooks 1660 on one side and loops 1655 on the other side, and having a vertical gap 2182 in between the hooks 1660 and loops 1655, and a smooth (non sampling) propeller blade 1643, in accordance with an embodiment of the invention.

The term 'local long axis' means, in the usual and customary sense, the long axis of an individual blade or paddle disposed in an FTSC device, see e.g., the plurality of hooks and loops are separated along the local long axis in FIG. 6. In FIG. 6A and FIG. 6B anticlockwise rotation of the propeller allows the upper arm blade's abrasive material 1660 to dislodge tissue fragments and the upper arm blade's collector material 1655 (i.e., on the same blade) to collect tissue fragments (and or the lower arm blade's collector material 1655), or the lower arm blade's abrasive material 1660 to dislodge tissue fragments and the lower arm blade's collector material 1655 (i.e., on the same blade) to collect tissue fragments (and or the upper arm blade's collector material 1655). In FIG. 6 abrasive material 1660 and collector material 1655 are contiguous (i.e., adjacent) such that the upper arm blade contains both an abrasive material 1660 and a collector material 1655. The term 'local short axis' means, in the usual and customary sense, the short axis of an individual blade or paddle disposed in an FTSC device, see e.g., the plurality of hooks and loops are separated along the local short axis in FIG. 7. The phrase 'an area of separation between the hook material and the loop material lies approximately parallel to a long axis of the finger cot' means that a line passing through the area of separation is approximately parallel to the local long axis. In FIG. 7 abrasive material 1660 and collector material 1655 are contiguous (i.e., adjacent) such that both the upper arm blade and the lower arm blade contain both an abrasive material 1660 and a collector material 1655.

The term 'histological sampling' or 'histological sample' means, in the usual and customary sense, the obtaining of an intact tissue including cell and biopsy tissue suitable for histological analysis. The term 'histological information' means, the information obtained from a histological sample e.g., morphological features, diseased tissue and identification of microscopic structures. Accordingly, a histological sample is also suitable for cytological analysis. The term 'molecular sampling' or 'molecular sample' means, the obtaining of a sample suitable for DNA, RNA, and/or proteomic analysis. The term 'molecular information' means, the information obtained from a molecular sample e.g., DNA sequence information, RNA sequence information, and/or proteomic analysis information. The term 'cytological sampling' or cytological sample' means, in the usual and customary sense, the obtaining of cells suitable for cytological analysis. For example, a common application of cytopathology is the Pap smear, a screening tool used to detect precancerous cervical lesions that may lead to cervical cancer. The phrase 'orifice of the uterus' means in the usual and customary sense the OS (ostium of uterus) cavity which makes up part of the cervical canal.

A propeller blade divided along the local long axis is disclosed in e.g., FIG. 6. The propeller blade is attached to a central body or nose cone of the propeller.

Unless expressly indicated to the contrary, the term 'FTSC device' is synonymous with the term 'FTSC biopsy device'.

A 'facet' is a surface that is cut into the head of a biopsy device, where the surface's contour differs from the contour of the head of the biopsy device. The term 'facet' is used in analogy to a facet of a gem, where the gem facet has a surface contour that differs from the other surface contours of the other facets of the gem. A facet that is cut at an angle of 30 degrees relative to the major axis of the head of the biopsy device is equivalent to a 'point' cut in a gem that can produce one side of an octahedron. A facet that is cut at an angle of 3-9 degrees relative to the major axis of the head of the biopsy device can be thought of as equivalent to one of the 30 odd cuts in a gem's crown to produce a 'brilliant'. In contrast to the facet of a gem which is flat, the facet cut in the head of a biopsy device can have a concave or convex surface contour. That is a flat facet of a biopsy device has neither a positive nor a negative radius of curvature. A convex facet of a biopsy device has a positive radius of curvature relative to the flat facet. A concave facet of a biopsy device has a negative radius of curvature relative to the flat facet. The curvature of a cylinder or rod will be referred to as positive in contrast to the negative curvature of a concave facet cut into the cylinder or rod. The curvature of a convex facet cut into the cylinder or rod will be referred to as positive.

An 'applicator' is a surface upon which at least an abrasive material is applied and which can be contacted to a tissue surface. An 'applicator' includes a surface upon which a collector material is applied. In an embodiment of the invention, a finger cot covering a finger can be an applicator. The abrasive material can be associated with the applicator at any angle relative to the main axis of the applicator. The collector material can be associated with the applicator at any angle relative to the main axis of the applicator. The abrasive material and the collector material can be associated with the applicator at different angles relative to the main axis of the applicator. In an embodiment of the invention, the main axis of a finger cot covering a finger is the direction of the finger when extended and pointing.

The maximum overall diameter of a FTSC device with one facet is the sum of the maximum diameter of the head and the length of the abrasive material attached to the facet. The overall diameter of a FTSC device at a point on the one facet is the sum of the diameter of the head at that point and the length of the abrasive material attached to the facet.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes.

Systems and methods in accordance with embodiments of the present invention can provide for improved presentation and interaction with digital content and representations of digital content. Representation as used herein includes, but is not limited to, any visual and/or audible presentation of digital content. By way of a non-limiting example, digital images, web pages, digital documents, digital audio, and other suitable content can have corresponding representations of their underlying content. Moreover, interfaces such as graphical user interfaces can have corresponding representations of their underlying content.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

In an embodiment of the present invention, the FTSC head sampling surface takes on the shape of the site to be sampled. In an analogy to a key designed to fit a lock, where the key can be duplicated by making an impression of the key in clay and then duplicating the shape left in the clay; the FTSC head can be shaped to fit the contour of a particular sampling area. In an embodiment of the invention, the FTSC head is intended to sample from the area of the cervix most at risk for a neoplastic transformation. In an embodiment of the invention, by adjusting the surface of the FTSC head, the FTSC head can sample the transformation zone. In an embodiment of the invention, by adjusting the surface of the FTSC head, the FTSC head can sample the exocervix.

In various embodiments of the present invention, the FTSC device and the fabric are made of materials such that the hooks of the fabric can be secured to the base or facet of the device. In an embodiment of the present invention, the device and the fabric are made of materials that allow the fabric to be ultrasonically welded to the device. In an embodiment of the present invention, the device and the loops are made of the same materials and the loop can be ultrasonically welded to the device. For example, nylon loops can be ultrasonically welded to a nylon facet implanted in the curette. Alternatively, nylon loops can be ultrasonically welded to a nylon curette head on the facet. In another embodiment of the present invention, the hooks can be extruded through injection molding during the process of injection molding the curette. In an alternative embodiment of the present invention, the hooks of the fabric can be attached to the device using an adhesive. For example, an ultra violet (UV) light activated adhesive can be used to affix the fabric to the device. A railing can be introduced onto the facet of the device and the UV light activated adhesive can be placed within the confines of the dam made by the railing. In an embodiment of the invention, the railing allows sufficient adhesive to be retained in the dam so that hooks are bound to the facet. Using a railing and adhesive to adhere the loop array adjacent or opposite to the hook array decreased the amount of hooks/loops that were shed or broken off from the FTSC head during sampling. In this manner, the railing and the ability to dam the adhesive so that the adhesive bound individual hooks and loops to the facet increased the amount of tissue retained using the FTSC sampling head.

The fabric pad can then be moved towards the adhesive containing facet on the pad backing allowing the pad to be recessed into the cavity created by the marginal glue dam. The use of the UV light activated adhesive was observed to also stabilize the loop array adjacent or opposite to the hook array in the fabric, reducing the risk of detachment of the hooks/loops and thereby the particulate matter shedding during clinical use.

A biopsy can resolve the causative agent in many if not all of the lesions that are formed from viral, bacterial, fungal or protozoa infections. In the case of HSV, the sample must include cells, not just fluid from the blister, since the virus is in the skin cells of the blister or ulcer. The sample from a lesion or blister collected during an acute outbreak can be used to identify the agent based on the growth of the virus or substances related to the virus.

Plex ID™ is a high-throughput system based on polymerase chain reaction (PCR) and mass spectrometry analysis to enable identification of pathogens within six to eight hours. Plex ID™ can detect and characterize a broad range of microorganisms in a given sample, including viruses, bacteria and fungi. Although Plex ID™ is not currently intended for use in diagnostic procedures, it is available for use in unregulated areas such as epidemiologic surveillance, biological research, environmental testing, and forensic research. Plex ID™ has been shown to detect viral isolates from adenovirus, alphavirus, enterovirus, flavivirus, HSV and human parvovirus B19 with a limit of detection ranging from 15 to 125 copies.

Focal Biopsy

In various embodiments of the present invention, a trans-epithelial FTSC device can be used to perform biopsies of lesions suspected of harboring disease. Clinicians are used to a rotational soft bristle brush to collect endocervical cytology. This soft bristle brush is rotated, with the soft bristles removing superficial cells. When a deeper biopsy is required after an abnormal pap smear or to evaluate the cause of vaginal bleeding, clinicians currently use a sharp edge curette. A sharp edge curette is not designed to and customarily is not rotated to obtain a biopsy. Instead, it is repeatedly inserted, then withdrawn against the canal beginning at a reference point., As the cervix is cylindrical with a circlular face, the clinician typically starts at a reference point, usually 12:00 o'clock position, and shift, rotating to all positions around the clock, sequentially back and forth rotated as it is pushed in and pulled back. A clinician may use the sharp curette, most commonly the Kevorkian curette, and scrapes the cervical OS cavity surface to accumulate cells. The to and from scraping motion shears epithelium and cells which lie free in the canal and are later collected, as the curette is not also designed to collect the majority of tissue harvested. The procedure with the Kevorkian curette is both painful and can cause trauma to the cervix, as it shaves and detaches the epithelium from the underlying stroma.

Currently, a clinician can choose an exo-cervical FTSC or an endo-cervical FTSC biopsy tool. In an embodiment of the invention, a clinician can choose a hybrid exo-cervical/endo-cervical FTSC screening biopsy tool. In an embodiment of the invention, the clinician fits the cylinder of the hybrid exo-cervical/endo-cervical screening biopsy tool projecting from the larger disk into the cervical OS cavity. In an embodiment of the invention, the surface of one or both the facet present on the cylinder and the face of the disc contact one or both the squamo-columnar junction and the endo-cervical columnar epithelium. In an embodiment of the invention, the disc can have a diameter of approximately 35 mm. In an alternative embodiment of the invention, the disc can have a diameter of approximately 25 mm. In an embodiment of the invention, the cylinder can have a diameter of approximately 9 mm. In an embodiment of the invention, the cylinder can have a diameter of approximately 6 mm. In an embodiment of the invention, the cylinder can have a diameter of approximately 3 mm.

In an embodiment of the invention, a lesional biopsy site sampled with the FTSC device can be no larger than approximately 3 mm in diameter. In an alternative embodiment of the invention, a lesional biopsy site sampled by the FTSC device can be no larger than approximately 6 mm in diameter. In another embodiment of the invention, a lesional biopsy site sampled by the FTSC device can be no larger than approximately 10 mm in diameter. In an embodiment of the invention, a lesional biopsy site sampled by the FTSC device can be no larger than the diameter of the FTSC device head at a position 4 mm distal from the tip. In an alternative embodiment of the invention, a lesional biopsy site sampled by the FTSC device can be no larger than the diameter of the FTSC device head at a position 9 mm distal from the tip. In an embodiment of the invention, a lesional biopsy site sampled by the FTSC device can be no larger than a focal biopsy.

In an embodiment of the invention, lesions are accessible to an examiner during routine examination. In an alternative embodiment of the invention, lesions are not accessible to an examiner during routine examination. In another embodiment of the invention, access to lesions requires surgery. In an embodiment of the invention, the tissue surface to be sampled is accessible following entry into a body cavity through a natural orifice, canal, or surgical channel. In an embodiment of the invention, the tissue surface to be sampled is accessible following entry into a body cavity via a trochar using an endoscope with a biopsy port for inspection. In another embodiment of the invention, the tissue surface to be sampled is accessible following entry into a body cavity via a cannula. In another alternative embodiment of the invention, the tissue surface to be sampled is accessible following entry into a body cavity via an arthroscope, colonoscope, sigmoidoscope, sinus scope and anoscope.

In an embodiment of the present invention, the FTSC device head remains on the lesion due to the design of the device surface. In an embodiment of the present invention, the FTSC device head remains on the immediate area of intended biopsy/therapy due to the design of the device surface. In an embodiment of the present invention, the FTSC head has a facet with a fabric for functionally abrading epithelial surfaces including a backing material and a plurality of fenestrated loops attached to the backing material adhered to the facet. In an embodiment of the present invention, the FTSC head facet has a flat surface. In an alternative embodiment of the present invention, the FTSC head facet has a concave surface. In another alternative embodiment of the present invention, the FTSC head has a facet with a convex surface. The concave facet head allows a handle attached to the head to be rotated and ensures that the head remains on the desired location for convex tissue surfaces. The convex facet head allows a handle attached to the head to be rotated and ensures that the head remains on the desired location for concave tissue surfaces. The flat facet head with an adhered abrasive fabric allows the hand to be rotated and pressed completely without allowing gaps between the abrasion material and the surface tissue to be sampled when collecting a biopsy. In an embodiment of the invention, the head of the FTSC device is conical and pointed. In an embodiment of the invention, the head of the FTSC device is elliptical and pointed. In an embodiment of the invention, the head of the FTSC device is multifaceted and pointed.

In clinical trials of a number of FTSC devices, undertaken to test various prototype geometries, a pointed-tip rod with the loop array adjacent or opposite to the hook array enabled the clinician to more easily dilate the cervix, while not increasing the risk of damage to the cervix through an incision. In an embodiment of the invention, the diameter of the head of the FTSC device is a maximum of approximately 8 mm and tapers to a tip of less than approximately 1 mm. In an embodiment of the invention, the diameter of the head of the FTSC device is a maximum of approximately 5 mm and tapers to a tip of less than approximately 1 mm. In an embodiment of the invention, the diameter of the head of the FTSC device is a maximum of approximately 4 mm and tapers to a tip of less than approximately 0.8 mm. In an embodiment of the invention, the diameter of the head of the FTSC device is a maximum of approximately 3 mm and tapers to a tip of less than approximately 0.6 mm. In an embodiment of the invention, the diameter of the head of the FTSC device is a maximum of less than approximately 3 mm and tapers to a tip of less than approximately 0.6 mm.

In clinical testing, the 'sharpened pencil' like design with one flat face, was found to be too rounded or thick toward the middle of the pad for entry into the endocervix in some women with smaller canals. A thinner more streamline profile flattens and narrows the diameter as the circular shape becomes more elliptical or oval, without becoming too flat or spear-like in nature. A profile that was too flat can enhance the 'cutting' or shearing ability of the tip when it is pushed into the endocervix and a laceration from the edges can result.

Buccal sampling can be accomplished with an embodiment of the FTSC device. Table 1 is a list of materials and models to abrade off cells and/or tissue for FTSC abrasion devices. Table 1 is also a list of materials and models to collect cells and/or tissue for FTSC abrasion devices. In Table 1, materials which do not covalently bind the constituents of the sample, e.g., agarose, cellulose, dextran, steel wool, Velcro, Kylon, glass fiber, cat tongue, or polyacrylamide, or materials that reversible bind the constituents of the sample, e.g., CM-cellulose, heparin-agarose, heparin-sepharose, Q-sepharose, sepharose 4B, and illustra sephadex G-25, illustra sephadex G-50, and illustra sephadex G-100 agarose gels (GE Healthcare Life Sciences, Uppsala, Sweden) are preferred over absorbent surfaces such as cotton, powders, toothpicks, cuttlefish bone, sterile pads, pumice, sponges, loofah, cotton swabs or aerator stones. Surfaces with reversible binding substrates are swollen in an aqueous solution and can also be washed with Morpholino-Ethane Sulfonate buffer (MES) prior to use as a collector. Genomic DNA can be released from a sepharose collector using a heparin solution in a concentration dependent manner. In an alternative embodiment of the invention, NaCl and/or ethanol can be used to elute the genomic DNA from the collector in a step wise fashion. A flat paddle FTSC or capsule shaped device can be used to sample the inside of the mouth. The paddle or capsule can recess along the buccal mucosa or prior to removal, plating, nucleic acid amplification, hybridization and/or sequencing. In an alternative embodiment of the invention, the cells collected on the FTSC device can be transferred to a formalin free preservative for stabilizing the cells prior to nucleic acid amplification, hybridization and/or sequencing. One formalin free solution is a SCP solution (Streck Inc. Omaha, Nebr.) diluted 1:1 with phosphate buffered saline solution. In another alternative embodiment of the invention, the cells collected on the FTSC device can be transferred to a DNAGUARD® solution (BioMatrica, San Diego, CA) which rapidly permeates cell membranes at ambient temperature to stabilize and protect genomic DNA within the cells or tissue prior to nucleic acid amplification, hybridization and/or sequencing. Anal-rectal sampling can be accomplished with an embodiment of the FTSC device. A finger cot with the abrasive located on the dorsal side allows the practitioner to feel the oral, anal or rectal mucosa and underlying structures such as the male prostate with only the material of the glove between the gland and the examiner's palmar region of the finger, while still allowing the practitioner to rotate his finger one hundred and eighty degrees and thereby use the dorsal side to take a cell or tissue sample of the gland. Most oral, anal or rectal cancers are detected using the gloved finger palpation method, and the added advantage of simultaneous tissue sampling for laboratory pathological analysis is significant. Furthermore, with simultaneous pressure and rotation of the tissues with a smooth and abrasive side around the fingertip, it will allow for easier rotation in the canal as opposed to a dual frictional surface (ventral and dorsal) where rotation will meet resistance. It is theorized that simultaneous application of the device's abrasive and smooth surface dampens the sensation of pain within the anal canal, oral cavity, or other mucosal canal like cavities. Sampling of local excision specimens suspicious for a cutaneous malignant melanoma or carcinoma can be undertaken using an embodiment of the FTSC device. The trumpet tipped device with a round facet would be optimal for flat surfaces, while the tapered device diamond shaped facet device would be optimal for lesions inside body surface tunnels, cavities, or canal structures.

TABLE 1

| List of Alternative Materials and Models for FTSC devices. | |
| --- | --- |
| Abrade/collect | Materials/Tools |
| Hooks | steel wool gauze, steel wool pad, metal mesh scouring pad, plastic mesh scouring pad, Velcro, Kylon, hook and loop, glass fiber, cat gut, rayon, nylon, or other types of abrasive put on a flexible backing |
| Scraper or File Tools | Metal or plastic blades, file molded out of plastic material, toothpick, two pronged tool, one to break layer one with pad to absorb, triangular shaped wire loop, dental scraper, dental burr, regular burr, fresnel lens like instrument (fine molded ridges), plastic helix, file made out of cuttlefish bone, sintered glass, aerator stone |
| Brushes | radial DREMEL ® brush, bristle brush, bristles that poke out slightly (similar to 5 o'clock shadow or a light beard) |
| Other | pumice, sponges, loofah, sterile pads, file, cotton swab with salt, shark skin, powder/abrasive |
| Absorbents | SEPHAROSE ® coated reversible absorbent fibers, dextrane coated reversible absorbent fibers, small absorbent coated pads, chemical process (weak acids). | between gum and buccal mucosa and permit insertion withdrawal or rotation within the space. This is akin to insertion, withdrawal, or rotation of a lollipop. The cells collected on the FTSC device can be stabilized in a ten (10) percent neutral buffered formalin solution. In another embodiment of the invention, the cells collected on the FTSC device can be rapidly frozen on the FTSC device to −80° C. and thawed In clinical trials it was observed that an FTSC device with a maximum diameter of less than approximately 8 mm which tapered to a tip of less than approximately 1 mm enabled the clinician to insert the FTSC device including a loop array adjacent or opposite to a hook array into almost any cervical canal, and then gently press to insert the FTSC device further into the cervical os. In many cases, the insertion also dialated the cervix to allow entry of the device deeper into the canal. This is because the FTSC device head is a smooth tapered tip which acts like a dilator. That is because the distal approximately 10 mm (corresponding to approximately one-half the length of the facet) of the FTSC device head is a smooth tapered tip it acts like a dilator. That is because the distal approximately 13 mm (corresponding to approximately two-thirds the length of the facet) of the FTSC device head is a smooth tapered tip it acts like a dilator. It was further observed that an FTSC device including a loop array adjacent or opposite to a hook array can be used to both dilate the cervical OS cavity and enter the cervix. The thinner pointed FTSC device including a loop array adjacent or opposite to a hook array did not significantly increase the risk of damage to the cervix by causing an incision or inadvertant puncture of collateral tissue.

In various embodiments of the invention, the pointed thin head of the FTSC device has one or more facet surfaces cut into the pointed tip to increase the area sampled in a longitudinal direction along the rod main axis. In an embodiment of the invention, the major axis of the facet surface is parallel with the major axis of the rod. In an embodiment of the invention, the minor axis of the facet surface is parallel with the major axis of the rod. In an embodiment of the invention, the one or more facet surfaces are at the distal end of the rod. In an embodiment of the invention, the widest portion of one or more of the one or more facet surfaces is at the distal end of the rod. In an alternative embodiment of the invention, the thinest portion of one or more of the one or more facet surfaces is at the distal end of the rod. In an embodiment of the invention, one or more of the one or more facets have a concave surface. In an embodiment of the invention, one or more of the one or more facets have a convex surface.

In an embodiment of the invention, one or more of the one or more facet surfaces are diamond shaped. In an embodiment of the invention, one or more of the one or more facet surfaces are pear shaped. In an embodiment of the invention, one or more of the one or more facet surfaces are triangle shaped. In an embodiment of the invention, one or more of the one or more facet surfaces are hybrid triangle-pear-shape. In an embodiment of the invention, one or more of the one or more facet surfaces are hybrid diamond-pear-shape. The hybrid diamond-pear shaped facet surface with the diamond end distal to the handle enhances the pointed feature of the FTSC head, while the pear shaped end proximal to the handle increases surface area. Due to the tapered fit of the device into the canal orifice, the canal itself steadies the device as it is rotated, where pressure can be applied maximally to the fabric surface during rotation.

In an embodiment of the invention, the distal surface of the FTSC thin head has abrasive material attached. In an alternative embodiment of the invention, abrasive material is associated with the surface of the FTSC pointed thin head. In another embodiment of the invention, one facet surface of the FTSC pointed thin head has abrasive material adhered to the surface. In an embodiment of the invention, one or more of the one or more facet surfaces of the FTSC pointed thin head has abrasive material applied. In another alternative embodiment of the invention, two or more facet surfaces of the FTSC pointed thin head have abrasive material applied.

In an embodiment of the invention, the length of the facet on the FTSC device tip is approximately 19 mm long. In an embodiment of the invention, one or more of the one or more facet surfaces begins at the tip of the FTSC device head and extends towards the handle. In an embodiment of the invention, the diameter of the FTSC head 4 mm distal from the facet tip is approximately 2 mm. In an embodiment of the invention, the diameter of the head 9 mm distal from the facet tip is approximately 2.5 mm. In an embodiment of the invention, the diameter of the head 12 mm distal from the facet tip is 3 mm.

In an embodiment of the invention, the maximum overall diameter of a FTSC device with one facet is the sum of the maximum diameter of the head and the length of the abrasive material attached to the facet. In an embodiment of the invention, the overall diameter of a FTSC device at a point with one facet is the sum of the diameter of the head at that point and the length of the abrasive material attached to the facet.

The abrasive material comprises fenestrated loops that have a short hook end, wherein the distance from the top of the loop to the bottom of the hook is less than approximately 50% of the length of the loop. The abrasive material comprises fenestrated loops that are approximately 4 mm in length. In this embodiment of the invention, the maximum overall diameter of a FTSC device with maximum diameter 3 mm and one facet is 7 mm. The abrasive material fenestrated loops are approximately 3.5 mm in length. The maximum overall diameter of a FTSC device with maximum diameter 3 mm and one facet is 6.5 mm.

In a FTSC device with maximum diameter 3 mm and with abrasive material including fenestrated loops that are approximately 3 mm in length, if the distal 4 mm of the FTSC head is inserted then the FTSC device tip including the abrasive material has a diameter at this point (4 mm distal from the tip) of approximately 5 mm. In an embodiment of the invention, the diameter of the head greatly facilitates access into the cervical os. In this embodiment, the cervix needs be dilated less than approximately 5 mm in order for the distal 4 mm of the facet of the FTSC device to enter the cervical cavity. It has been found that some cervical OS cavity diameters are 1-2 mm at the entry point. In this embodiment, the cervix needs be dilated less than approximately 3 mm in order for the distal 4 mm of the facet of the FTSC device to enter the cervical cavity at the entry point with minimal bending of the abrasive material fenestrated loops.

In another embodiment of the invention, a FTSC device with maximum diameter 3 mm and with abrasive material including fenestrated loops that are approximately 3.5 mm in length, if the distal 4 mm of the FTSC head is inserted then the FTSC device tip including the abrasive material has a diameter at this point (4 mm distal from the tip) of approximately 5.5 mm. In this embodiment, the cervix needs be dilated less than approximately 3.5 mm in order for the distal 4 mm of the facet of the FTSC device to enter the cervical cavity. While the Kylon material hooks deform and bend somewhat and can be squeezed down tightly with a very tight fit, they lose their ability to abrade if the hooks remain perpendicular, rather than parallel to the canal mucosal surface. The hooks are intentionally designed to be angular and face away from the mucosal surface, as not to penetrate or lacerate primarily, but to shear and frictionally abrade with rotational torque.

It was noted that when in-vitro post-hysterectomy cervical tissue was sampled with Velcro that the hooks are too close to the fabric backing not allowing the hook tips sufficient contact to cause abrasion in a biopsy setting. In contrast, it was noted that when in-vitro post-hysterectomy cervical tissue was sampled with a FTSC head including a loop array adjacent or opposite to a hook array that the hooks are sufficiently disal from the fabric backing to allow the hook tips sufficient contact to cause abrasion and the loops to collect the tissue in a biopsy setting. The longer hooks and more distally cut fenestrations did permit frictional abrasion and tissue buckling and fracture. The array of loops provided adequate tissue sample collection for processing, analysis, and diagnosis.

In an embodiment of the invention, once the thin tapered FTSC device is inserted into the cervix, only the distal 4 mm of the facet corresponding to three to five hooks of the Kylon material need to be inside the canal to obtain sufficient material for a biopsy requiring fifteen (15) to fifty (50) copies of DNA. In an alternative embodiment of the invention, once the thin tapered FTSC device is inserted into the cervix, only the distal 9 mm of the facet corresponding to ten (10) to twenty (20) hooks need to be inside the canal to obtain material for a biopsy requiring approximately 100-200 copies of DNA. In another embodiment of the invention, once the thin tapered FTSC device is inserted into the cervix, only the distal 12 mm of the facet corresponding to thirty (30) to forty (40) hooks need to be inside the canal to obtain material for a biopsy requiring approximately 300-500 copies of DNA. Unlike conventional curettage, the FTSC head device can be rotated and the hooks can contact the OS cavity and frictionally abrade, circumferentially being pressed against the endocervical epithelium, while being pressed and rotated. Since the Kylon material has a greater propensity to 'hold' the tissue, more tissue is available for pathological analysis. This improves the diagnostic probability of determining the causitive agent. Importantly, tissue yield is crucial when scanning pre-cancerous lesions.

A prototype FTSC cone-shaped device tip with no facet and a maximum overall diameter of 9 mm (maximum diameter of head was 3 mm extending to the tip of approximately 1 mm diameter) was found not to fit inside a number of stenotic OS cavities even after dilation of the cervix. The prototype FTSC cone-shaped device tip was wrapped with Kylon material applied 360 degrees around the device. This added approximately 6 mm (twice the length of the fenestrated loops) to the maximum diameter of the head. The overall diameter at a point 4 mm distal from the tip was 8 mm. Similarly, the rectangular Kevorkian curette was found not to fit into most stenotic OS cavities.

In an embodiment of the invention, the FTSC device head is a round or trumpet shaped cylinder. The facet can be flat, concave, or covex in shape. This provides one or more concave facet surfaces at the distal end of a disc or disc-like protrusion without a tapered end. The one or more concave surfaces allow the FTSC device to be placed on a specific location on a body surface, such as the exocervix, vagnia, buccal mucosa, anal mucosa, perianal skin, or vulva and rotated without moving off the desired location. A convex sampling head best conforms to a concave tissue surface smilar to a 'lock in key' nature. A concave sampling head best conforms to a convex tissue surface similar to a 'lock in key' nature. A flat tissue surface is best sampled by a flat sampling surface, eliminating gaps between the sampling surface and the epithelium. In an embodiment of the invention, the ability of the FTSC device to remain on a fixed location can allow improved sampling of epithelial tissue from the lesion. Because the FTSC device does not move off the lesion, it allows increased rotation of the FTSC device, which in turn ensures a frictional abrading to enable improved sampling. In contrast, other methods disclosed in prior art do not disclose, teach or suggest that the position from which the biopsy is sampled is to be visually located, guided and retained through the choice of the facet surface contour. The FTSC device captures surface and exfoliated cells through frictional abrading of the target tissue site without affecting the ability of the fabric hooks, arranged in rows which permit channels, to open and close, capturing and retaining tissue into those channels and the fabric body.

Regional Biopsy

In various embodiments of the invention, the FTSC device can be used to remove a tissue biopsy, cytologically sample, and screen large geographic areas of tissue at risk for disease. In an embodiment of the invention, the FTSC device can be used to sample cells or biopsy and screen neoplastic transformation such as, but not limited to, the squamo-columnar junction of the female cervix in the presence or absence of visualized lesions. In an embodiment of the invention, the FTSC device by providing one or more concave surfaces on an otherwise conical or rod-like protrusion, allows the device to be placed on a specific location and rotated without moving off the desired location. In an embodiment of the invention, the ability to remain on a fixed location can provide samples of epithelial tissue from specific locations for analysis. In this manner, the overall surface can be randomly sampled with a finite number of biopsy samples. In contrast, other methods disclosed in prior art do not allow the position from which the biopsy is to be sampled to be localized. The intent is to frictionally remove cells and tissue from a variety of localized positions based on visual evidence of the larger area, or knowledge of the 'at-risk' landmark area where disease is likely to evolve or be harbored, such as the 'transformation zone' of the cervix, which can range from approximately 10-40 mm in diameter.

Simultaneous Biopsy of Epithelial Surfaces and Canal-Like Structures

In an embodiment of the invention, the surface of the head has abrasive material applied. In alternative embodiments, the device has a head with material applied that contains a central core of fenestrated loops that are longer (e.g., approximately 4-7 mm long), surrounded by a wider rim of shorter fenestrated loops (e.g., approximately 3 mm in length). The longer fenestrated loops are geometrically suited to insinuate within a central canal structure, such as the endocervical canal of the cervix. There is simultaneously uniform contact of the fenestrated loop fibers circumferentially around the endocervical canal on the flat exocervical surface. With rotation and agitation in a back-and-forth motion using a brush, cells and tissue can be used to harvest within the fenestrated loop channels. In an embodiment of the invention, the abrasive material can be the Kylon material fabric. Because the tissue is held by the Kylon material fabric, when the FTSC head is sent to the pathologist, the pathologist can require a tool to remove the tissue from the FTSC head. Unlike bristle brushes that are twisted, Kylon material fabric hooks are arranged in rows. In contrast to Velcro material, the hooks are shallow, and the fenstrations distal and narrow, thus the Kylon can be combed, and the tissue collected in the biopsy can be combed out. In an embodiment of the invention, a miniature mustache comb can be used to remove the tissue from the Kylon material fabric. The technician has to comb the tissue directly out from the Kylon material fabric into the vial of liquid fixative. Then the vial of fixative containing the mixed tissue can be trapped on a filter paper. Alternatively, in an embodiment of the invention, the tissue can be teased free from the hooks of the Kylon material fabric using a scalpel or tweezers. In an embodiment of the invention, the hooks of the Kylon material fabric can be cut or sheared to remove the tissue from the fabric base for the biopsy. In an embodiment of the invention, the abrasive material can be dissolved in an appropriate solvent to remove the tissue from the abrasive material for the biopsy. In an embodiment of the invention, the tissue can be rinsed forcefully from the abrasive material on to the filter paper or collection vessel.

In an alternative embodiment of the invention, approximately 9 mm long central fibers are surrounded by approximately 3 mm fibers. In an embodiment of the invention, the device can be inserted into the cervix and rotated with spinning revolutions. Following frictional trans-epithelial tissue disruption, the head containing biopsy sample can be detached and inserted into a liquid vial of fixative.

Frictional Tissue Sampling and Collection Biopsy Devices

In an embodiment of the invention, the frictional tissue sampling and collection biopsy devices disclosed herein utilize Kylon material, a fabric that includes minute plastic (e.g., nylon) fiber hooks (loops that are fenestrated) at a minimal distance from the apex of the loop. The fenestrated loops flex but do not fracture under minimal to moderate force, or separate under pressure.

The semi-rigid fenestrated loops can be pressed in a rotational manner (e.g., in sweeping or circular motion) away from or toward the clinician, perpendicular, or at an angle into epithelial tissue surfaces. The semi-rigid fenestrated loops remain flexible enough to cause separation of the fenestrated ends, creating frictional forces sufficient to cause local heating and buckling of the epithelial surface away from the underlying stroma. The loops are fenestrated such that with applied pressure they are flexible enough to open and provide access to a 'collection well' for histological fragments. The tips of the fiber hooks are oriented away from the tissue. On pressing and rotation across the tissue surface, the fibers scrape, buckle and shear the epithelium from the underlying stroma. The fragments are excoriated from the tissue surface through the concomitant application of frictional forces applied to the tissue surfaces by the fenestrated loops. The frictional forces overcome the adhesive and binding forces of the tissue below to release fragments of various shapes and size, all eligible for collection in a histology lab, and subsequent processing and analysis.

The semi-rigid fenestrated loops (e.g., made of nylon) hold the tissue fragments after excoriation because the fenestrated loops are elastic enough to sufficiently re-close and capture the removed tissue. In addition, the spaces between the fibers also retain excoriated tissue. The frictional forces exceed the binding forces afforded by adhesion molecules which anchor epithelia to the basement membrane, as well as disrupting Van der Waals forces.

Once the epithelium is frictionally sheared from the underlying stroma, the tissue clumps and epithelial fragments are swept and excavated by the distal most curved apex of the loop and entrapped within the geometrically suited spaces between the closed, fenestrated loops. Thus, the method is frictional abrasion, excavation via rotation and other directional motion, and tissue collection within inter-loop channels. In an embodiment the rotation is clockwise such that the abrasive material passes over the epithelial surface, followed by the collector material. In an alternative embodiment the rotation is counter-clockwise such that the abrasive material passes over the epithelial surface, followed by the collector material.

The Kylon material fabric can be cut into uniform shapes such as a hybrid diamond-pear shape, a pear shape, a circular disc or straight edge shape(s) and with uniform height, allowing the device to provide 360-degree coverage of tissue surfaces over suspected lesions, without a gap within the circumference of the device. The Kylon base material is also flexible to allow the material to be applied to a concave or covex surface. This is in distinction to bristle brushes which are spiral or bent in shape, which present surface gaps. This does not allow uniform contact with the target tissue, and gaps and spiral or irregular orientation to tissue, that when pressed, agitated, or rotated penetrate the tissue surface causing a traction point, which can cause migration of the device from the lesion site toward the direction of rotation when such devices are pressed onto lesions and rotated or moved for tissue harvesting.

Following biopsy, the head of the device is readily severed from the handle to allow the head to be deposited in a liquid fixative agent. In an embodiment of the invention, the handle material is scored (thus weakened) near the head to allow the head to be broken off from the handle and deposited in liquid fixative, which is usually formaldehyde or alcohol. The Kylon material fabric, fibers, and/or device head (all with the tissue entrapped between the fibers) are removed from the vial of liquid fixative to remove the tissue from the head of the device and process it for analysis. Therefore, one may intentionally design the device in an embodiment in which the user can easily decouple the device head from the device shaft. For example, some embodiments can have the shaft inserted into the head via a clip or screw thread mechanism, a key-in-lock design with a pressure release button, or a luer-lock type of attachment. Once the biopsy is obtained, the head and handle/shaft parts can be de-coupled, wherein the handle can be discarded, or sterilized and re-used, and the head immersed in a vial of fixative.

Some methods for removal of tissue from the fiber assembly include using a brush, rinsing under pressure, immersion and agitation manually or mechanically, or by sonication. Alternatively, the fibers can be sheared from the fabric on telfa or other filter paper, and the fibers plucked off the paper leaving the entire biopsy specimen. Alternatively, after tissue is collected into the device channels, tissue can be deposited via rotation or agitation in a vial of liquid fixative, rinsed off the device under pressurized spraying, or removed from the nylon fibers by cutting away the nylon fibers from the fabric (e.g., onto filter paper), thus leaving the tissue on the paper, which can be immersed in fixative.

The Kylon material fabric fibers of the preferred embodiments, are manufactured as described in U.S. Pat. No. 8,652,067 ('Frictional Trans-Epithelial Tissue Disruption and Collection Apparatus and Method of Inducing and/or Augmenting an Immune Response', Inventor Neal M. Lonky et al.).

Preferred embodiments of abrasive material comprise minute plastic fenestrated loops that are pressed perpendicular or at an angle into epithelial tissue surfaces which, upon rotational or agitational pressure forces, cause tissue epithelial fragments to be frictionally separated from the underlying tissue basement membrane and stroma. The channels between the fenestrated loops entrap and collect the tissue fragments. The process is similar to curettage with a blunt curved tool, which also scrapes, shears and strips epithelium from the underlying stroma of target tissues. On the other hand, the process is in contrast to sharp curettage where the purposefully sharp edge of the curette first incises, pierces, then shaves and scoops epithelium and underlying stroma from the tissue surface. The process described herein is less perceptible to patients than conventional biopsies and causes a smaller amount of blood loss and trauma.

In an embodiment, the present invention relates to a frictional trans-epithelial tissue apparatus. In various embodiments, the apparatus comprises approximately 3 mm or smaller fenestrated loops adherent to and projecting perpendicular from a surface, with a density of approximately 50-1000 loops per square inch, evenly spaced or arranged in rows. The loops can be fenestrated at the center or at their lateral aspect to allow for added flexibility and constructed from plastic, metal, or another stiff material. The rounded end of the loop is opposite the surface.

Fenestrated loops can be of sufficient flexibility to withstand frictional forces and not fracture, and of sufficient tensile strength to generate sufficient frictional shear force during a sweeping or circular motion of the device to remove epithelium from tissue. The space between clumnps of fenestrated loops 191 (see FIG. 18B) can serve to capture and harbor the sampled tissue.

In various embodiments designed for focal lesional biopsy, a flat, flexible surface, which anchors the fenestrated loops, can be approximately 10-15 mm, but is most practically approximately 5-10 mm in diameter and circular in shape. In alternative embodiments of the present invention, a concave surface anchors the Kylon material fenestrated loops. The shape can be another geometrical design if it affords an advantage in covering the target tissue area for sampling. The head can be hinged in such a way that it can be folded or compressed, inserted through a small endoscopic channel, and then reinstated to its original state with a sampling surface. It can be comprised of plastic, cloth, or another composite material. The fenestrated loops can be threaded through and project away from the head towards the tissue surface. In various embodiments of the present invention, a hub fiber or 'pin' that penetrates and anchors the center of the disc on the target biopsy area, can serve as a central post to rotate the disc around for stability.

In other embodiments intended to screen larger, regional tissue sites at risk for neoplastic transformation or other disease process, the shape can be circular, where the diameter can range from approximately 10-50 mm, and the loops can project at varied distances from the head towards the tissue surface. For the purpose of histological screening to detect cervical neoplasia, the central approximately 5 mm diameter disc projects longer (approximately 5-25 mm) loops, and can be surrounded circumferentially by the aforementioned approximately 3-23 mm long fenestrated loop fibers. Upon pressure and rotation or agitation, the endocervical and exocervical tissues can be simultaneously frictionally sheared and collected by the loops. Histological screening can be necessary to correctly reflect the presence or absence of epithelial pathology, because adhesion molecules can prevent representative exfoliation from diseased tissue in some cases, leaving cytological screening methods lacking in accuracy.

Preferably, a frictional trans-epithelial biopsy sample is taken from a lesion or an anatomical region that is predisposed to disease.

In various embodiments of the present invention, the device includes a plastic, metal, or mixed composition disk or curved convex head, which provides a flat surface for a cylinder to be attached. The disk can be equal or greater in diameter than the cylinder. The disk is approximately 5-10 mm in length while the flat, concave or convex cylinder is less than approximately 3 mm in thickness.

In various embodiments of the present invention, the applicator probe can be comprised of a rod or cylindrical shape including any suitable material (e.g., wood, glass, plastic, paper or metal), which has the base, surface and loop unit at its most distal end, wherein the applicator probe is approximately 2-5 mm in diameter and approximately 15-30 cm in length. It is constructed larger or smaller depending on the access to the tissue surface. The shaft of the rod or cylindrical shaped applicator probe can be rigid or semi-rigid so as to not bow or arc when pressure is transmitted from the handle to the device head.

A handle into which the applicator probe can be transfixed is optionally mechanical, providing motorized rotational, drill-like movement or agitating vibration.

The device handle can be composed of stiff material, preferably plastic similar to Lucite, clear or opaque in coloration, rigid nylon plastic, or alternatively can be glass, wood or metal. The device head can take a variety of shapes, cylindrical or tapered in design, but the distal most surface face is circular, square, or polygonal, and can be composed of plastic (e.g., nylon). The device head diameter can range from approximately 5-50 mm. The abrasive material fabric can be welded to the nylon surface ultrasonically, or can alternatively be attached via adhesive, or via a rim or collar (e.g., which snaps on to the surface into a recess in the head of the device).

In some embodiments, the clinician examines tissue surfaces and chooses an area to be sampled based on the presence of a suspicious lesion. In other embodiments, the clinician chooses an anatomical landmark known to be 'at risk' for neoplastic or disease transformation for the purposes of sampling the entire chosen surface. The new learning is that a deeper trans-epithlial biopsy grade sample can be obtained with a minimally invasive approach with minor discomfort or trauma. Thus far, in 15 cases in a prospective clinical trial, patients report the biopsy procedure using Kylon biopsy material on the described applicator(s) induces little or no discomfort, with minor bleeding graded less than conventional curette or sharp biopsy devices.

The handle or applicator probe is grasped at its proximal end or handle. The distal portion or head of the device contains the base, surface and loops that project perpendicular from the base towards the tissue surface with the more rounded ends that are pressed against the tissue surface.

With moderate pressure, the examiner simultaneously presses and rotates the device against the tissue several times in a clockwise or counterclockwise direction, or agiating motion in alternating 75-120 degree rotations, clockwise and counter clockwise. These actions cause an opening or separating the fenestrated loops, thus performing frictional disruption of the tissue surface. Alternatively, a sweeping motion can be used. If a motorized handle is used, it can be activated to assist in the rotation or vibration of the device.

The harvested tissue is collected from the tissue surface, and some tissue already trapped in the loops themselves can be inspected and can be teased from the loops, or the loops transected from the fabric and separated, and the remaining tissue placed in a fixative solution.

The frictional tissue sampling and collection device can be used on any body surface, both external to the body, body cavities, or on internal organs. To access epithelial surfaces of internal body organs, the device head can be deflated, folded or collapsed to pass through a small aperture or port, and re-opened or expanded to fully expose the fabric to the biopsy surface. This device can be used on humans or any other living organism with an epithelial surface. Any tissue surface can be sampled. The ease of use in each case can be related to the strength of the individual tissue adhesion and binding forces in specific locations. The loops themselves can serve as tissue collection reservoirs for later storage once placed in a fixative medium. The platform with the loops can be detached from any applicator for later examination and processing (i.e., decoupled from the instrument used to press against tissue surfaces to obtain the tissue sample).

If the tissue surface is a canal or concave shaped area of the body, instead of a perpendicular platform design, the loops are directly attached to the probe itself, which is gradually tapered at the end to facilitate insertion into the canal. The hooks and the loops project perpendicularly from the probe surface at its distal end, and the unit, once placed into the canal that is lined on its surface with epithelium, contacts such epithelium snugly.

The hooks and the loops can be mounted on the platform or project from the rim surface of the platform, perpendicular or at an angle to the platform along the margin of the platform, or attached to other delivery applicators, or surgical instruments. The 'platform' means a surface of any shape or size which can be placed on a tissue surface. The platform can include at least a first side and a second side. When a platform includes a single sampling surface, the main axis of the platform extends outwardly perpendicular to the single sampling surface (see FIGS. 9, 12, 14, 15, and 18). When a platform includes two sampling surfaces that are opposite each other (i.e., approximately 180 degrees rotationally removed), then approximately 180 degrees rotation around the main axis of the platform interchanges the position of the first side and the second side (see FIG. 1 to FIG. 4, FIG. 6A, FIG. 7, and FIG. 19). The platform can include a finger cot 2593 (see FIG. 10). Further, the finger cot 2593 can include more than one platform (see FIG. 11A, FIG. 11B, and FIG. 11E-11L). The base assembly can be any shape or size, can be permanently rigid or collapsible, and can include a medical examiner's gloved finger supporting a finger cot, where the finger cot is used for sampling. A person of ordinary skill in the art would understand from these principles that a finger cot can include more than one axis of rotation for each platform.

If the tissue surface lies within a canal-shaped tissue surface, the hooks and the loops can be attached directly to the applicator probe, which can be inserted into the canal-shaped body cavity. The probe with the hooks and the loops projecting from the surface and contacting the epithelium is rotated, causing the frictional disruption sampling and tissue collection from the tissue surface. The shape of the probe can be constructed in any shape that allows a snug fit into the canal. The loops 115 can be arranged in rows or equally spaced 181 (see FIG. 18B), allowing for maximal contact and tissue collection. In an embodiment of the invention, an array of loops contain channels, where the loops 115 are separated by a distance 181 between a lower limit of approximately $10^4$ meter and an upper limit of approximately $10^{-3}$ meter. In this range, approximately means plus or minus twenty percent (20%).

Some embodiments of the invention comprise a motorized mechanical assistance via a mechanical handle into which the most proximal end of the applicator probe is inserted. Such mechanical assistance can enhance the rotational or vibratory force that the device transmits to the tissue after contact is established. This can increase the frictional forces and the speed of the tissue disruption/sampling and shorten the procedure time.

In another embodiment there is provided an FTSC device having novel frictional transepithelial tissue disruption and sample collection utility. With reference to FIGS. 1A-1C, the embodiment provides an elongated handle member (1610) which terminates at a groove (1620) allowing for attachment/detachment of a terminal head assembly having central body 1630. Torque about axis 1665 can be applied to disrupt tissue in contact with the FTCS device. Accordingly, attachment point 1620 can be configured to prevent local rotation such that torque applied at handle 1610 is transmitted through the entire length of the FTCS device. Eminating from the central body 1630 are a plurality, preferably two (2), of frictional transepithelial tissue disruption and sampling surfaces adhered to blades 1640 (i.e., 'propeller blades' or structures). Because these sampling surfaces radiate outward from the longitudinal axis 1665 in a manner resembling a propeller blade, this embodiment can to referred to as a 'propeller' embodiment. The frictional transepithelial tissue disruption and sampling surfaces can eminate from central body 1630 at any angle with respect to longitudinal axis 1665, e.g., about 10, 15, 20, 25, 30, 35, 40, 45, 50, 55, 60, 65, 70, 75, 80, 85, 90 degrees. In embodiments, the frictional transepithelial tissue disruption and sampling surfaces can project from central body 1630 at greater than 90 degrees. With reference to FIG. 1E, the embodiment provides an elongated handle member (1610) which terminates at a groove (1620) allowing for attachment/detachment of a terminal head assembly having central body 1630 and propeller blades 1640 that emanate from closer to the nose cone 1622. With reference to FIGS. 1D and 1F, the embodiment provides an elongated handle member (1610) which terminates at a groove (1620) allowing for attachment/detachment of a terminal head assembly having central body 1630 and propeller blades 1640 and an additional patch of hooks With reference to FIG. 1E, the embodiment provides an elongated handle member (1610) which terminates at a groove (1620) allowing for attachment/detachment of a terminal head assembly having central body 1630 and propeller blades 1640 an an additional patch of hooks 1660 on the nose cone. The frictional transepithelial tissue disruption and sampling surfaces and of FIGS. 1A-1F can include hooks 1660 and/or loops 1655 as described herein, which can be adhered to the body of the propeller blade 1640 or the nose cone 1622 by a backing (e.g., adhesive) layer 1650. The backing layer 1650 can be a fabric or an adhesive fabric. As disclosed herein, hooks 1660 are useful for disrupting tissue in preparation for sample collection. Loops 1655 are useful for collecting samples of tissue and cells. Accordingly, hooks 1660 on a first surface of a propeller blade 1642 can disrupt (i.e., 'scape') tissue from a site of interest, and loops 1655 on a second surface of a propeller blade 1640 can collect (i.e., 'sweep') the scraped site to collect the dislodged tissue and cells for subsequent analysis. In an embodiment of the invention, the proximal face of both the first surface and second surface presents neither hooks nor loops, but rather are smooth. In an embodiment of the invention, the distal face of either the first surface or the second surface presents neither hooks nor loops, but rather is smooth. Accordingly, the term 'smooth distal aspect' and the like refer in this context to a surface which does not abrade or otherwise remove tissue and/or cells and does not collect tissue and/or cells. In an embodiment of the invention, by rotating the propeller FTSC device with a smooth blade and an abrasive collection blade a patient experiences less discomfort as the abrasive interaction is interspaced with a smooth sensation which relaxes the nerve cells present in the epithelial location being sampled. The nose cone of the propeller can also be coated with intact or fenestrated loops for tissue abrasion and collection.

In another embodiment depicted e.g., in FIGS. 2A-2C, the central body and 'propeller blades' disclosed in FIGS. 1A-1C are replaced with a cone shaped feature 1770 where the small end of the conical taper is distal from handle 1610. Positioned on the conical taper between the distal end and the groove 1620 are two (2) or more frictional transepithelial tissue disruption and sampling surfaces. In an embodiment of the invention, the two or more regions of frictional transepithelial tissue disruption and sampling surfaces include loops 1655 and hooks 1660. In an embodiment of the invention, there are at least two (2) frictional transepithelial tissue disruption and sampling surfaces. FIGS. 2A-2C can includes hooks and/or loops as described herein, which can be adhered to the cone shaped feature 1770 by a backing (e.g., adhesive) layer 1650. The backing layer 1650 can be a fabric or an adhesive fabric. Features common to FIGS. 1A-1C and FIGS. 2A-2C are indicated with the same feature index number. In an alternative embodiment of the present invention, the loops 1655 and hooks 1660 can each be affixed to a facet. The facet can have a different radius of curvature to the cone shaped feature 1770.

Figures 3A, 3B, 3C:
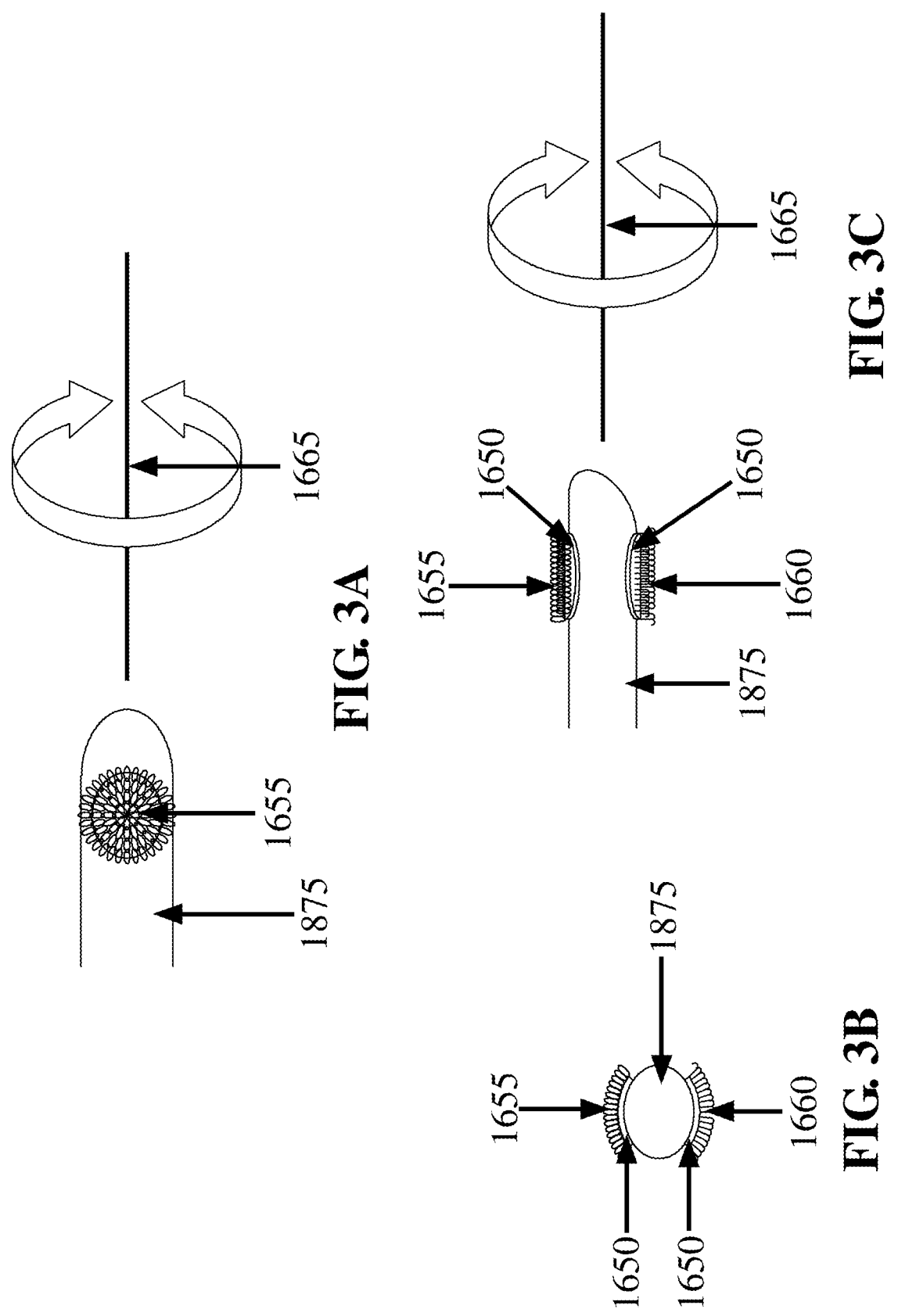
FIG. 3A shows a side view of a covered finger FTSC biopsy device or finger cot 1875 with one surface presenting loops 1655 visible, in accordance with an embodiment of the invention.
FIG. 3B shows a frontal view (i.e., view along the longitudinal axis 1665) of a covered finger FTSC biopsy device or finger cot 1875 with backing material 1650 of two surfaces visible, where a first surface presents hooks 1660 and acts to frictionally abrade a tissue surface while a second surface which is not in contact with the first surface presents loops 1655 and acts to collect the tissue and cell sample that has been abraded at least in part by the first surface, in accordance with an embodiment of the invention.
FIG. 3C shows a side view of a covered finger FTSC biopsy device or finger cot 1875 rotated ninety (90) degrees about the longitudinal axis 1665 from the position shown in FIG. 3A, with two surfaces visible, where a first surface presents hooks 1660 and acts to frictionally abrade a tissue surface while a second surface which is not in contact with the first surface presents loops 1655 and acts to collect the tissue and cell sample that has been abraded at least in part by the first surface, in accordance with an embodiment of the invention.

In another embodiment of the present invention, there is provided a covered finger biopsy device; see FIGS. 3A-3C. A finger covering 1875 is provided, as e.g., a finger cot, a gloved finger, a two (2) finger finger cot, a finger cot which extends to more than two (2) finger, and the like. The long axis of the finger is indicated as feature 1665. Toward the distal end of finger covering 1875 can be positioned one or more regions of frictional transepithelial tissue disruption and sampling surfaces. In an embodiment of the present invention, a frictional transepithelial tissue disruption surface is a loop feature 1655. In an embodiment of the invention, a sampling surface is a hook feature 1660. In an embodiment of the invention, a loop feature 1655 is disposed at the palmar (i.e., fingerprint) aspect of the finger. In an embodiment of the invention, a loop feature 1655 is disposed at the dorsal (i.e., fingernail) aspect of the finger. In an embodiment of the invention, a hook feature 1660 is disposed at the palmar aspect of the finger. In an embodiment of the invention, a hook feature 1660 is disposed at the dorsal aspect of the finger. During sampling, the finger and the finger covering 1875 can be rotated about the long axis 1665 such that transepithelial tissue is frictionally disruption by hook region 1660 (i.e., scraped) and upon further rotation of the finger, the dislodged tissue and cells can be collected at loop region 1660. FIGS. 3A-3C can includes hooks and/or loops as described herein, which can be adhered to the finger covering 1875 by a backing (e.g., adhesive) layer 1650. The backing layer 1650 can be a fabric or an adhesive fabric.

In another embodiment, the distal end of any of the FTSC devices disclosed in any of FIGS. 1A-1C, FIGS. 2A-2C, or FIGS. 3A-3C, can be replaced by a generally spherocylindical (i.e., capsule shaped) structure as shown in FIGS. 4A-4C. See e.g., feature 1980 of FIGS. 4A-4C. Moreover, feature 1980 can assume any of a variety of related shapes including, e.g., prolate spheroid, oblate spheroid, and the like. As disclosed in FIGS. 4A-4C, there are positioned along the body of 1980 one or more regions of frictional transepithelial tissue disruption (abrasive material) and one or more regions of collector material. In an embodiment of the invention, the one or more regions of abrasive material include hooks 1660 and one or more regions of collector material include loops 1655. As shown in FIG. 4B, the paddle 1980 with a circumference, a first included angle 1991, a second included angle 1992, and a main axis 1665, where the first included angle 1991 delineates a first portion of the circumference, where the second included angle 1992 delineates a second portion of the circumference. As the FTSC device is rotated about long axis 1665, transepithelial tissue is frictionally disrupted by region 1655, and upon further rotation, the dislodged tissue and cells can be collected at region 1660.

Figures 5A, 5B, 5C, 5D:
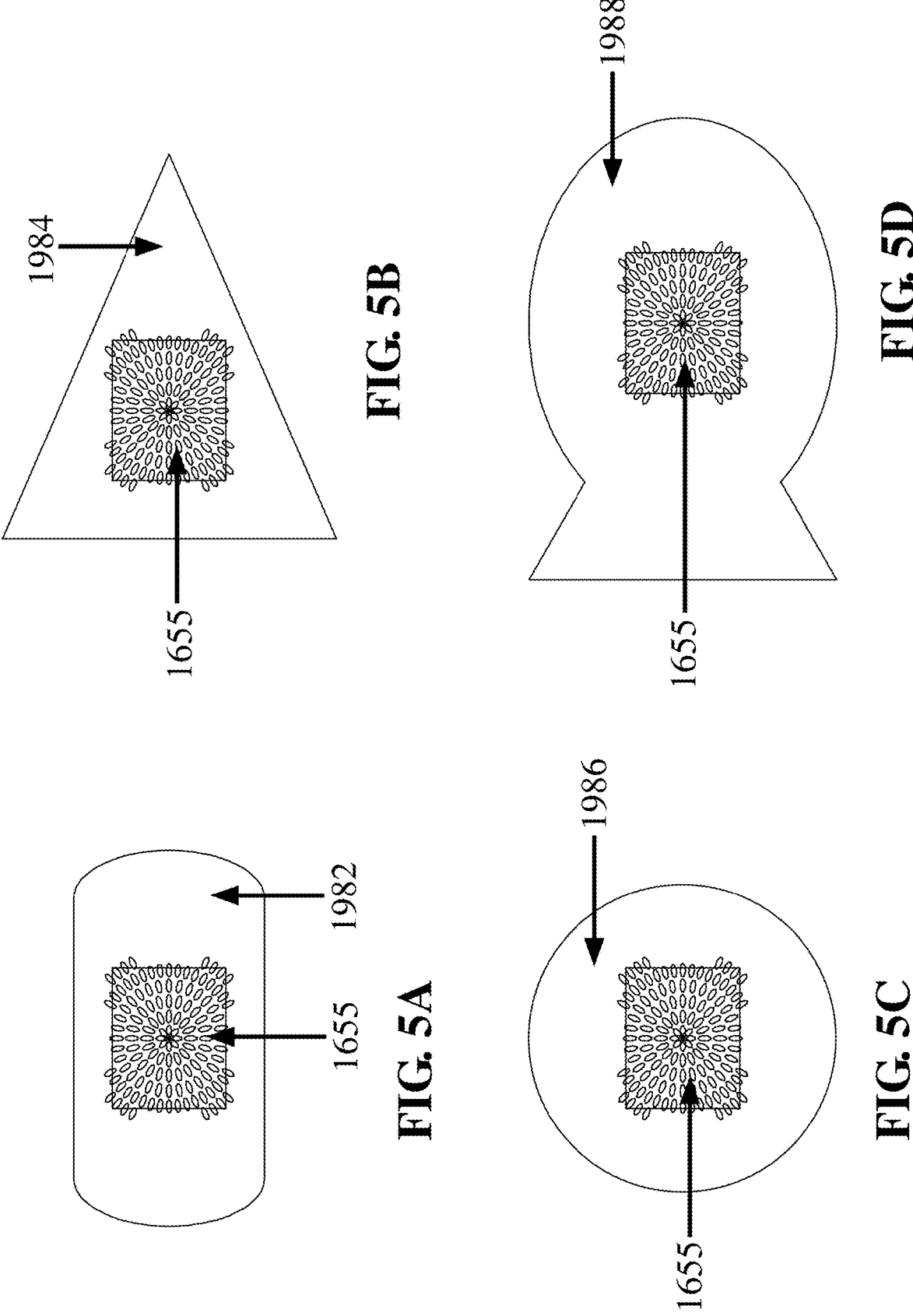
FIG. 5A depicts a flat paddle tip structure with a surface of loops 1655 on the FTSC device 1982, in accordance with an embodiment of the invention.
FIG. 5B depicts a pyramidal tip structure with a surface of loops 1655 on the FTSC device 1984, in accordance with an embodiment of the invention.
FIG. 5C depicts a round (i.e., spherical) tip structure with a surface of loops 1655 on the FTSC device 1986, in accordance with an embodiment of the invention.
FIG. 5D depicts an ichthyomorphic (i.e., fish-shaped) structure with a surface of loops 1655 on the FTSC device 1988, in accordance with an embodiment of the invention.

In other embodiments, feature 1980 disclosed e.g., in FIGS. 4A-4C, is replaced by a flat paddle 1982 tip structure (FIG. 5A), a pyramidal 1984 tip structure (FIG. 5B), a round 1986 (i.e., spherical) tip structure (FIG. 5C), and an ichthyomorphic 1988 (i.e., fish-shaped) structure (FIG. 5D). For each embodiment disclosed in FIGS. 5A-5D, there are positioned along the body of the distal region (i.e., flat paddle 1982, pyramid 1984, spherical 1986 tip or fish-shaped tip 1988) one or more regions of frictional transepithelial tissue disruption and sampling surfaces. In an embodiment of the invention, the one or more regions of frictional transepithelial tissue disruption and sampling surfaces include hooks 1660, or loops 1655, or hooks 1660 and loops 1655. As the device is rotated about long axis 1665, or translated along long axis 1665, transepithelial tissue is frictionally disrupted by the hook region 1660, and upon further rotation or translation, the dislodged tissue and cells can be collected at the loop region 1655.

In another embodiment (see FIGS. 6A-B) based on the embodiment of FIGS. 1A-1C, one or both propeller blade 1640 can be split along the local long axis into two (2) sections, one with hooks 1660 on one side and loops 1655 on the other side of the local long axis 1640, and having a vertical gap 2182 in between the hooks 1660 and loops 1655. According to this embodiment, as the device of FIGS. 6A-6B is rotated about the long axis, tissue and cells are disrupted by the hooks 1660 and subsequently collected by the loops 1655. In FIG. 6B only one propeller blade contains the hooks 1660 and loops 1655. In an embodiment of the invention, by rotating the propeller FTSC device with a smooth blade 1643 and a blade 1640 containing the hooks 1660 and loops 1655, a patient experiences less discomfort as the abrasive interaction is interspaced with a smooth sensation which relaxes the nerve cells present in the epithelial location being sampled.

Figures 7A, 7B:
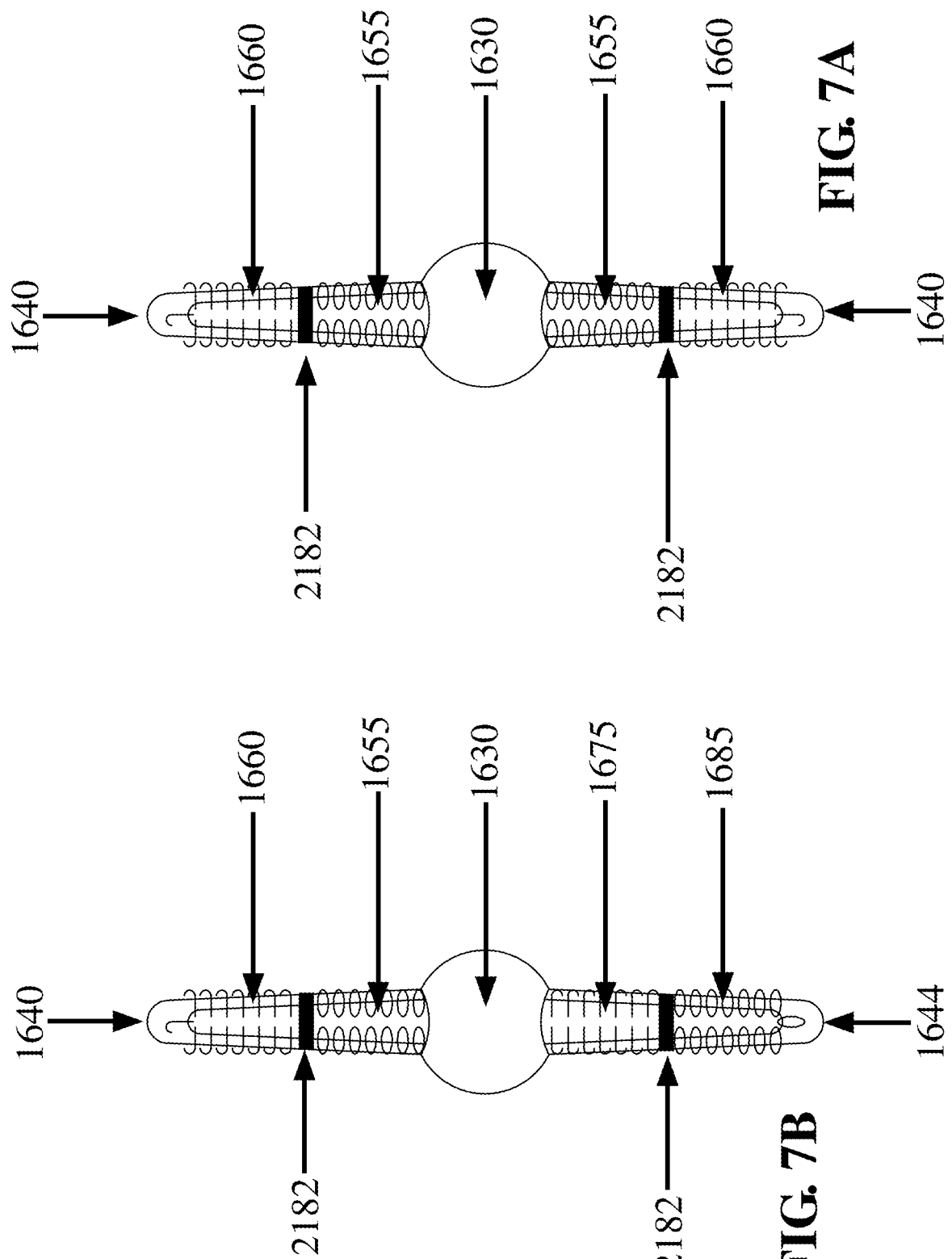
FIG. 7A is a variation on FIG. 1B, where each sampling propeller blade of the FTSC device is split into two (2) sections, one with hooks 1660 on the top section (i.e., region distal to the central feature 1630) and loops 1655 on the bottom section (i.e., region proximal to feature 1630) and a gap 2182 between the hooks 1660 and the loops 1655, in accordance with an embodiment of the invention. Accordingly, FIG. 7A can have hooks 1660 (1660 distal to 1630), gap 2182, loops 1655 (1655 proximal to 1630), central feature 1630, loops 1655=(1655 distal to 1630) gap 2182, hooks 1660=(1660 distal to 1630).
FIG. 7B is similar to FIG. 7A but with hooks 1660 (1660 distal to 1630), gap 2182, loops 1655 (1655 proximal to 1630), central feature 1630, hooks 1675 (1675 proximal to 1630), gap 2182, loops 1685, (1685 distal to 1630). That is, the bottom propeller blade of FIG. 7B has the opposite orientation of regions of hooks and loops compared with FIG. 7A (and compared with the top propeller blade), in accordance with an embodiment of the invention.

FIG. 7A is a variation on FIG. 1B, where each propeller blade 1640 of the FTSC device is split into two (2) sections, one with hooks 1660 on the top section (i.e., region distal to the central feature 1630) and loops 1655 on the bottom section (i.e., region proximal to the nose cone feature 1630) and a gap 2182 between the hooks 1660 and the loops 1655. Accordingly, FIG. 7A can have hooks 1660 (1660 distal to 1630), gap 2182, loops 1655 (1655 proximal to 1630), central feature 1630, loops 1655, (1655 proximal to 1630) gap 2182, hooks 1660 (1660 distal to 1630). FIG. 7B is similar to FIG. 7A but with hooks 1660 (1660 distal to 1630), gap 2182, loops 1655 (1655 proximal to 1630), central feature 1630, hooks 1675=(1675 proximal to 1630), gap 2182, loops 1685=(1685 distal to 1630). That is, the bottom propeller blade 1644 of FIG. 7B has the opposite orientation of regions of hooks 1675 and loops 1685 compared with the top propeller blade 1640.

In further embodiments, the local positioning of the hooks 1660 is varied to provide differently appearing fenestrations, for example FIG. 8A circles, FIG. 8B ovals, FIG. 8C zig zags, FIG. 8D squares, FIG. 8E rectangles, and FIG. 8F trapezoids. In another embodiment, fenestrations 1660 occupy regions which form one or more structures such as: circles, ovals, zig zags, squares, rectangles, or trapezoids. In another embodiment, loops 1655 occupy regions which form one or more structures such as: circles, ovals, zig zags, squares, rectangles, or trapezoids. In further embodiments, the fenestrations 1660 occupy regions which form one or more structures such as: triangle, diamond, concentric circles, half circles, polygon, waffle pattern (tire tread) or rod.

Figure 9B:
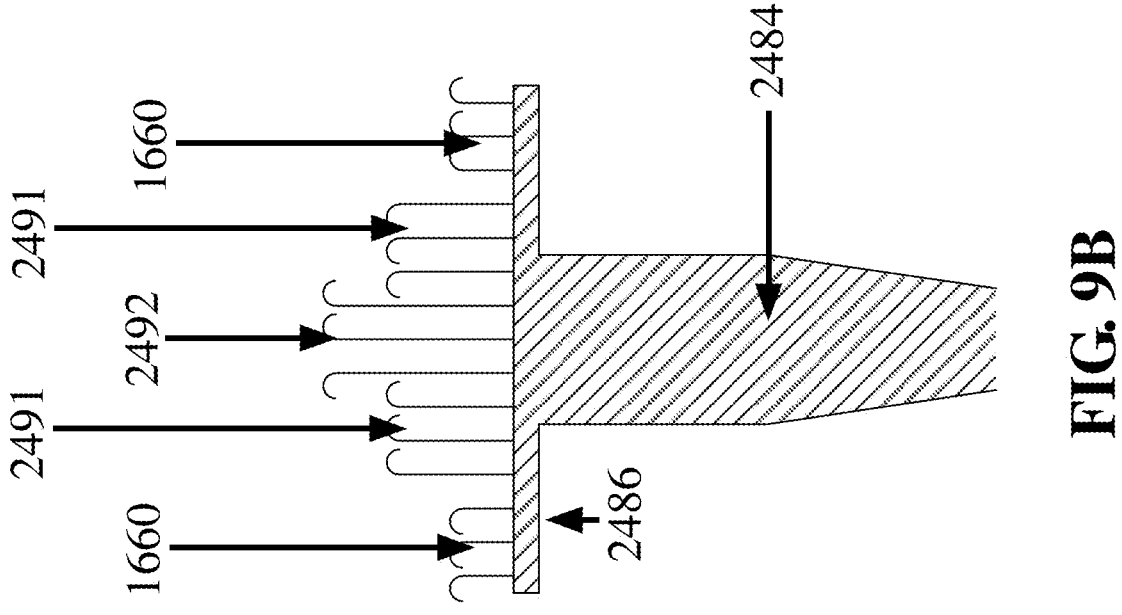
FIG. 9B is a variation of FIG. 9A where there are depicted three (3) different height hooks (1660, 2491, 2492) associated with a surface 2486 attached to a rigid handle 2484, in accordance with an embodiment of the invention.
Figure 9A:
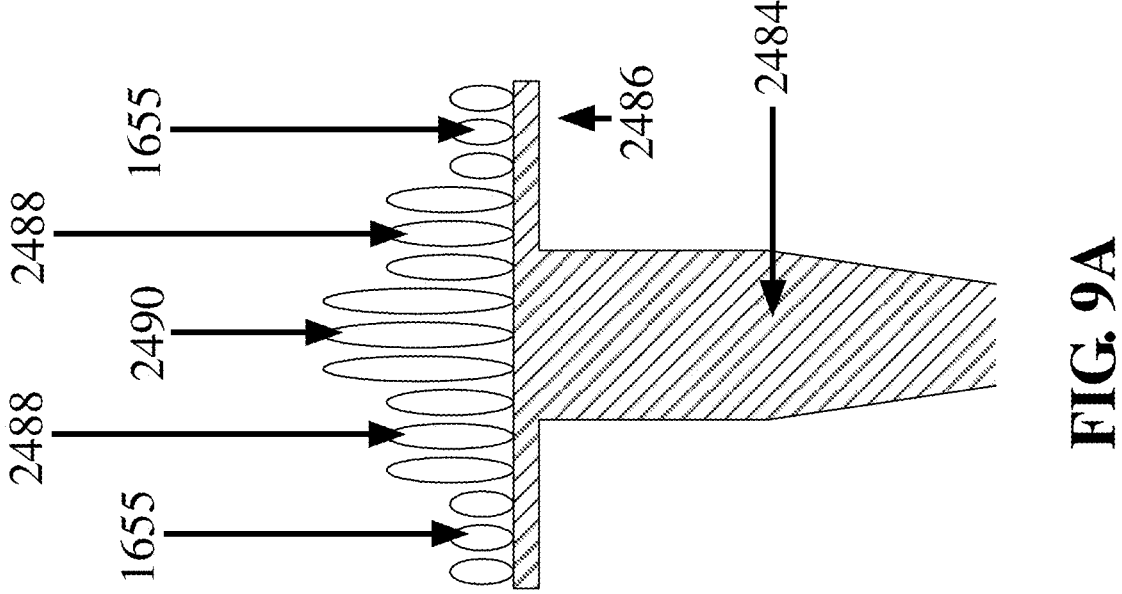
FIG. 9A depicts three (3) different height loops (1655, 2488, 2490) associated with a surface 2486 attached to a rigid handle 2484, in accordance with an embodiment of the invention.

In another embodiment further to any embodiment hereinabove, there is provided a plurality (e.g., 1, 2, 3, 4, 5, 6, or even more) of heights of loops 1655, 2488 and 2490. See e.g., FIG. 9A where there are depicted three (3) different height hooks. Similarly, FIG. 9B is a variation of FIG. 9A where there are depicted three (3) different height hooks 1660, 2491 and 2492. In an embodiment, there are provides a plurality (e.g., 1, 2, 3, 4, 5, 6, or even more) of heights of loops on a platform 2486 attached to a rigid handle 2484. In an embodiment of the invention, the different height hooks and/or different height loops can be used to sample the transformation zone, where the longest hooks and loops enter the OS cavity, the middle length hooks and loops sample deep on the walls of the OS cavity and the shortest hooks and loops sample at the outer surface of the OS cavity. In an embodiment of the invention, rotation of a FTSC device can involve sweeping regions of a length of hooks followed by regions of the same length of loops. In another embodiment of the invention, rotation of a FTSC device can involve sweeping regions of long hooks followed by regions of short loops. In an alternative embodiment of the invention, rotation of a FTSC device can involve sweeping regions of short hooks followed by regions of long loops. In an embodiment of the invention, rotation of a FTSC device can involve scraping with abrasive hooks in which some of the tissue fragments get caught up in the fenestrations followed by sweeping regions of loops which collect and retain the tissue fragments.

Figure 10B:
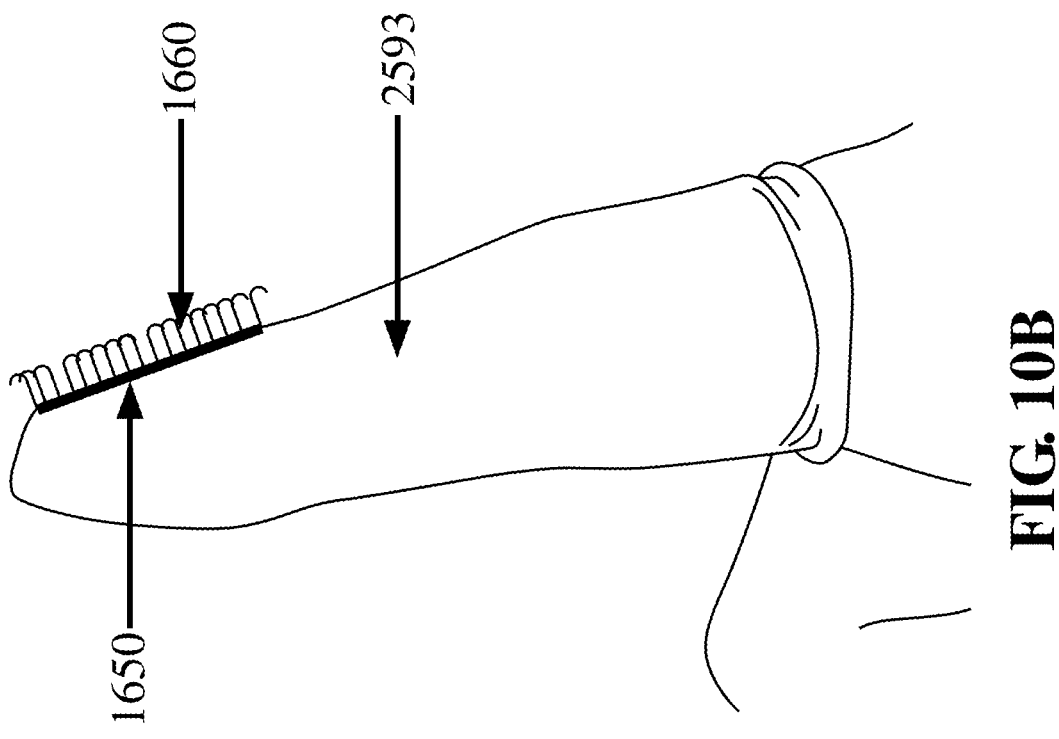
FIG. 10B depicts a finger cot 2593 having a fabric patch 1650 with hooks 1660 disposed on the dorsal (i.e., fingernail) side of the finger, in accordance with an embodiment of the invention. The orientation depicted in FIG. 10B may be useful for anal/rectal examination where, e.g., the palmar aspect of the finger can palpate a structure (e.g., possible tumor) and the fabric patch can be used for tissue or cell sampling.
Figure 10A:
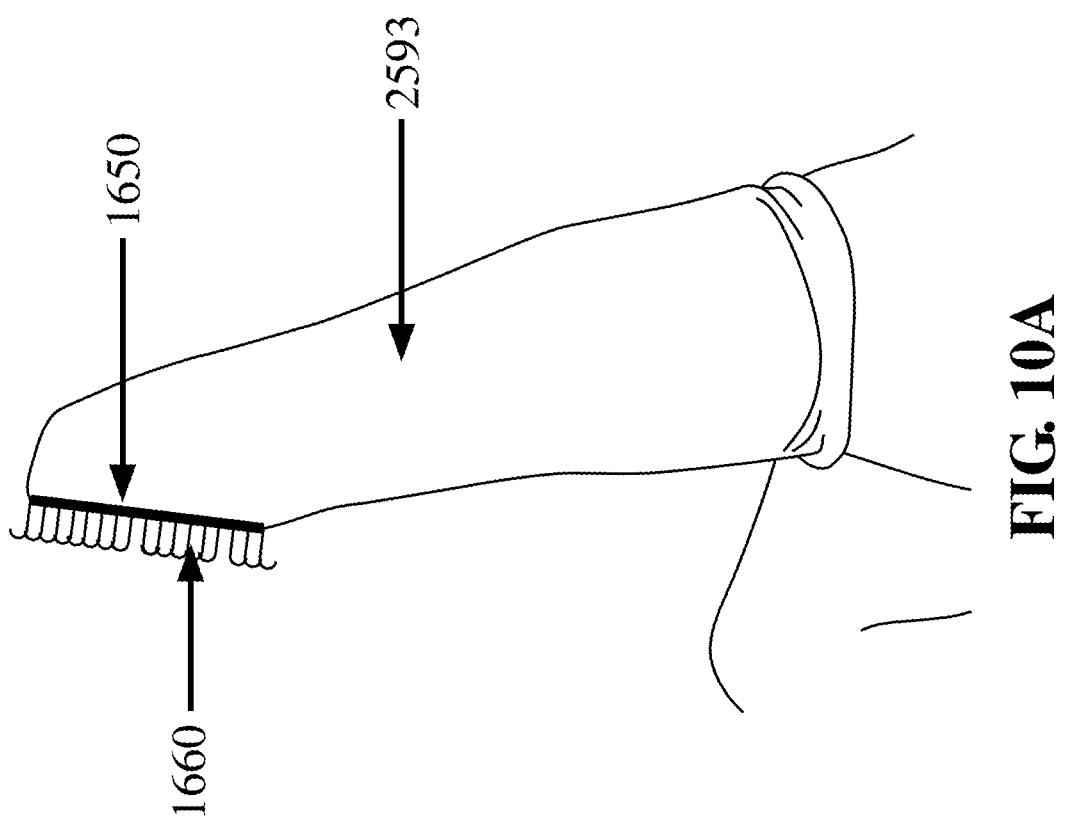
FIG. 10A depicts a finger cot 2593 having a fabric patch 1650 with hooks 1660 disposed on the palmar (i.e., fingerprint) side of the finger, in accordance with an embodiment of the invention. The patch may be useful for biopsy, sampling, or frictional abrasion including debridement.
Figure 10D:
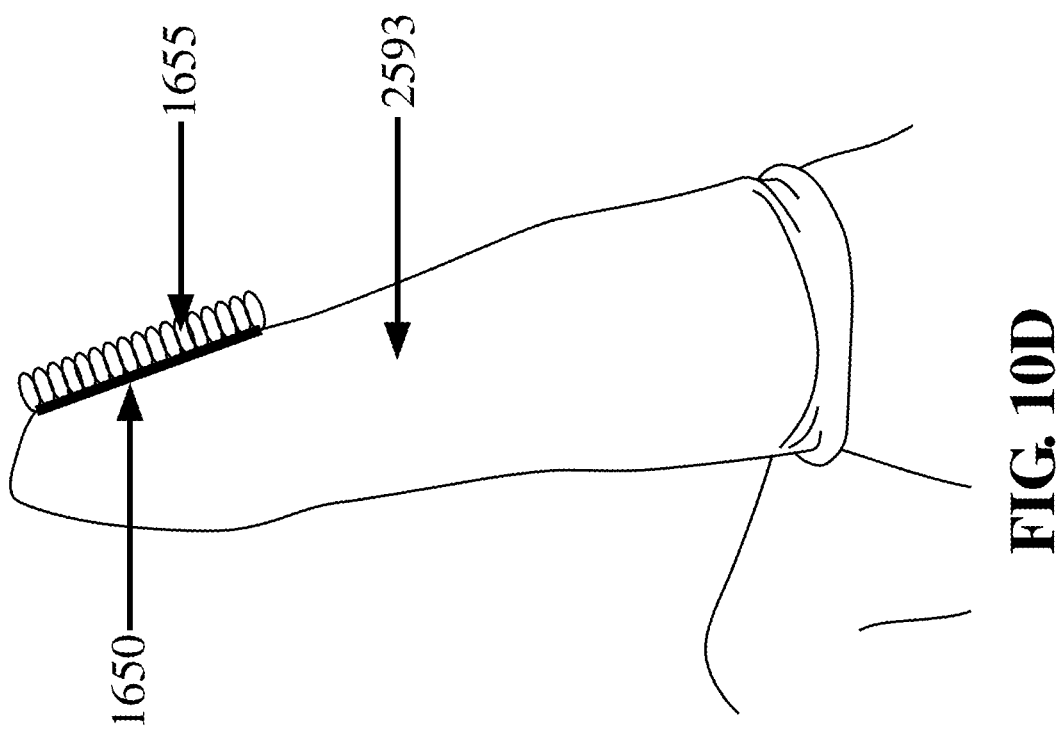
FIG. 10D depicts a finger cot 2593 having a fabric patch 1650 with loops 1655 disposed on the dorsal (i.e., fingernail) side of the finger. The patch may comprise either hooks or loops (see FIGS. 10A-10D) or both hooks and loops. The patch may be useful for biopsy, sampling, or frictional abrasion including debridement, in accordance with an embodiment of the invention.
Figure 10C:
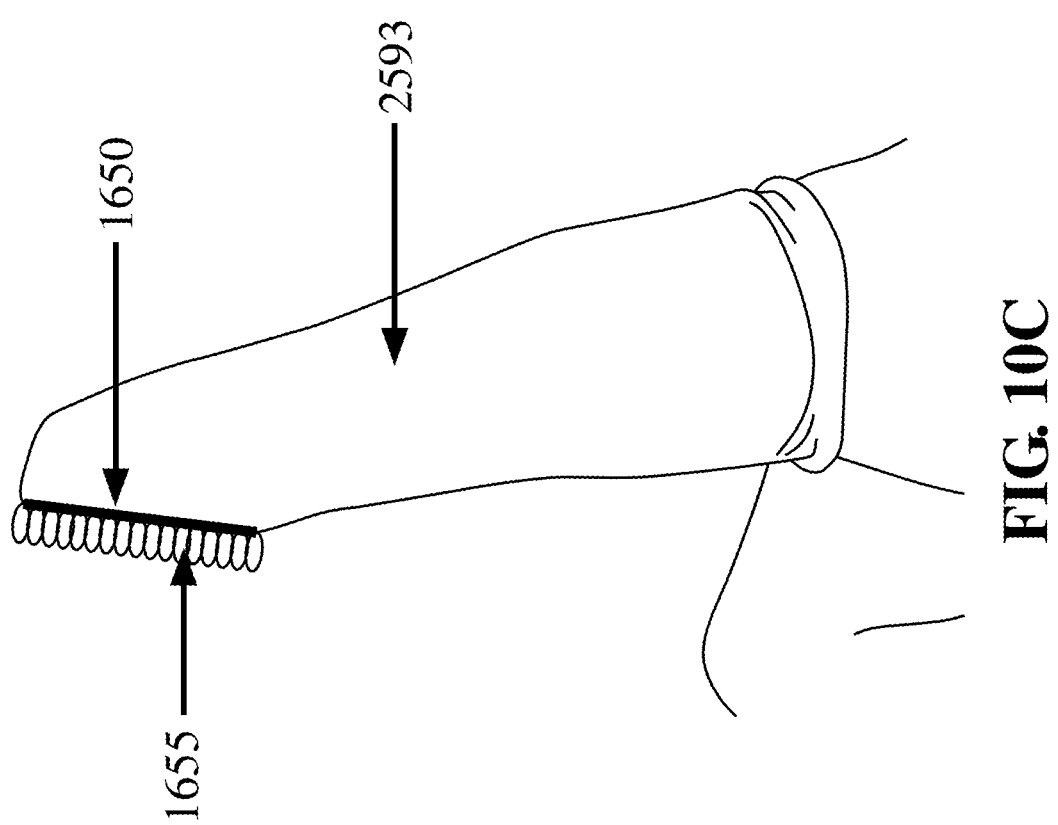
FIG. 10C depicts a finger cot 2593 having a fabric patch 1650 with loops 1655 disposed on the palmar (i.e., fingerprint) side of the finger, according to an embodiment of the invention.

In another embodiment of the present invention (see e.g., FIG. 10A, there is provided a glove or finger cot 2593 covering at least one finger and having a fabric patch 1650 disposed on the palmar (i.e., fingerprint) side of the finger. In embodiments, the patch can present hooks 1660 and/or loops 1655 (see e.g., FIG. 10C). In an embodiment of the invention, the finger cot 2593 can be rotated one hundred and eighty degrees (180°) on the finger such that FIG. 10A becomes FIG. 10B and/or FIG. 10C becomes FIG. 10D. The patch can be useful for biopsy, sampling, or frictional abrasion including debridement. In another embodiment (see FIG. 10B), there is provided a finger cot 2593 having a fabric patch 1650 disposed on the dorsal (i.e., fingernail) side of the finger. In embodiments, the patch can present hooks 1660 and/or loops 1655 (see e.g., FIG. 10D). In another embodiment of the present invention the fabric patch orientation depicted in FIG. 10B may be useful for anal/rectal examination where, e.g., the palmar aspect of the finger can palpate a structure (e.g., possible tumor) with no interfering sampling device and the finger can be rotated in situ to allow the fabric patch 1650 to be used for tissue or cell sampling of the structure.

Figures 11A, 11B:
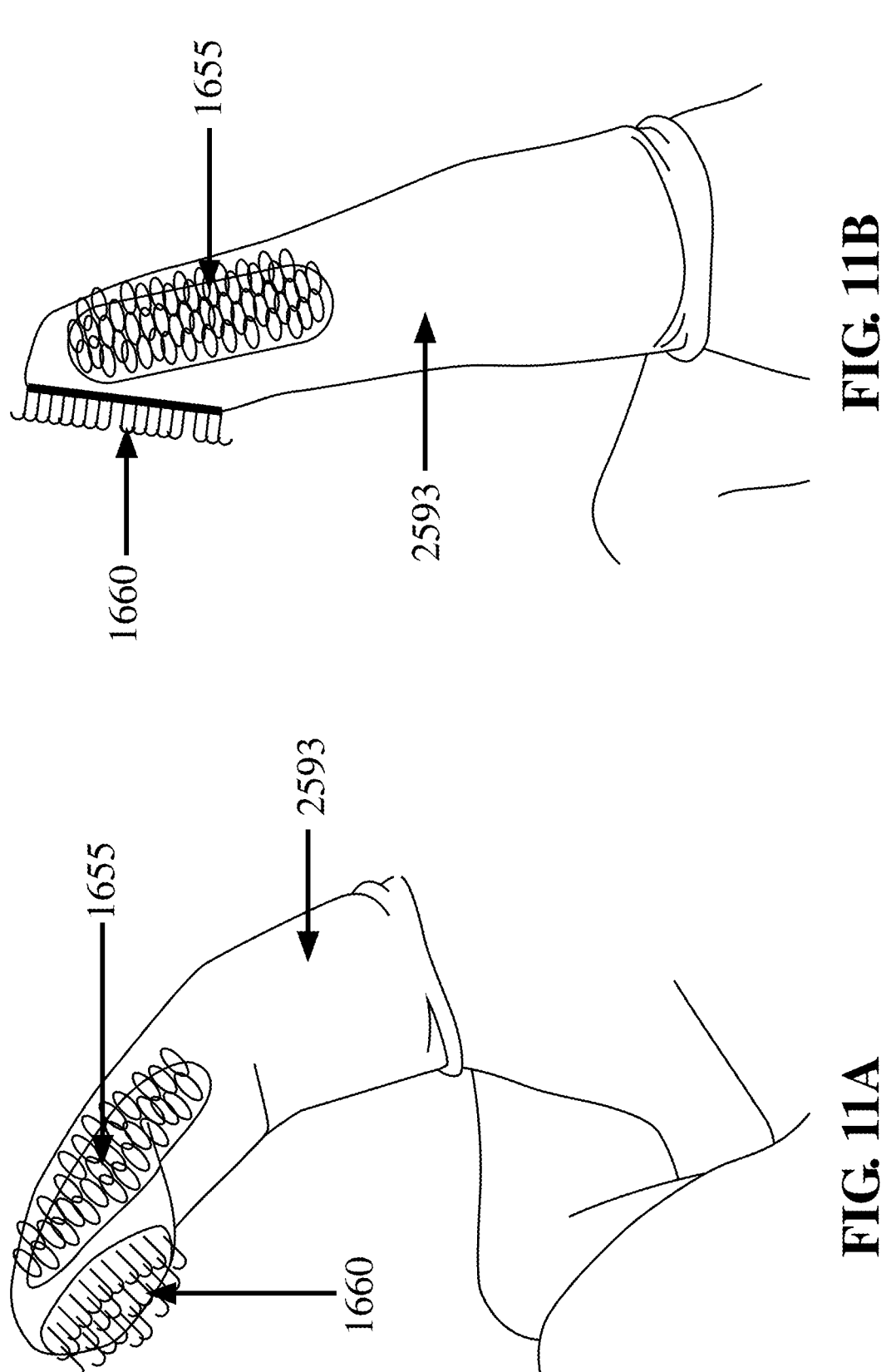
FIG. 11A depicts an embodiment of the finger cot device 2593 with the finger in a flexed position having a patch of hooks 1660 at the fingerprint region of the finger, and having a patch of loops 1655 about the distal side and/or fingernail regions of the finger cot, where the hooks 1660 and loops 1655 are not in contact, in accordance with an embodiment of the invention.
FIG. 11B depicts an embodiment of the finger cot device 2593 with the finger in a straightened position having a patch of hooks 1660 at the fingerprint region of the finger, and having a patch of loops 1655 about the distal side and/or fingernail regions of the finger cot, where the hooks 1660 and loops 1655 are not in contact, in accordance with an embodiment of the invention.
Figures 11C, 11D:
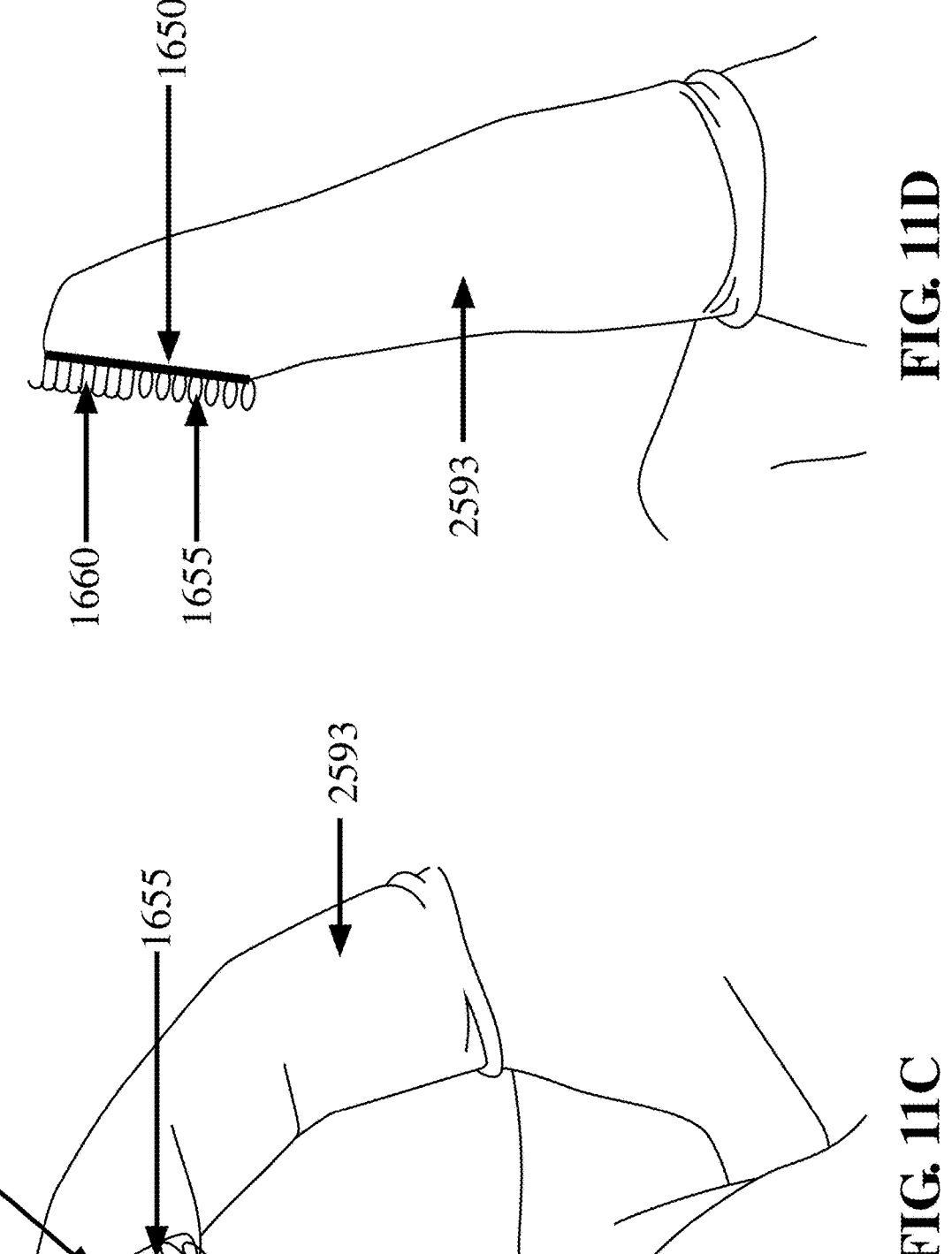
FIG. 11C depicts an embodiment of the finger cot device 2593 with the finger in a flexed position having a hybrid patch of hooks 1660, a separating region 2190, and having a patch of loops 1655 at the fingerprint region of the finger, where the hooks 1660 and loops 1655 are not in contact, in accordance with an embodiment of the invention.
FIG. 11D depicts an embodiment of the finger cot device 2593 with the finger in a straightened position having a hybrid patch of hooks 1660, a separating region 2190, and having a patch of loops 1655 at the fingerprint region of the finger, where the hooks 1660 and loops 1655 are not in contact, in accordance with an embodiment of the invention.
Figures 11E, 11F:
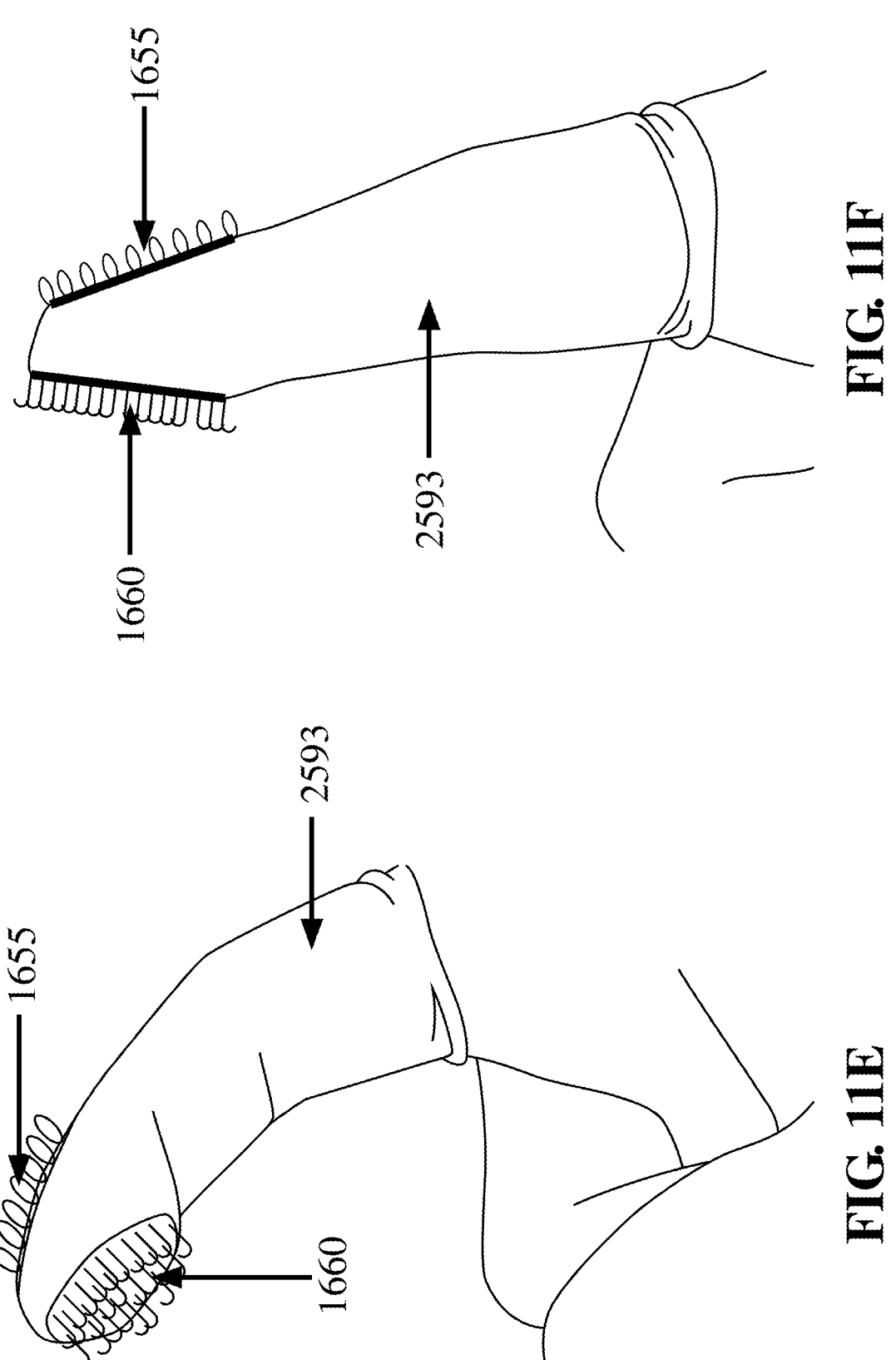
FIG. 11E depicts an embodiment of the finger cot device 2593 with the finger in a flexed position having a patch of hooks 1660 at the fingerprint region of the finger, and having a patch of loops 1655 at the dorsal region of the finger cot, where the hooks 1660 and loops 1655 are not in contact, in accordance with an embodiment of the invention.
FIG. 11F depicts an embodiment of the finger cot device 2593 with the finger in a straightened position having a patch of hooks 1660 at the fingerprint region of the finger, and having a patch of loops 1655 at the dorsal region of the finger cot, where the hooks 1660 and loops 1655 are not in contact, in accordance with an embodiment of the invention.
Figures 11G, 11H:
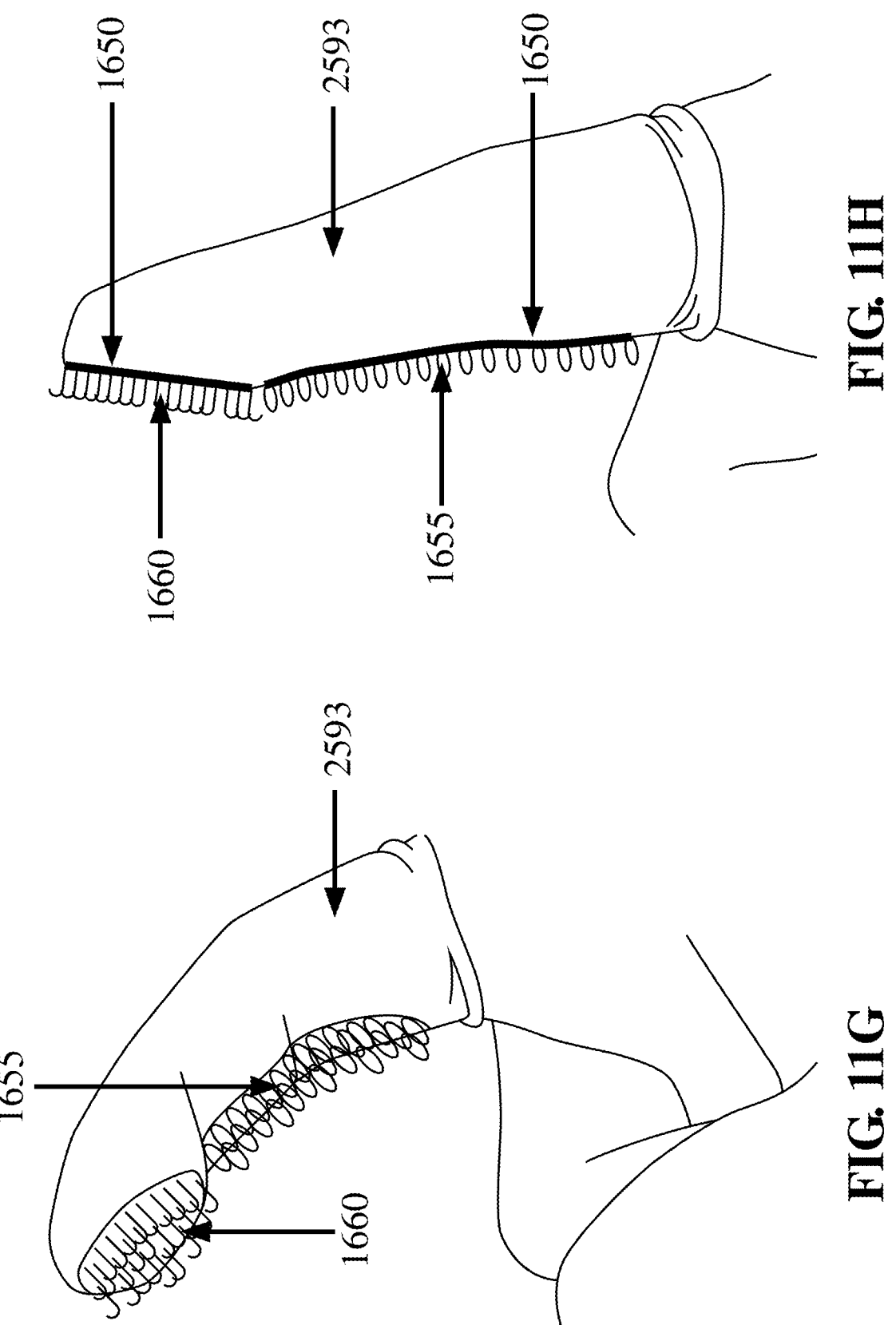
FIG. 11G depicts an embodiment of the finger cot device 2593 with the finger in a flexed position having a patch of hooks 1660 at the fingerprint region of the finger, and having an extended region of loops 1655 on the palmar aspect of the finger proximal to the patch of hooks 1655, where the hooks 1660 and loops 1655 are not in contact, in accordance with an embodiment of the invention.
FIG. 11H depicts an embodiment of the finger cot device 2593 with the finger in a straightened position having a patch of hooks 1660 at the fingerprint region of the finger, and having an extended region of loops 1655 on the palmar aspect of the finger proximal to the patch of hooks 1655, where the hooks 1660 and loops 1655 are not in contact, in accordance with an embodiment of the invention.

In other embodiments, there are provided variations on FTSC devices which incorporate gloves 2594 or finger cots 2593. For example, FIGS. 11A-11B depict flexed (FIG. 11A and straightened (FIG. 11B) examples of finger cot 2593 having a patch of hooks 1660 at the palmar (fingerprint) region of the finger, and having patches of loops 1655 about the side of the finger cot 2596 (distal side) and/or dorsal (fingernail) regions of the finger cot 2593, where the hooks 1660 and loops 1655 are separated by a gap 2190 to insure that the hooks 1660 and loops 1655 are not in contact. FIGS. 11C-11D depict flexed (FIG. 11C) and straightened (FIG. 11D) examples of finger cot 2593 having a hybrid patch at the distal palmar aspect, where the hybrid patch includes a contiguous patch of hooks 1660 adjacent to a contiguous patch of loops 1655 separated by a gap 2190. FIGS. 11E-11F depict flexed (FIG. 11E) and straightened (FIG. 11F) examples of finger cot 2593 having a patch of hooks 1660 at the palmar region of the finger, and a patch of loops 1655 at the corresponding dorsal region of the finger cot 2593. FIGS. 11G-11H depict examples of finger cot 2593 having a patch of hooks 1660 at the distal palmar aspect of the finger, and (FIG. 11G) having a region of loops 1655 on the side of the finger proximal to the patch of hooks 1660 or (FIG. 11H) having a region of loops 1655 on the proximal palmar aspect extending to the side of the finger proximal to the patch of hooks 1660. FIGS. 11C-11G can include hooks 1660 and/or loops 1655 as described herein, which can be adhered to the finger cot 2593 by a backing (e.g., adhesive) layer 1650. The backing layer 1650 can be a fabric or an adhesive fabric. In an embodiment of the invention, a patch such as shown in FIG. 11C the hooks 1660 and loops 1655 can be in contact (i.e., no gap is present or the gap is insufficient to stop the hooks and loops from touching) but the hooks are not able to fasten to the loops because of the geometric constraints (see, e.g. FIG. 14E).

Figures 11I, 11J:
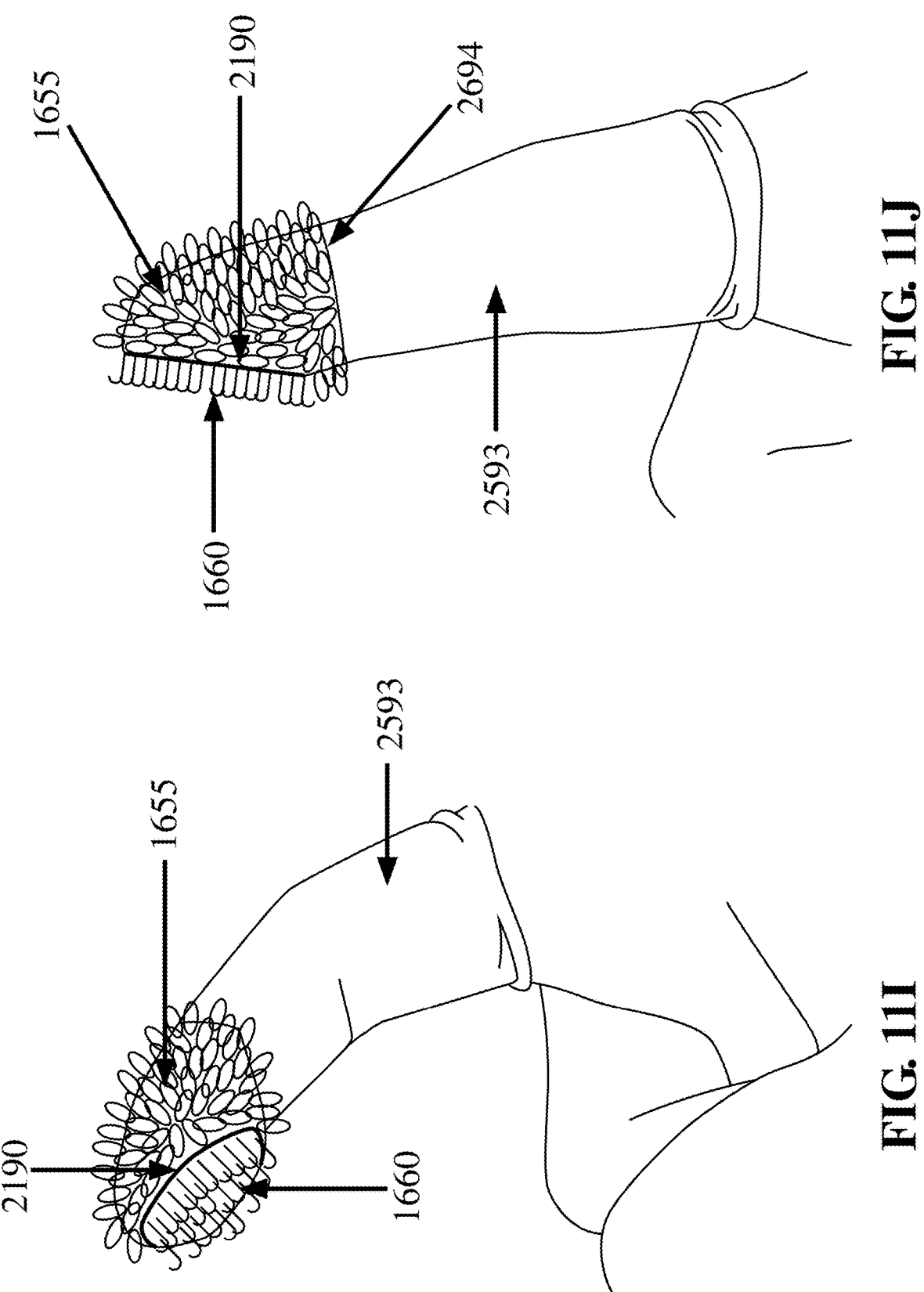
FIG. 11I depicts an embodiment of the finger cot device 2593 with the finger in a flexed position having a patch of hooks 1660 at a distal fingerprint region, which region is surrounded by one or more contiguous region of loops 1655, where the hooks 1660 and loops 1655 are not in contact, in accordance with an embodiment of the invention.
FIG. 11J depicts an embodiment of the finger cot device 2593 with the finger in a straightened position having a patch of hooks 1660 at a distal fingerprint region, which region is surrounded by one or more contiguous region of loops 1655, where the hooks 1660 and loops 1655 are not in contact, in accordance with an embodiment of the invention.
Figure 11L:
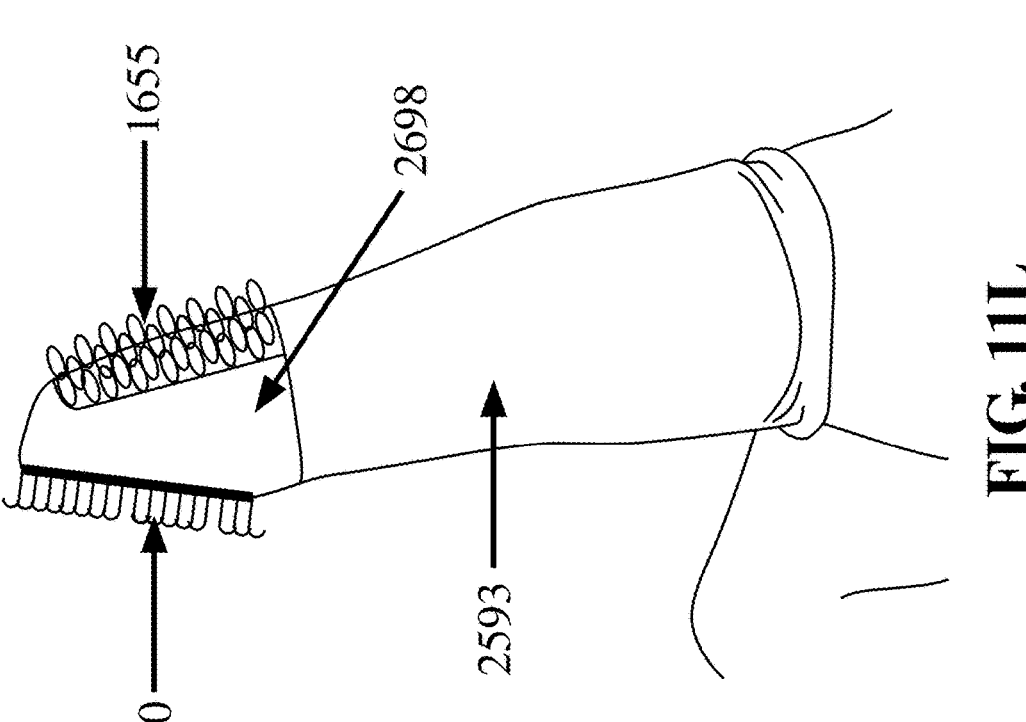
FIG. 11L depicts an embodiment of the finger cot device 2593 with the finger in a straightened position having a thimble 2698, where the thimble 2698 includes a region of hooks 1660 which can align with either the distal fingerprint region of the finger or the distal fingernail region of the finger and having a patch of loops 1655 at the opposite side of the thimble 2698, where the hooks 1660 and loops 1655 are not in contact, in accordance with an embodiment of the invention.
Figure 11K:
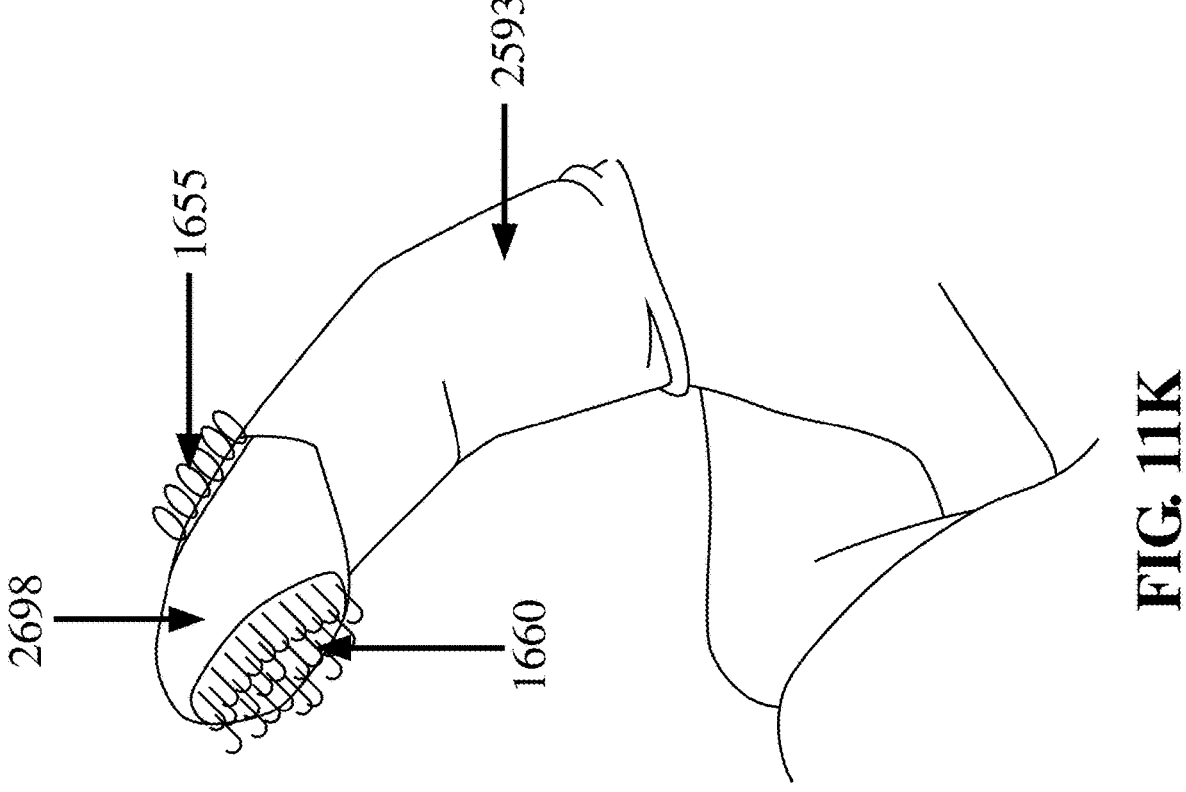
FIG. 11K depicts an embodiment of the finger cot device 2593 with the finger in a flexed position having a thimble 2698, where the thimble 2698 includes a region of hooks 1660 which can align with either the distal fingerprint region of the finger or the distal fingernail region of the finger and having a patch of loops 1655 at the opposite side of the thimble 2698, where the hooks 1660 and loops 1655 are not in contact, in accordance with an embodiment of the invention.

FIGS. 11I-11J depict flexed (FIG. 11I) and straightened (FIG. 11J) examples of a finger cot 2593 having a patch of hooks 1660 at the distal fingerprint region, which region is surrounded by a gap 2190 and then one or more contiguous region of loops 1655 extending to an intermediate phalange region 2694. FIGS. 11K-11L depict flexed (FIG. 11K) and straightened (FIG. 11L) examples of finger cot 2593 having a thimble (e.g., silicone plastic or SILASTIC™) 2698, where the thimble 2698 includes a region of hooks 1660 which can align with either the distal fingerprint region of the finger or the distal fingernail region of the finger, in combination with one or more contiguous region of hooks 1655.

Figures 12A, 12B:
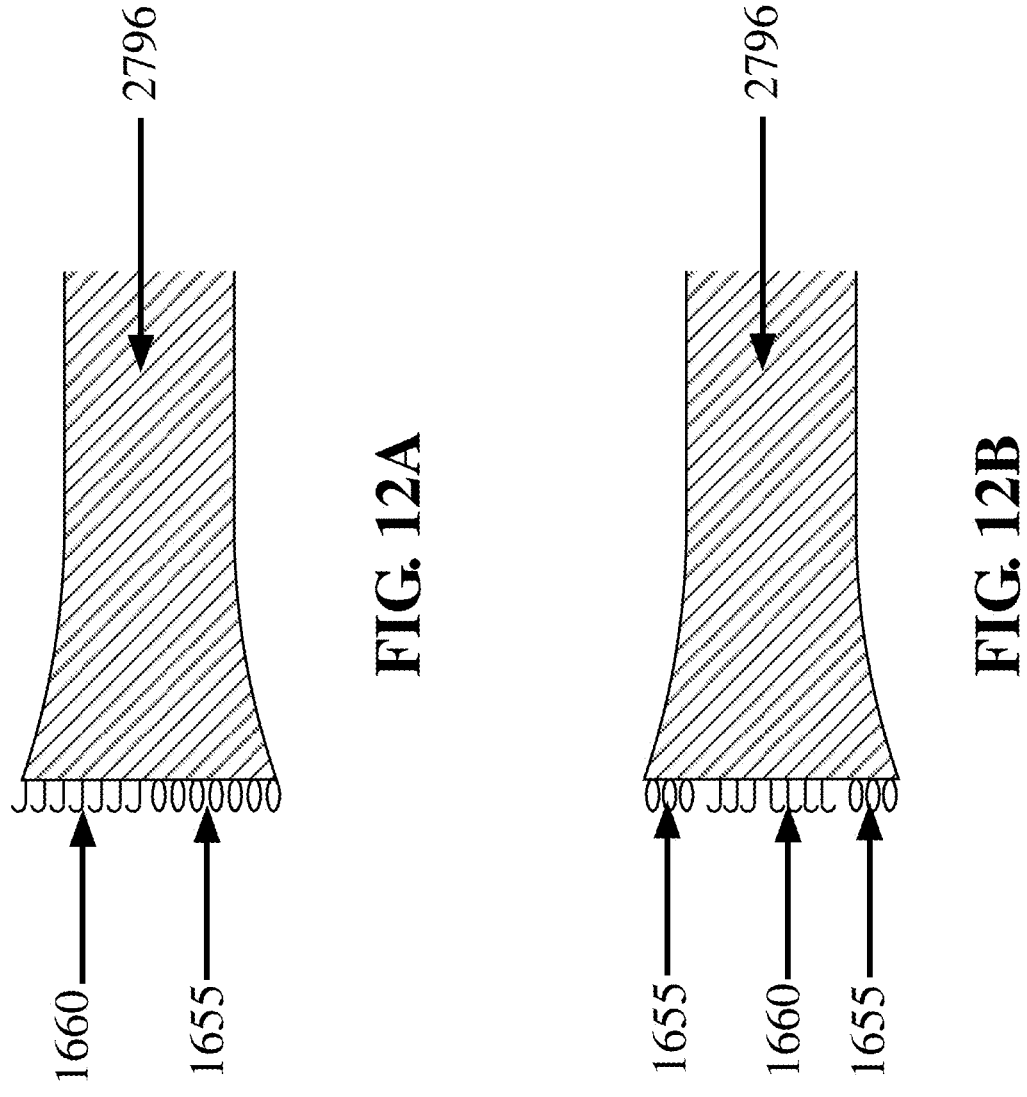
FIG. 12A depicts the distal aspects of a trumpet biopsy device 2796 having a distal flaring conical (i.e., trumpet-like) tip, which tip is useful for dislodging and collecting tissue and cells. As depicted in FIG. 12A, the trumpet tip can be segregated into two adjacent regions separated by a line which transects the flaring end of the trumpet tip, where the regions separately present 1660 and loops 1655, in accordance with an embodiment of the invention.
FIG. 12B depicts the distal aspects of a trumpet biopsy device 2796 having a distal flaring conical (i.e., trumpet-like) tip, which tip is useful for dislodging and collecting tissue and cells, in accordance with an embodiment of the invention. As depicted in FIG. 12B, the trumpet tip can be segregated into two adjacent annular regions at the flaring end of the trumpet tip, where the regions separately present hooks 1660 and loops 1655. In embodiments, hooks 1660 are in the central region, and loops 1655 are in the peripheral region. In embodiments, loops 1655 are in the central region, and hooks 1660 are in the peripheral region.

In another embodiment related to flaring (i.e., trumpet shaped) tips 2796, there are provided FTSC devices where the distal aspects have a distal flaring conical (i.e., trumpet-like) tip 2796, which tip is useful for dislodging and collecting tissue and cells. As depicted in FIG. 12A, the FTSC trumpet tip 2796 can be segregated into two (2) or more adjacent regions separated by one or more gaps which transects the flaring end of the trumpet tip, where the regions separately present hooks 1660 and loops 1655. As depicted in FIG. 12B, the FTSC trumpet tip can be segregated into two (2) adjacent annular regions at the flaring end of the trumpet tip, where the regions separately present hooks 1660 and loops 1655. In embodiments, hooks 1660 are in the central region, and loops 1655 are in the peripheral region. In an alternative embodiment, loops are in the central region, and hooks are in the peripheral region (not shown).

Figures 13A, 13B:
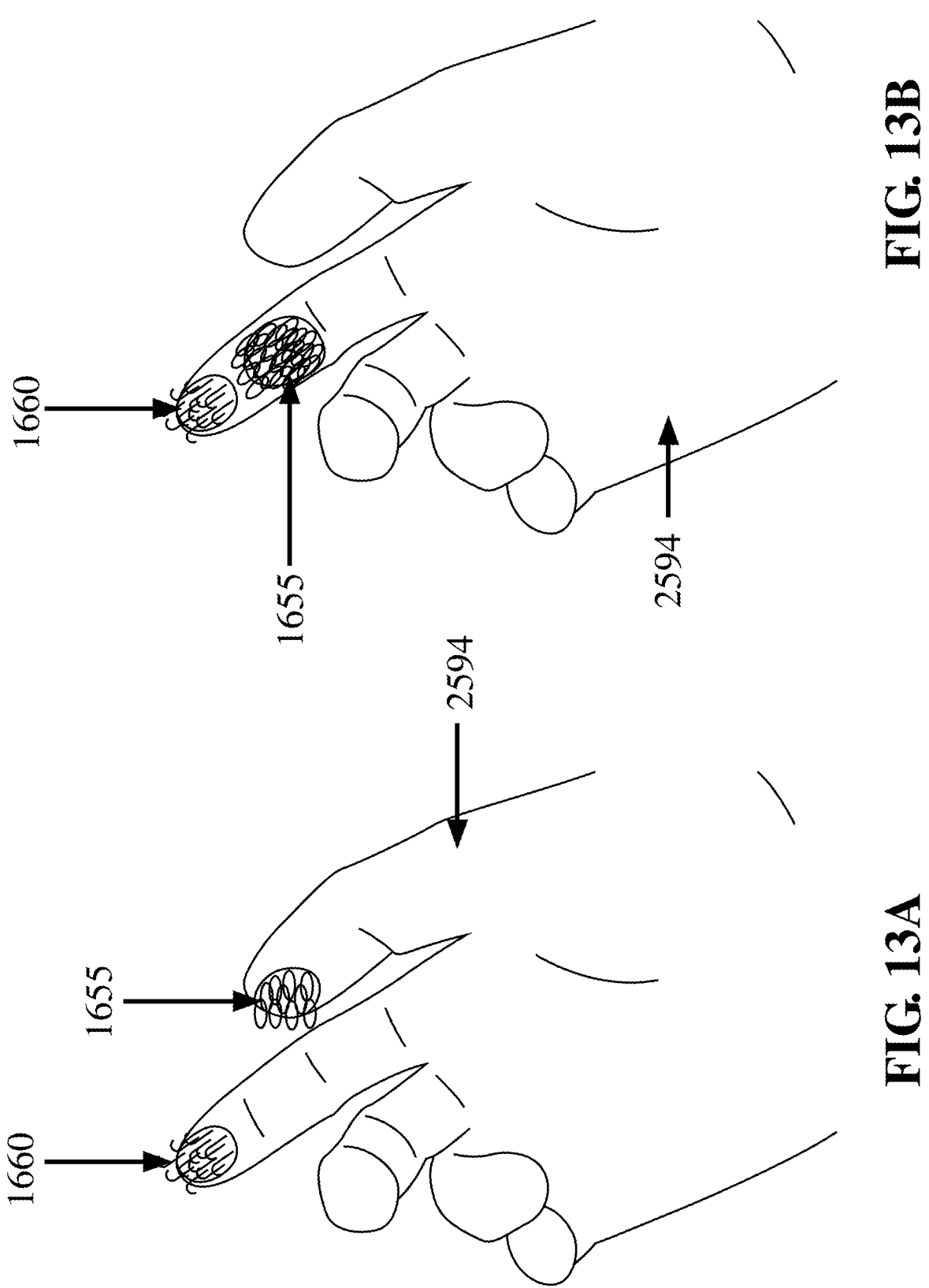
FIG. 13A depicts a full glove device corresponding to the finger cot devices described herein, in accordance with various embodiments of the invention.
FIG. 13B depicts a full glove device corresponding to the finger cot devices described herein, in accordance with various embodiments of the invention.

In another embodiment relating to gloves or finger cots, FIGS. 13A-13B depict full glove devices 2594 corresponding to the finger cot devices described herein. In FIG. 13A, a region of hooks 1660 is depicted at the distal palmar side of the middle finger of the glove 2594. A region of loops 1655 can be disposed on the distal palmar region of the thumb. After removal of tissue or cells by the hooks 1660, the tissue or cells can be transferred to the loops 1655 by touching of the thumb and third finger. In FIG. 13B, a region of hooks 1660 is depicted at the distal palmar side of the middle finger of the glove 2594. A region of loops 1655 is positioned proximal to the region of hooks 1660.

Further to any embodiment disclosed herein, in further embodiments there are provided variation in the density of hooks and loops. For example, FIGS. 14A-14E depicts different loop styles: (FIG. 14A) low density loops; (FIG. 14B) high density loops; (FIG. 14C) small loops; (FIG. 14D) large loops; and (FIG. 14E) different orientation loops. In an embodiment of the invention, the regions of low density hooks can scrape the tissue and the regions of high density loops can be used to sweep and retain dislodged tissue fragments. In an alternative embodiment of the invention, regions of high density hooks can scrape the tissue and the regions of low density loops can be used to sweep and retain dislodged tissue fragments. In an unexpected result, mucosal tissue (which is moist) sticks to fenestrated loops while skin cells (which are dry) do not stick to the fenestrated loops. Without wishing to be bound by any theory, it is believed that dry skin cells dislodge but fall between the hooks of the fenestrated loops, whereas the sweep action of the loop array adjacent or opposite to the hook array catch both dislodged tissue pieces and cells. In as much as the hooks preferentially catch tissue, the invention can be differentiated from a simple cytological sampling device.

FIGS. 15A-15C depict a scrubbing brush 3097 with hooks 1660 on one face (FIG. 15A), with loops 1655 on one face (FIG. 15B), with hooks 1660 on one face and loops 1655 on the opposite face (FIG. 15C) in accordance with various embodiments of the invention. Further, the face may include a patch which can comprise either hooks or loops (see FIGS. 15A-15B) or both hooks and loops on the one face, in accordance with various embodiments of the invention. In an alternative embodiment of the invention shown in FIG. 23, the scrubbing brush 3097 with hooks 1660 on one face and with loops 1655 on the opposite face can be elongated, e.g., shaped as a hockey puck to allow the pointed end to access a narrow crevice.

Preferred Parameters of Fibers

The frictional sampling hooks of the invention are collectively referred to as hooks, fenestrated loops or fenestrated loop fibers. They have a short hook end with the curvature starting at approximately 2 mm from the base. In various embodiments, the fenestrated loops can be approximately 2.5-25 mm in length, approximately 3-5 mm in length, approximately 3-10 mm in length, approximately 3-15 mm in length, approximately 3-20 mm in length or approximately 3-25 mm in length.

In comparison, standard Velcro is approximately 2 mm long and is more hooked. Thus, the fenestrated loops of the present invention are longer than those of standard Velcro, they are made of a similar nylon material compared with standard Velcro, are more flexible when rubbed on a tissue surface due to their length, and they have shorter loops that hook nearer to the end of the strands. In particular, the distance from the top of the loop to the bottom of the hook is preferably less than 50% of the length of the loop, more preferably less than 40%, still more preferably less than 30%, and even more preferably less than 20% the length of the loop. This distance is also preferably at least 1% the length of the loop, more preferably at least 5% the length of the loop, and still more preferably at least 10% the length of the loop. A case series of three post-hysterectomy samples proved that conventional hooked fabric such as Velcro mounted on sampling devices, pressed and rotated on the cervical epithelial surface were incapable of harvesting tissue for biopsy, while the Kylon fabric frictionally abraded tissue to a trans-epithelial depth.

Thus, the invention includes hooks in all of the ranges between any of the preferred minimum distances and any of the preferred maximum distances. The bottoms of the hooks are preferably arranged so that they are all approximately the same distance from the loop, although this is not strictly necessary. Because the hooks are cut at a relatively distal location, the ends of the hooks are more accessible to the tissue surface allowing for uniform transmission of frictional forces to the tissue surface. As a result, the action of the fibers more effectively buckle and shear the tissue, while the loops sweep over and capture the tissue.

In a preferred embodiment, the loop fibers are arranged so as to efficiently capture tissue. Thus, in one preferred embodiment, the fibers are arranged in an orderly orientation. For example, the fibers can be arranged in rows between which the tissue can be captured. The hooks can be arranged to be oriented at approximately the same angle and direction in each of the fibers. Thus, the fibers can be organized such they all have a consistent direction and angle of orientation. In addition, the spacing between each of the fibers can be made to be the same or different. The hooks 110 can be arranged in rows or equally spaced 191 (see FIG. 18B), allowing for maximal contact and abrasion. In an embodiment of the invention, an array of hooks 110 contain channels, where the hooks are separated by a distance 191 between a lower limit of approximately $10^{-4}$ meter and an upper limit of approximately $10^{-3}$ meter. In this range, approximately means plus or minus twenty percent (20%).

In use, the device can be oriented so that the fibers are perpendicular to tissue, and then pressure is applied. As a result, the distal curved short hook tips can embed into the tissue and excavate, resulting in the epithelial surface being frictionally sheared. Thus, the fibers are preferably mounted on a flat or curved platform, optimally 4-10 mm in diameter so as optimize this process. However, alternatively shaped platforms can also be used in certain embodiments. Because the fibers can be mounted directly on the platform, which can be flat or slightly curved, the orientation remains evenly spaced and the spaces inside the fenestrated loops and between them remain evenly distributed to facilitate tissue capture.

In some embodiments the platform can be in the form of a thumbtack, wherein it is attached to the handle. However, the platform and handle can take on a variety of forms. It is envisioned that the handle and the platform can be molded as one piece, and the fibers (e.g., modified Velcro can be attached with adhesive or via ultrasonic or thermal welding of the fabric to the platform.

In an embodiment of the invention, the abrasive fabric can be attached or sewed into another fabric or material such as the finger of a glove, with the human finger or hand functioning as the applicator to frictionally press and abrade the tissue surface.

In an embodiment of the invention, the Kylon fabric can be applied to existing surgical instruments such as a body part probe, clamp, or tissue manipulator via an adhesive. In this manner, the surgical instrument to which the Kylon fabric is adapted serves as a biopsy collection device.

In an embodiment of the invention, the abrasive fabric can be derivatized with functional groups to bind specific marker molecules present on cells of interest. PCT Application Number: PCT/US2009/053944, titled 'Porous Materials for Biological Sample Collection' to Zenhausern et al, which is incorporated by reference in its entirety, describes an inorganic material which can be used as the abrasive material rather than for example the Nylon which is used in Velcro to allow the specific binding and/or the solubilization of the abrasive material with appropriate solvents.

Further to any embodiment disclosed herein reciting a fabric or use of a fabric as disclosed herein, in an embodiment the fabric is an antimicrobial fabric. The term 'antimicrobial' refers in the usual and customary sense to an agent (noun) or a property of an agent (adjective) that kills and/or inhibits the growth of microorganisms. The term 'microorganism' refers in the usual and customary sense to microscopic organisms, e.g., bacteria, fungi, viruses, microscopic parasites, and the like.

Accordingly, in an embodiment, the terms 'abrasive material', 'frictional fabric', 'abrasive fabric', 'adherent abrasive fabric', 'adhered fabric', 'fenestrated loop material woven into a fabric sheet', 'hooked fabric', 'flocked fabric fenestrated loops', 'fabric for functionally abrading epithelial surfaces', 'Kylon material fabric', 'fabric patch' or the like, can be synonymous with the term 'frictional antimicrobial fabric', 'abrasive antimicrobial fabric', 'adherent abrasive antimicrobial fabric', 'adhered antimicrobial fabric', 'fenestrated loop material woven into an antimicrobial fabric sheet', 'hooked antimicrobial fabric', 'flocked antimicrobial fabric fenestrated loops', 'antimicrobial fabric for functionally abrading epithelial surfaces', 'Kylon material antimicrobial fabric', 'antimicrobial fabric patch' or the like, respectively.

In an embodiment, the abrasive material can be associated, attached or sewed into another material such as a puck, a sponge, a scrubbing pad, or a gloved finger cot. The gloved finger cot can be used with the human finger or hand functioning together with the finger cot as the applicator to frictionally press and abrade the tissue surface. In an embodiment, the fenestrated loops on a finger cot (see FIGS. 10A and 10B) are adapted for mucosal epithelium which can adhere to the rows of fenestrated loops and be trapped. Anal biopsies with a finger cot don't need the loops to trap the scrapings, as the scrapings are sticky. In this situation, the rows of fenestrated loops act in a similar fashion to cervical biopsy tissue. The rows of fenestrated loops on the finger cot can be oriented ventral (see FIG. 10A), dorsal (see FIG. 10B) or lateral (not shown). A FTSC device for obtaining a histological sample from a mucosal epithelial layer including finger cot including a patch of fenestrated loops located in a ventral area of the finger cot. A FTSC device for obtaining a histological sample from a mucosal epithelial layer including finger cot including a plurality of patches of fenestrated loops, where a first patch of the plurality of patches is located in a ventral area of the finger cot. A FTSC device for obtaining a histological sample from a mucosal epithelial layer including finger cot including a plurality of patches of fenestrated loops, where a first patch of the plurality of patches is located in a ventral area of the finger cot, where a second patch of the plurality of patches is located in a dorsal area of the finger cot. In an alternative embodiment, the antimicrobial abrasive material can be attached or sewed into another fabric or material such as a puck, a sponge, a scrubbing pad, or the finger of a glove, with the human finger or hand functioning as the applicator to frictionally press and abrade the tissue surface.

In an embodiment, a material disclosed herein can be rendered antimicrobial, e.g., by embedding, impregnating, coating or electroplating an antimicrobial agent onto the material. In an alternative embodiment, the frictional antimicrobial agent can be a core, where the core is dipped in a polymer or the polymer is otherwise applied to the outside of the antimicrobial core to coat the antimicrobial agent with a polymer. Accordingly, the resulting frictional antimicrobial fabric can be used in a body part probe, a clamp, or a tissue manipulator. In this manner, the surgical instrument to which the frictional antimicrobial fabric is adapted serves as a biopsy collection device, while maintaining antimicrobial activity.

In an embodiment, a fabric disclosed herein can be rendered antimicrobial, e.g., by embedding, impregnating, coating or electroplating an antimicrobial agent onto the fabric. In an alternative embodiment, the frictional antimicrobial agent can be a core, where the core is dipped in a polymer or the polymer is otherwise applied to the outside of the antimicrobial core to coat the antimicrobial agent with a polymer. Accordingly, the resulting frictional antimicrobial fabric can be applied to a body part probe, a clamp, or a tissue manipulator via an attachment means including an adhesive, welding including ultrasonic welding, or clamping. In this manner, the surgical instrument to which the frictional antimicrobial fabric is adapted serves as a biopsy collection device, while maintaining antimicrobial activity.

In an embodiment, the Kylon fabric can be rendered antimicrobial, e.g., by embedding, impregnating, coating or electroplating an antimicrobial agent onto the Kylon fabric. In an alternative embodiment, the frictional antimicrobial agent can be a core, where the core is dipped in a polymer or the polymer is otherwise applied to the outside of the antimicrobial core to coat the antimicrobial agent with a polymer such as nylon. Accordingly, the antimicrobial Kylon fabric can be applied to a body part probe, a clamp, or a tissue manipulator. In this manner, the instrument to which the Kylon fabric is adapted serves as a biopsy collection device, while maintaining antimicrobial activity.

Metals, in elemental (i.e., neutral metallic) form, as ions, or as part of metal complexes, possess antimicrobial activity. For example, silver, copper, gold and zinc have antimicrobial activity. Metals can be incorporated into dressings, hydrogels, hydrocolloids, foams, creams, gels, lotions, catheters, sutures, and bandages to afford antimicrobial activity.

In an embodiment of the present invention, an antimicrobial agent generates chlorine ions. A source of chlorine such as an alkali metal or alkali earth metal salt of hypochlorite, trichloro-S-triazinetrione, sodium dichloro-S-triazinetrione, cyanuric acid can be used as an antimicrobial agent. In an alternative embodiment of the invention a source of bromine such as bromo-chloro-5,5 dimethylhydantoin can be used as an antimicrobial agent. In an embodiment of the invention, both cations and anions can be a source of antimicrobial agent. In an embodiment of the invention, an antimicrobial agent (e.g., silver chloride, gold chloride, gold bromide or silver bromide) can release both anions ($Cl^-$ or $Br^-$) and cations ($Au^+$ or $Ag^+$) with antimicrobial effect. In an embodiment of the present invention, an antimicrobial agent can be mixed together with an inert compound (such as lactose, or cellulose) in order to reduce the rate of solubilization of the antimicrobial agent.

In an aspect, there is provided a frictional antimicrobial form of a fabric disclosed herein. In an embodiment, there is provided a frictional antimicrobial fabric for functionally abrading a tissue. The frictional antimicrobial fabric includes a base material and a hook material attached to the base material. The hook material is suitable for abrading a tissue to provide a tissue sample or a cell sample. The base material, the hook material, or both the base material and hook material can include an antimicrobial agent which can render the material antimicrobial, e.g., by embedding, impregnating, coating, electroplating, consisting of or otherwise adhering an antimicrobial agent onto the material. Similarly, the base material, the loop material as disclosed herein, or both the base material and loop material can include an antimicrobial agent which can render the materials antimicrobial, e.g., by embedding, impregnating, coating, electroplating or otherwise adhering an antimicrobial agent onto the material.

In an embodiment, the frictional antimicrobial fabric includes a loop material rather than a hook material. In this embodiment, the loop material is woven into the base material, and the loop material extends perpendicularly or at an acute angle from the base material. Moreover, the loop material is adapted to allow collection of tissue, cells, or both tissue and cells.

In an embodiment of the frictional antimicrobial fabric for functionally abrading a tissue, the fabric further includes a loop material, where the loop material is woven into the base material. The loop material extends perpendicularly or at an acute angle from the base material. The loop material is adapted to allow collection of tissue, cells, or both tissue and cells.

Further to any embodiment of a frictional antimicrobial fabric disclosed above, in an embodiment the antimicrobial agent is adhered to the base material, the loop material, or the hook material. In an embodiment, the antimicrobial agent is embedded, impregnated, coated or electroplated onto the base material, the loop material, or the hook material. In an embodiment, the antimicrobial agent is selected from the group consisting of an elemental metal, a metal ion, and a metal complex. In any embodiment, the metal of the elemental metal, metal ion, and metal complex is copper, silver, gold, or zinc. In an embodiment, the metal of the elemental metal, metal ion, and metal complex is silver.

Further to any embodiment contemplating antimicrobial activity of any device or method disclosed herein, in some embodiments an antimicrobial agent is adhered to a fabric or patch thereof of the device or method, a base material or patch thereof, a loop material or patch thereof, or a hook material or patch thereof. In an embodiment, the antimicrobial agent is embedded in the fabric, hook, loop and/or base material of the fabric. In an embodiment, the antimicrobial agent is impregnated into the fabric, hook, loop and/or base material of the fabric. In an embodiment, the antimicrobial agent is coated onto the fabric, hook, loop and/or base material of the fabric. In an embodiment, the antimicrobial agent is electroplated onto the fabric, hook, loop and/or base material of the fabric. Methods for electroplating metals onto plastics and other nonmetalic surfaces are well known in the art. Methods for coating or otherwise depositing polymers (e.g., plastics) onto metallic surfaces are also well known in the art.

In an embodiment, the antimicrobial agent is an elemental metal (i.e., metallic metal). In an embodiment, the metal is copper, silver, gold or zinc. In an embodiment, the metal is silver.

In an embodiment, the antimicrobial agent is a metal ion. In an embodiment, the metal ion derives from a metal salt adhered (i.e., embedded, impregnated, or coated) to the fabric or patch thereof, base material or patch thereof, loop material or patch thereof, or hook material or patch thereof. In an embodiment, the metal ion is copper, silver, gold or zinc ion. In an embodiment, the metal ion is a silver ion.

In an embodiment, the antimicrobial agent is a metal complex. In an embodiment, the metal complex generates 'metal ions'. In an embodiment of the invention, the metal complex is adhered (i.e., embedded, impregnated, inserted or coated) to the polymer or patch thereof, base material or patch thereof, loop material or patch thereof, or hook material or patch thereof. In an embodiment, the metal within the metal complex is one or more of a copper ion, a silver ion, a gold ion, and a zinc ion. In an embodiment, the metal within the metal complex is silver. In an embodiment, the metal within the metal complex is silver coated copper. In an embodiment, the metal within the metal complex is copper coated silver.

In another aspect, there is provided an antimicrobial Frictional Tissue Sampling and Collection (aFTSC) paddle device for obtaining a DNA sample including a first side and a second side, where the second side is opposite the first side, where an abrasive material is associated with the first side a collector material is associated with the second, and where the one or both of the abrasive material and the collector material includes an antimicrobial agent as disclosed herein. The term 'antimicrobial Frictional Tissue Sampling and Collection (aFTSC) paddle device' or the like refers to an FTSC paddle device as disclosed herein additionally having at least one antimicrobial component. The term 'antimicrobial component' refers to any part of a device disclosed herein having antimicrobial properties. In an embodiment, a component is adhered with an antimicrobial agent, thereby rendering the component a antimicrobial component.

In another aspect, the aFTSC device or a FTSC device can become electrically charged. The electrical charge can be induced by contacting the aFTSC or FTSC device with another material. The polarity and magnitude of the charge on the aFTSC or FTSC device can be optimized based on the position of (i) the conducting material in the aFTSC or FTSC device and (ii) the material in the triboelectric series. In an embodiment, the source of the antimicrobial agent is encased in a polymer. For example, the polymer encasing the source of the antimicrobial agent can be nylon in order to charge the aFTSC or the FTSC device with a positive charge. The polymer can be polyester in order to charge the aFTSC or the FTSC device with a negative charge. The charge can be used to modulate the propensity of the antimicrobial agent to generate cations and/or anions. In an alternative embodiment, silver chloride is encased in a polymer. The polymer encasing the can be nylon in order to charge the aFTSC with a positive charge. A positive charge can be used to direct the anions. The polymer can be polyester in order to charge the aFTSC with a negative charge. The polymer can be polystyrene in order to charge the aFTSC with a negative charge. A negative charge can be used to direct the cations. In another embodiment of the invention, a silver chloride antimicrobial agent is coated around a copper core which is encased in a polymer. The polymer encasing the silver chloride coated copper can be nylon in order to charge the aFTSC with a positive charge. The polymer can be polyester in order to charge the aFTSC with a negative charge. The polymer can be polyester in order to charge the aFTSC with a negative charge. In an embodiment of the invention, the aFTSC is polarized with an external voltage. In an alternative embodiment of the invention, the aFTSC can include a capacitor located near the base material of the aFTSC or FTSC device. In another embodiment of the invention, the capacitor can be charged with soundwaves. In another embodiment of the invention the capacitance of the capacitor can be altered by soundwaves. In another embodiment of the invention, the soundwaves can be supplied through by an ultrasonic generator. In another embodiment of the invention, the soundwaves can be supplied through tissue for use of the aFTSC or FTSC device with a cavity.

Figure 16:
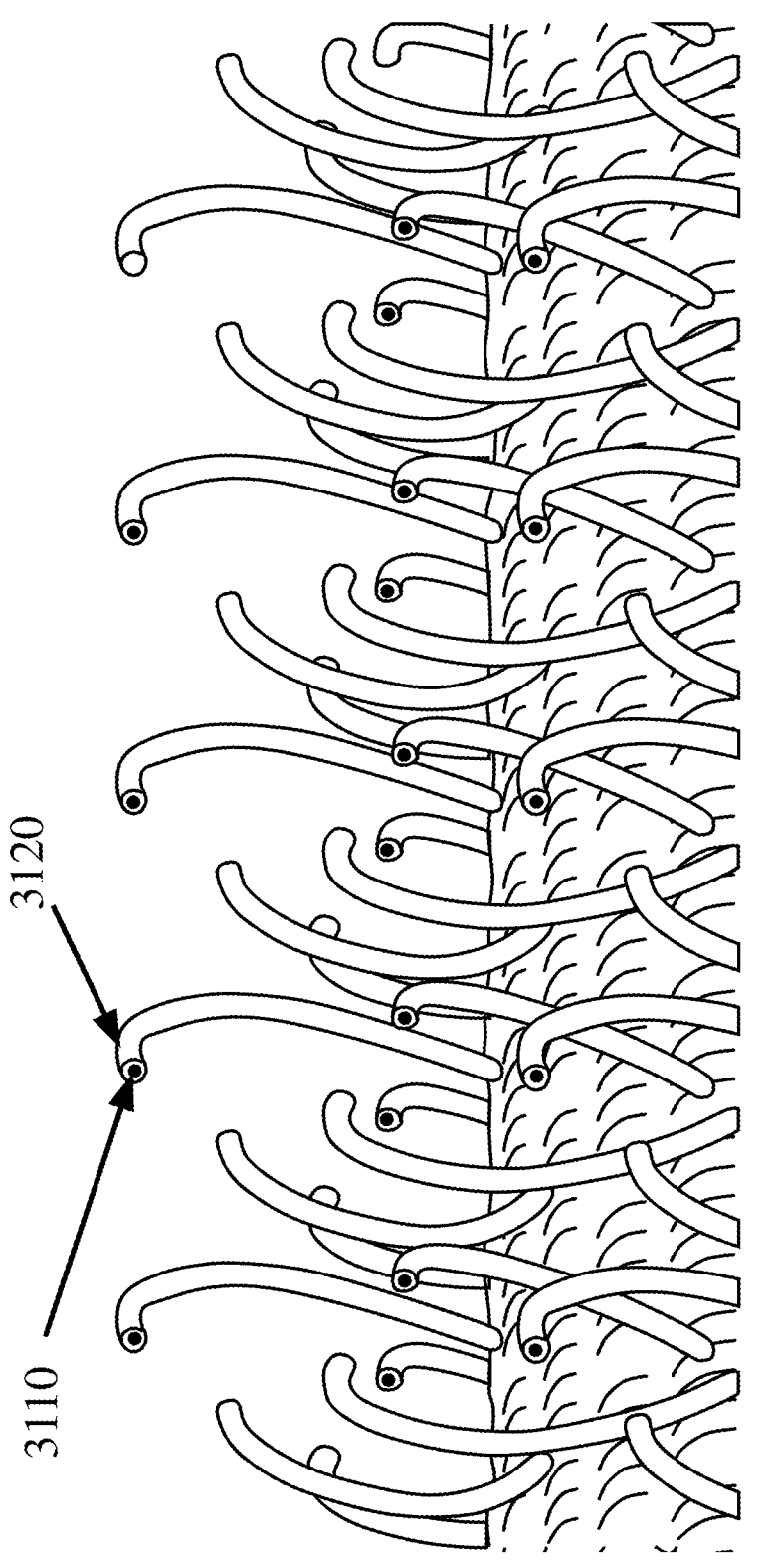
FIG. 16 is a schematic of an expanded side view of antimicrobial Frictional Tissue Sampling and Collection (aFTSC) material where each hook is made up of an abrasive agent and either an antimicrobial agent or a conductive agent, in accordance with various embodiments of the invention.

FIG. 16 is a schematic of an expanded side view of aFTSC or FTSC material where each hook is made up of an abrasive agent and an antimicrobial agent or a conductive agent. In an embodiment of the invention, the abrasive agent 3110 is coated with or encloses an antimicrobial agent located on the outside of the hook 3120. In another embodiment of the invention, the abrasive agent 3110 is coated with or encloses a conductive agent located on the outside of the hook 3120. In an alternative embodiment of the invention, the antimicrobial agent 3110 is coated with or encloses an abrasive agent located on the outside of the hook 3120. In an alternative embodiment of the invention, the conductive agent 3110 is coated with or encloses an abrasive agent located on the outside of the hook 3120.

Figure 17:
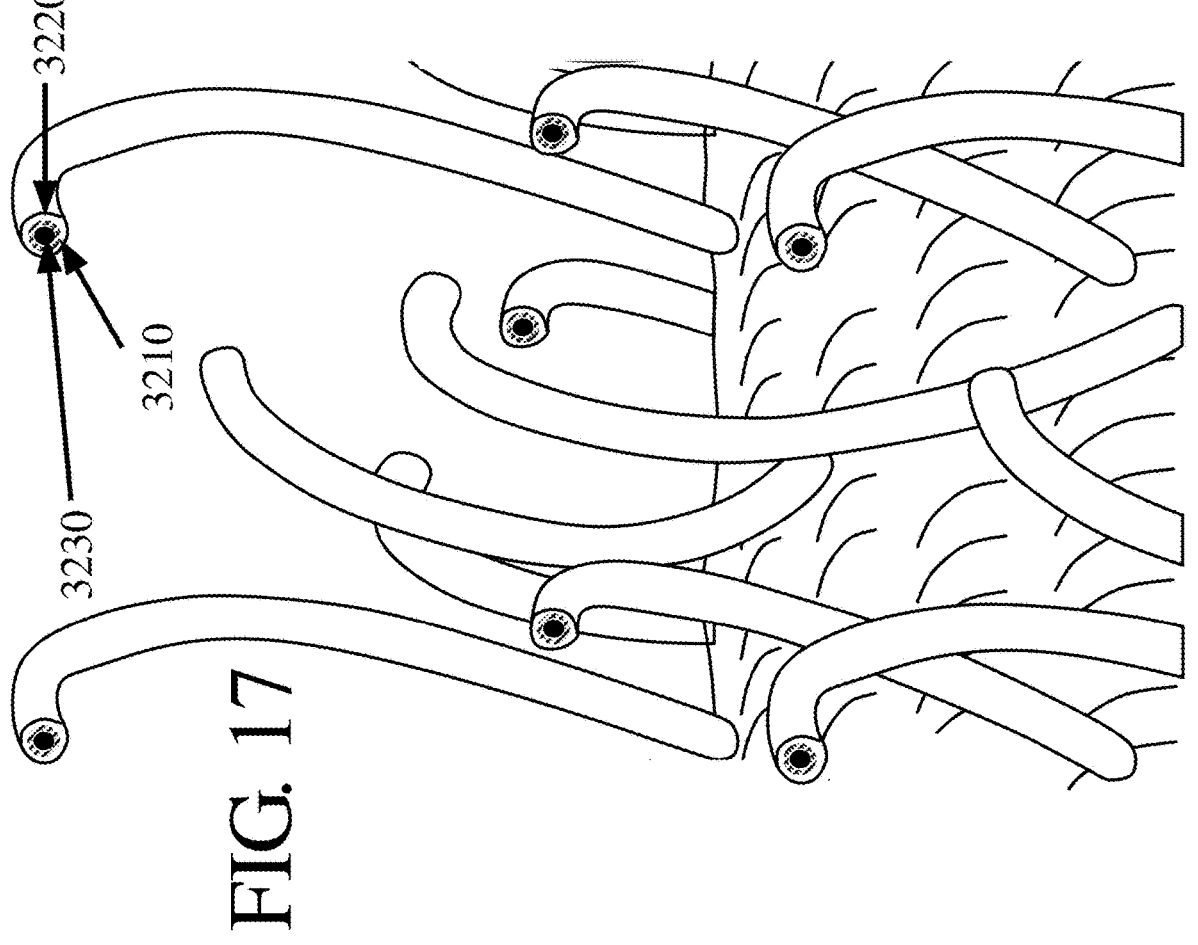
FIG. 17 is a schematic of an expanded side view of aFTSC material where each hook is made up of a abrasive agent, an antimicrobial agent and a conductive agent, in accordance with various embodiments of the invention.

FIG. 17 is a schematic of an expanded side view of aFTSC material where each hook is made up of a abrasive agent, an antimicrobial agent and a conductive agent. In an embodiment of the invention, the abrasive agent 3230 is coated with or encloses an antimicrobial agent 3210 sandwiched between a conductive agent located on the outside of the hook 3220. In another embodiment of the invention, the antimicrobial agent 3230 is coated with or encloses an abrasive agent 3210 sandwiched between a conductive agent located on the outside of the hook 3220. In a further embodiment of the invention, the conductive agent 3230 is coated with or encloses an antimicrobial agent 3210 sandwiched between an abrasive agent located on the outside of the hook 3220. In a further embodiment of the invention, the conductive agent 3230 is coated with or encloses an abrasive agent 3210 sandwiched between an antimicrobial agent located on the outside of the hook 3220. In an embodiment of the invention, the abrasive agent 3230 is coated with or encloses a conductive agent 3210 sandwiched between an antimicrobial agent located on the outside of the hook 3220. In an embodiment of the invention, an antimicrobial agent 3230 is coated with or encloses a conductive agent 3210 sandwiched between the abrasive agent agent located on the outside of the hook 3220.

The aFTSC can be used to treat calyces surrounding the apex of the renal pyramids. In alternative embodiments of the invention, the aFTSC can be used to sample urticarial tissue. In alternative embodiments of the invention, the aFTSC can be used to sample tissue present in the endocervix, the vagina, the anus, the hypopharynx, and the esophagus. In an alternative embodiment of the invention, the aFTSC can be used to sample endometrium. In another embodiment of the invention, the aFTSC can be used to sample wounds and burns. In another embodiment of the invention, the abrasion can be used to effect debridement of the burn site. In another embodiment of the invention, the electric charge associated with the aFTSC or FTSC device can be used to cauterize wounds and burns. In an embodiment of the invention, the electric charge can be induced on the aFTSC or FTSC fabric and discharged on the wound surface to cause a local cauterizing.

In an embodiment of the aFTSC paddle device, the abrasive material is an abrasive antimicrobial fabric, and the collector material is a collector antimicrobial fabric. The term 'abrasive antimicrobial fabric' refers to an abrasive fabric as disclosed herein which also includes one or more antimicrobial agents as disclosed herein. The term 'collector antimicrobial fabric' refers to a collector fabric as disclosed herein which also includes one or more antimicrobial agents as disclosed herein.

In another aspect, there is provided a method of obtaining nucleic acid information from an antimicrobial Frictional Tissue Sampling and Collection (aFTSC) device for obtaining a DNA sample including an abrasive material associated with a first area, and a collector material associated with a second area, where the first area is distinct from the second area. The method includes a) sampling with the aFTSC device; b) withdrawing the aFTSC device; and c) placing one or both the abrasive material associated with the first area and/or the collector material associated with the second area in a solution to preserve the DNA sample. The term 'antimicrobial FTSC device for obtaining a DNA sample' or the like refers to an FTSC device as disclosed herein additionally having at least one antimicrobial component.

In another aspect, there is provided a device for obtaining a cell and biopsy tissue sample. The device includes a) a finger cot including two or more patches, where a first patch is located on a distal palmar aspect of the finger cot and a second patch, b) an antimicrobial abrasive attached to the first patch; and c) an antimicrobial collector attached to the second patch. The term 'patch' refers to a fabric as disclosed herein which is adapted to fit a localized region and is otherwise synonymous with the term fabric.

In another aspect, there is provided a method of obtaining nucleic acid information from an antimicrobial Frictional Tissue Sampling and Collection (aFTSC) device for obtaining a DNA sample including an antimicrobial abrasive attached to a first patch, and an antimicrobial collector attached to a second patch, where the first patch is distinct from the second patch. The method includes the steps of: a) sampling a cavity of a mammal with the aFTSC device; b) withdrawing the aFTSC device; and c) placing one or both the antimicrobial abrasive associated with the first patch and/or the antimicrobial collector associated with the second patch in a solution to preserve the DNA sample.

In another aspect, there is provided an aFTSC device for obtaining a DNA sample, the device including: a) an antimicrobial abrasive material associated with a first area of the device; and b) an antimicrobial collector material associated with a second area of the device, where the first area is distinct from the second area.

In another aspect, there is provided a method of obtaining nucleic acid information from an aFTSC device for obtaining a DNA sample including an antimicrobial abrasive material associated with a first area of the device, and an antimicrobial collector material associated with a second area of the device, where the first area is distinct from the second area. The method includes the steps: a) sampling with the aFTSC device; b) withdrawing the aFTSC device; and c) placing one or both the antimicrobial abrasive material associated with the first area and/or the antimicrobial collector material associated with the second area in a solution to preserve the DNA sample.

In another aspect, there is provided a kit including: a) an aFTSC device as disclosed herein and packaged in a sterile container; and b) instructions for use of the aFTSC device.
Method of Inducing an Immune Response by Autoinoculation In some embodiments, the trans-epithelial, frictional tissue sampling and collection devices described herein are utilized to agitate and disrupt epithelial cells containing a pathogen, or cellular proteins altered by a pathogen, to induce an immune response against the pathogen. This results in auto-inoculation of tissues that harbor pathogens and macromolecules such as virally altered DNA and/or oncogenic proteins. The method can also be termed therapeutic frictional abrasion-excoriation. This method is advantageous when a pathogen is normally able to evade an immune response. For example, some viruses remain in surface epithelial layers where they are sequestered from the immune system. Other viruses can be integrated into cellular DNA, thereby evading immune detection.

The methods of inducing an immune response against a pathogen that normally evades the immune system comprise the steps of (a) disrupting epithelial cells containing the pathogen, virally altered DNA, or cellular oncoproteins with a micro-curettage device described herein, and (b) introducing the pathogen into the bloodstream of a patient to elicit an immune response.

In some embodiments, the trans-epithelial, frictional tissue sampling and collection devices described herein are utilized to disrupt epithelial cells to induce an immune response against human papillomaviruses (HPVs). HPVs are persistent viruses that can remain in their hosts for long periods of time before causing any ill effects. Generally, the host reacts to viral pathogens by generating both humoral and cell-mediated responses. Humoral responses are typically antibody-mediated and involve the secretion of antibodies such as immunoglobulin A (IgA) and immunoglobulin G (IgG) by B lymphocytes. Cellmediated responses, on the other hand, are carried out by immune effector cells such as dendritic cells (DCs), natural killer (NK) cells, macrophages and T lymphocytes which secrete a number of cytokines including interferon (INF) and tumor necrosis factor (TNF), and up-regulate the expression of Fas ligand (FasL) and TNF-related apoptosis inducing ligand (TRAIL) on their cell surface.

In the case of HPV infection, the immune response is frequently weak or undetectable, and accompanied by little or no inflammation. Even when an immune response is elicited, it may not be able to clear the virus. Disruption of the epithelial surface by frictional tissue disruption induces repair and inflammation and serves to autoinoculate the patient. Without wishing to be bound by any theory, exposure of the epithelial surface to frictional tissue disruption, uniquely induced by the apparatus and methods disclosed herein through local heating from friction forces exerted, can enhance the induction of repair, inflammation and an immune response following patient autoinoculation. Agitation or scrubbing of a lesion serves to introduce viral particles into the bloodstream of a patient, where they can trigger a humoral or antibody-related immune response. In addition, the method can fracture cells releasing antigens locally within the tissue stroma, inducing a cell mediated response associated with the release of cytokines and attraction of helper and killer T cells to the sampled tissue area.

Advantageously, the method of the present invention auto-inoculates a patient with viral particles of the specific viral serotype(s) that the patient is infected with. In contrast, current vaccine strategies are effective on a subset of HPV strains. For example, GARDASIL® by Merck & Co., Inc. is indicated to help prevent cervical cancer, precancerous and low-grade cervical lesions, vulvar and vaginal pre-cancers and genital warts caused by human papillomavirus (HPV) types 6, 11, 16 and 18, and CERVARIXT® by GlaxoSmithKline is an HPV 16/18 cervical cancer candidate vaccine. The vaccine is commonly injected in a limb, not the target organ at risk, the cervix, and has been only documented to elicit a humoral antibody immune reaction.

Drug Application

In some embodiments, an adjuvant drug or an immune modulating agent is used in combination with the autoinoculation method, thus augmenting an immune response. For example, Imiquimod (ALDARA® topical cream, manufactured and marketed by Graceway Pharmaceutical Company) is approved for the treatment of actinic keratosis, external genital warts and superficial basal cell carcinoma (sBCC), a type of skin cancer. An immune response can be enhanced by using such immune modulating agents in combination with autoinoculation by the methods described herein. The adjuvant drug can be applied to the fenestrated loop fibers directly akin to toothpaste on a toothbrush, or a channel within the applicator can be used to transmit the drug from the top of the handle by means of a squeeze bulb or syringe, through a small lumen in the center of the fabric disc, concomitant with the tissue disruption, delivering drug into the fracture crevices created during the frictional buckling and shearing process created by the device.

Some embodiments comprise a method of drug delivery to a pathological lesion or areas of tissue that concomitantly disrupts tissue planes, creating crevices or pathways for drugs to enter via intra-epithelial and sub-epithelial spaces. This is in contrast to topical therapies, which are slowly absorbed into and through the epithelia. Intra-lesional application is more focused and requires less drug, presenting less risk of side effects.

Any type of drug (e.g., ablative, antibiotic, antiseptic, immune modulating, etc.) can be used.

In some embodiments, drug is delivered via an applicator including a fabric with fenestrated loops as described herein. Drug is applied in a manner akin to applying toothpaste to a toothbrush, or drug can injected onto the platform or the apparatus via a channel leading through a hollow applicator handle. The drug application apparatus can optionally have an element through which the drug is delivered (e.g., a syringe with a locking mechanism). Drug is applied to a 'wound' created by frictionally agitating the tissue. In some embodiments, the fenestrated loops can be impregnated with a drug during manufacture, wherein the drug leeches out into the disrupted tissue when the fiber contacts and macerates/disrupts the tissue.

In an embodiment of the invention, a system for using and monitoring an FTSC device during a surgical procedure, comprises an FTSC head and handle, a comb for removing the tissue from the FTSC head, and a means for rotating the FTSC handle. The means for turning the FTSC head can include an automated device. The FTSC rotating device can include an input module for selecting parameters for use with the FTSC device, wherein the input module selects parameters based at least in part on the FTSC head device selected, a sensor for monitoring the FTSC head rotating velocity, a processor for comparing the rotational velocity of the FTSC head and the selected parameters and automatically adjusting the FTSC head rotation velocity when the comparison indicates an increased or decreased head rotation is required. The input module can receive audio, tactile or visual feedback to adjust the FTSC device during the surgical procedure.

In an embodiment of the invention, the FTSC device can be applied in any surgical, scientific, crime investigation or veterinary application that requires the use of a regulated constant or variable rotating tissue sampler. This can include laboratory equipment that requires tissue sampling, storage or any other clinical procedure.

A method for simultaneously dilating a cervix and obtaining a transformation zone biopsy with minimal discomfort to a patient including selecting a FTSC head with a facet in the FTSC head, wherein the FTSC head is received in a handle, wherein the FTSC head is selected to dilate the cervix without causing discomfort to the patient. Inserting the head of the FTSC device into the non-dilated cervix to a depth that does not cause discomfort to the patient. Waiting for the cervix to at least partially dilate. Further inserting the head of the FTSC device into the partially dilated cervix to a depth that does not cause discomfort to the patient. Incrementally repeating these steps until the facet at least partially rests against the transformation zone. Rotating in a first direction one or both the handle and the FTSC head to frictionally abrade the transformation zone. Removing the FTSC head from the cervix. Using a comb to remove tissue from the cervix by brushing the head in a second direction, wherein the second direction is opposite of the first direction. Depositing the tissue removed from combing the head in a fixing solution.

A device for obtaining a biopsy tissue sample including a head with a proximal end, a distal end, wherein the head has a first maximum diameter. Further including a facet extending from the distal surface of the head, wherein the facet has a surface contour, wherein the surface contour has a second maximum diameter, wherein the second maximum diameter is at least 1 mm less than the first maximum diameter, wherein the perimeter of the facet has a railing, wherein the railing can be used to form a pool of adhesive prior to the adhesive being cured. Further including a handle with a proximal and a distal end, wherein the proximal end of the head is connected to the distal end of the handle. Also including an abrasive material, wherein the abrasive material is adhered to the facet with the adhesive.

A device for obtaining a biopsy tissue sample including a head with a proximal end, a distal end and a handle with a proximal end and a distal end, wherein the proximal end of the head is connected to the distal end of the handle. The device further including a facet associated with the distal surface of the head, wherein the facet has a surface contour, wherein a plurality of fenestrated loops extend from the surface of the facet, wherein the plurality of fenestrated loops are secured to the facet, wherein when the device is in contact with tissue and rotated the plurality of fenestrated loops frictionally abrade the tissue to obtain a biopsy sample, wherein the plurality of fenestrated loops are made of the same material as the facet.

A FTSC device for obtaining a histological sample from an epithelial layer includes a paddle with a main axis including a first side and a second side, where rotation of the paddle around the main axis rotates the first side away from a user and brings the second side towards the user, an abrasive material associated with the first side, where the abrasive material is adapted to abrade the epithelial layer to dislodge the histological sample, and a collector material associated with the second side, where the collector material is adapted to collect the histological sample dislodged by the first side of the paddle.

In an embodiment of the invention, a FTSC device including a smooth (non sampling) or 'sled side' 1650 facilitates rotation of the FTSC device. A prototype FTSC device was used in an investigational study, see presentation by Juan C. Felix and Mark Winter entitled 'Clinical Utility Pilot Study of a Novel Tissue-Trap Brush in Histologic Sampling of the Cervical Transformation Zone' at the American Society of Colposcopy and Cervical Pathology Meeting, Las Vegas, NV, Apr. 12, 2018, which is expressly incorporated by reference in its entirety and for all purposes, in which the propellers 1640, 1643 were at an angle of approximately ninety (90) degrees to the axis of the handle 1610, see e.g., FIG. 1G. In the Felix et al. study, it was found that by simultaneously pressing a smooth surface 1643 and rough surface 1660 and rotating the FTSC device around the main axis 1665 on sensitive tissue like the mucosa of a cervix the intermittent sensation of the smooth 'sled side' 1643 distracted the patient from the pain experienced from the rough surface 1660. Further, the device is arrow shaped with a nose cone 1630 where the rough surface 1660 extended to the nose cone 1630. In an embodiment of the invention, Kylon 1660 coats one propeller 1640 and the lateral side of the nose cone 1630 almost to the center of the main axis of rotation. The center of the main axis of rotation of the nose cone 1630 or the tip is smooth (non sampling) or 'naked', so as to serve as an entry point to a canal and possibly dilate a canal. In an unexpected result, the Felix study showed the pain experienced was low. In another unexpected result, the Felix study showed that the smooth propeller blade 1643 counterbalanced the frictional propeller blade 1660 and thereby facilitated rotation allowing for ease of use. Neither of these results were anticipated from a large frictional device.

Figures 1G, 1H:
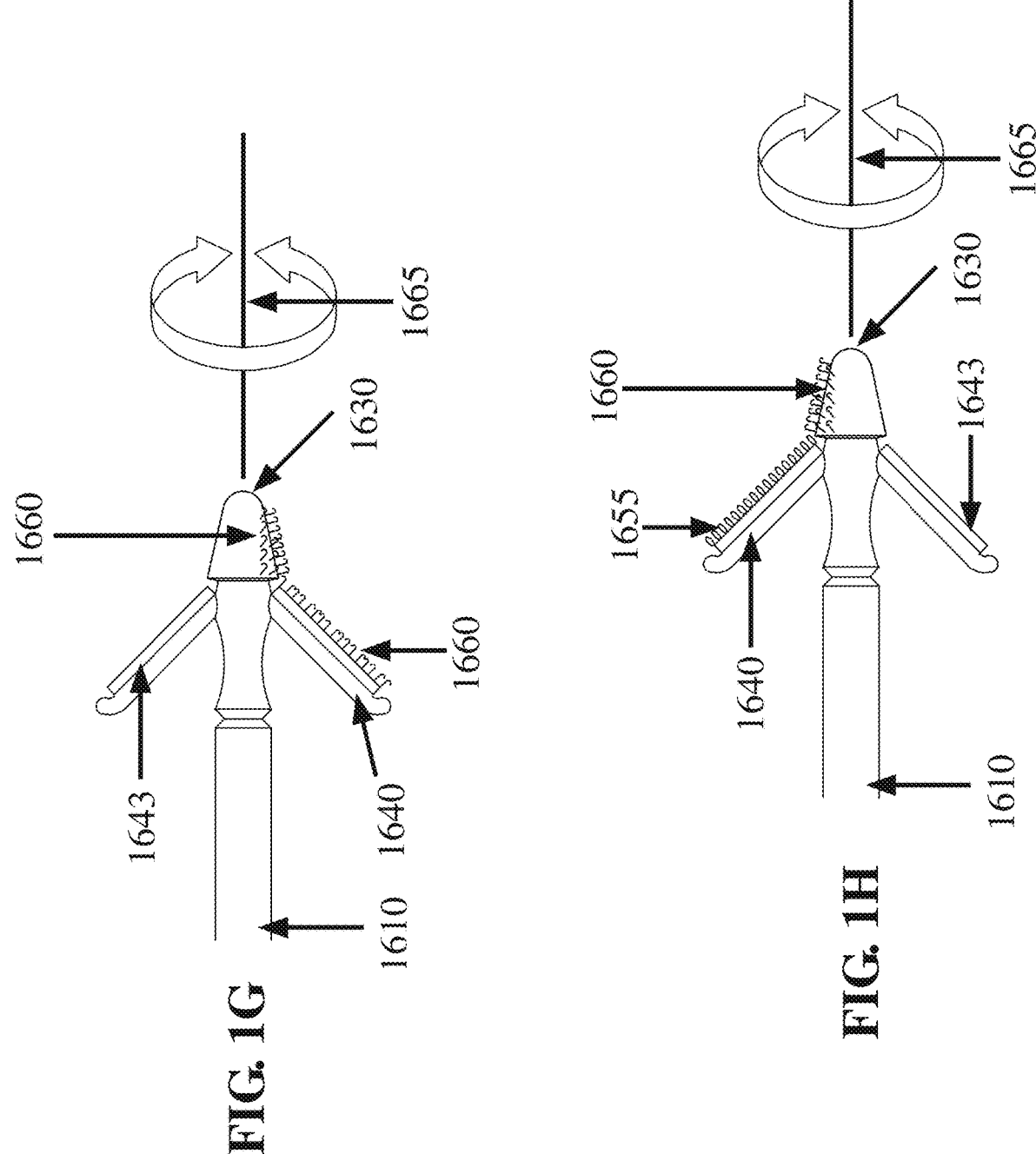
FIG. 1G shows a side view of a propeller FTSC device with two blades visible (1640, 1643), where a first surface on a first blade 1640 presents hooks 1660 and a patch of hooks 1660 on the nose cone 1630 act to frictionally abrade a tissue surface while a second surface on a second separate blade 1643 is smooth, in accordance with an embodiment of the invention.
FIG. 1H shows a side view of a propeller FTSC device with two blades visible (1640, 1643), where a first surface on a first blade 1640 presents loops 1655 to collect a sample and a patch of hooks 1660 on the nose cone 1630 act to frictionally abrade a tissue surface while a second surface on a second separate blade 1643 is smooth, in accordance with an embodiment of the invention.

In an embodiment of the invention, a FTSC device including a smooth (non sampling) or 'sled side' 1650 facilitates rotation of the FTSC device for collection, see e.g., FIG. 1H. There is a collecting side 1655, and a smooth (non sampling) or 'sled side' 1643 to the device. Further, the device is arrow shaped with a nose cone 1630 where the rough surface 1660 is positioned on the nose cone 1630. In an embodiment of the invention, loops 1655 coat one propeller blade 1640. The center of the main axis of rotation of the nose cone 1630 or the tip is smooth (non sampling) or 'naked', so as to serve as an entry point to a canal and possibly dilate a canal.

In an embodiment of the invention, there are two propellers 1640, 1643 because when pressed into a dome shaped tissue surface like a cervix, with a central canal like a doughnut shaped tissue, the shape of the nose cone extending to the paddles or propellers can recess into the canal, apply pressure to the lateral walls of the canal entry, the outer cervix around the canal, and the distal canal tissue (this allows contact to the entire transformation zone of the cervix).

Figures 6C, 6D:
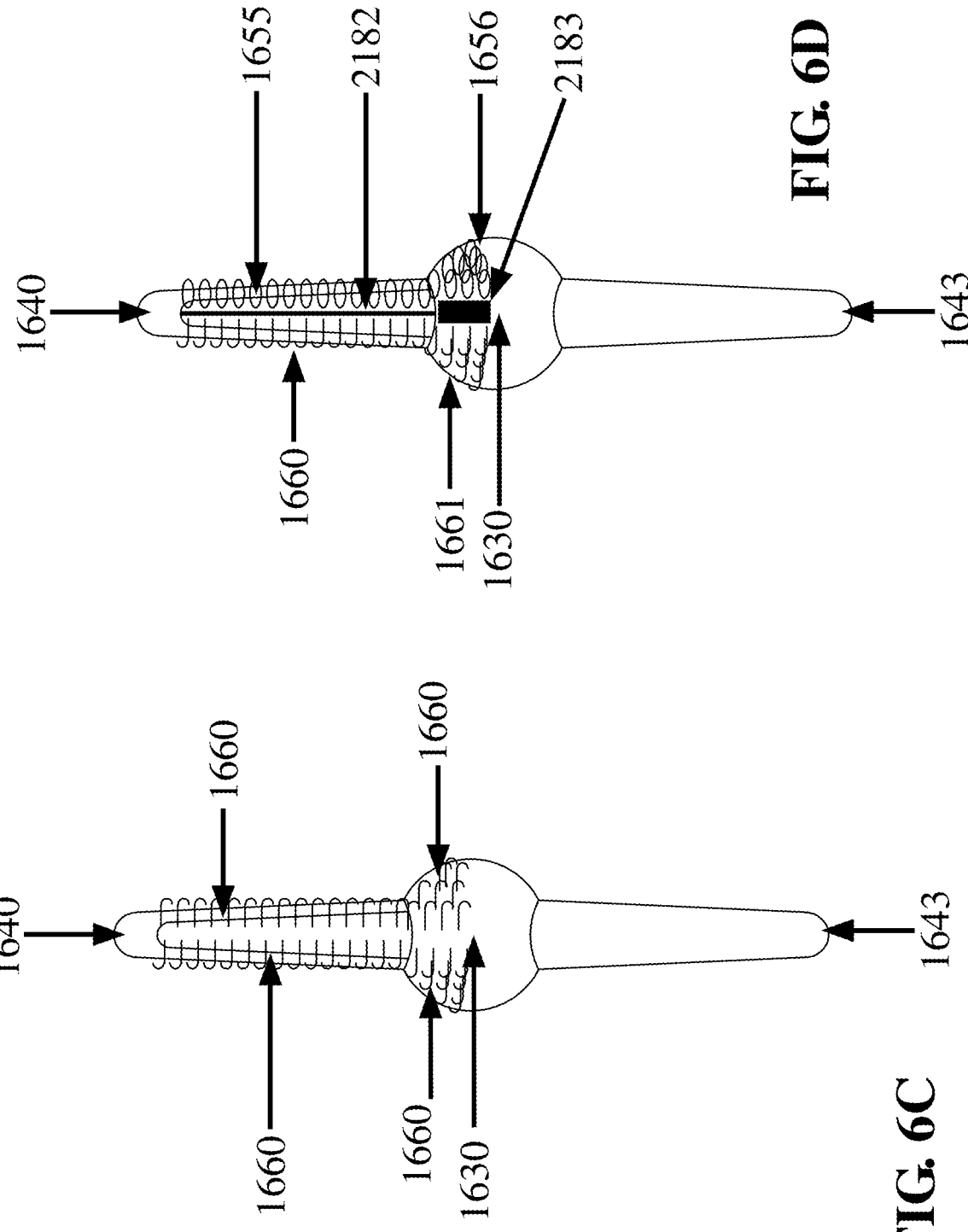
FIG. 6C is a side view of the FTSC device shown in FIG. 1G, where one sampling propeller blade 1640 emanating from the nose cone 1630 of the FTSC device is covered with hooks 1660, and having hooks 1660 on the nose cone 1630, and a smooth (non sampling) propeller blade 1643, in accordance with an embodiment of the invention.
FIG. 6D is a variation on FIG. 6B, where one sampling propeller blade 1640 emanating from the nose cone 1630 of the FTSC device is split along the local long axis into two (2) sections, one with hooks 1660 on one side and loops 1655 on the other side, and having a first vertical gap 2182 in between the hooks 1660 and loops 1655 on the sampling propeller blade 1640, and having hooks 1660 on one side and loops 1655 on the other side of the nose cone 1630, and having a second vertical gap 2183 in between the hooks 1660 and loops 1655 on the nose cone 1630, and a smooth (non sampling) propeller blade 1643, in accordance with an embodiment of the invention.

In an embodiment of the invention, the naked side serves to balance the pressure and prevent wobble as the device is rotated around its axis to frictionally sample tissue with hooks 1660, and collect tissue and cell pieces within the loops 1655. In an embodiment of the invention, a FTSC device with hooks on one propeller blade and a second propeller blade naked can be used for frictionally biopsied tissue, see FIG. 1G. In an alternative embodiment of the invention, a FTSC device with loops on one propeller blade and a second propeller blade naked can be used for small tissue and cell sampling, see FIG. 1H. In an embodiment of the invention, the one propeller for frictionally abrading and sampling can be combined, see FIG. 6B and FIG. 6D where there are hooks are on one side of the propeller blade and loops on the other side of the same propeller. In various embodiments of the invention, the two sides can be separated horizontally (as shown in FIG. 7A and FIG. 7B or vertically (as shown in FIG. 6B and FIG. 6D). In an embodiment of the invention, the propellers 1640, 1643 can be oriented into an arrow shape. In an embodiment of the invention, more representative tissue can be sampled from the 'at risk' area for neoplasia of the cervix with an arrow shaped FTSC device.

Figure 18B:
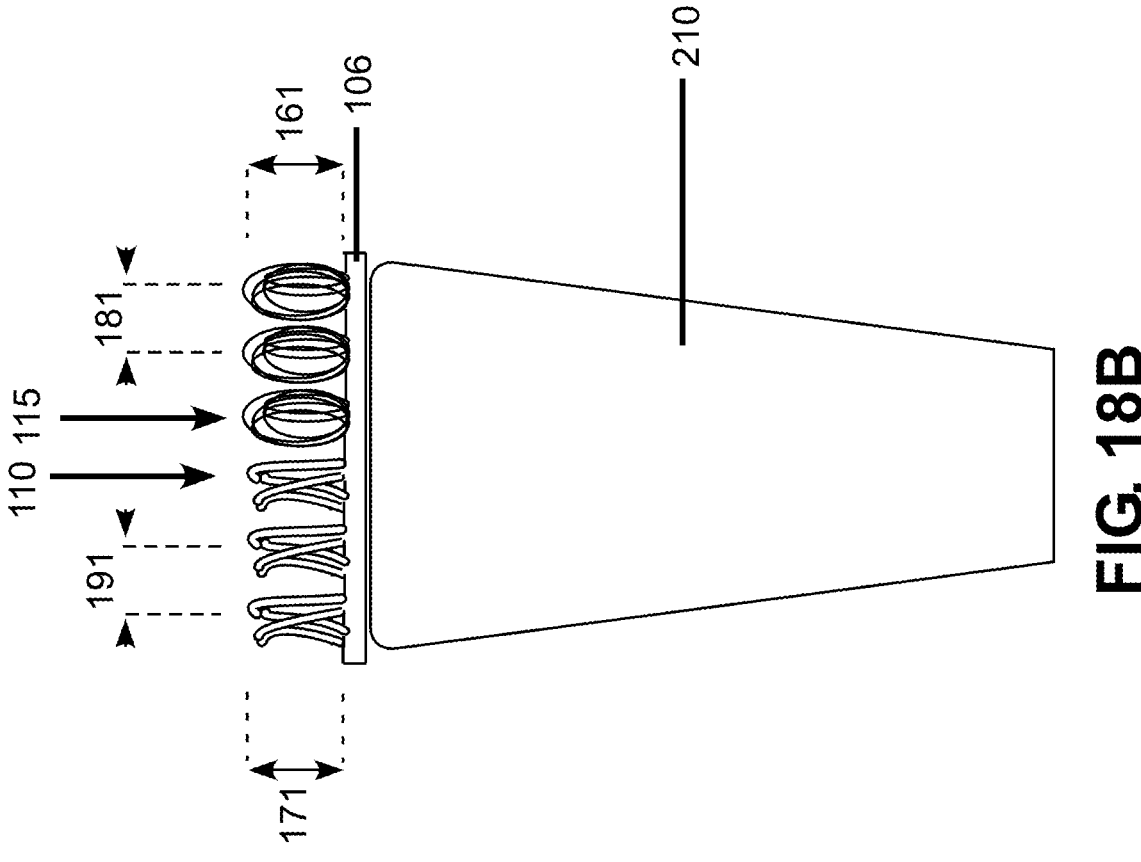
FIG. 18B is an expanded side view of a SweepBiopsy tissue sampling device (210) including a plurality of hooks and a plurality of loops, in accordance with various embodiments of the invention.
Figure 18A:
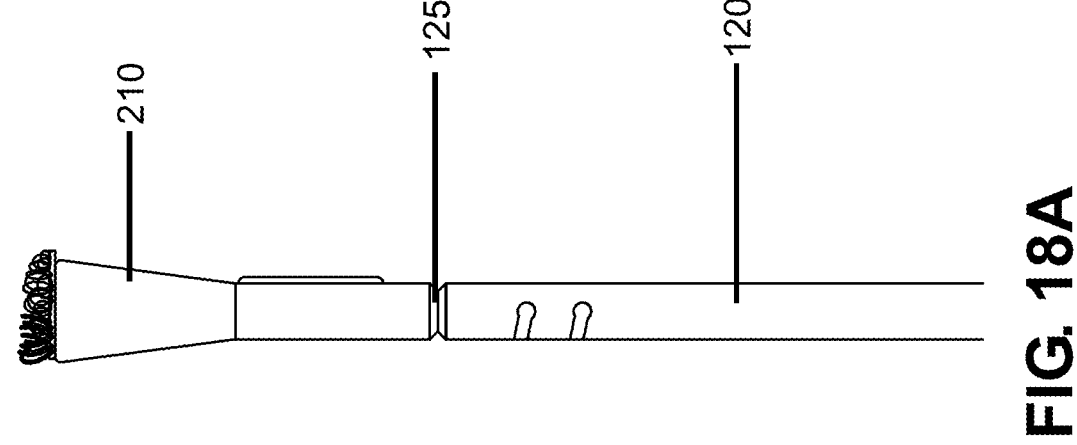
FIG. 18A is a schematic of a SweepBiopsy tissue sampling device (210) including a plurality of hooks and a plurality of loops, in accordance with various embodiments of the invention.
Figure 19B:
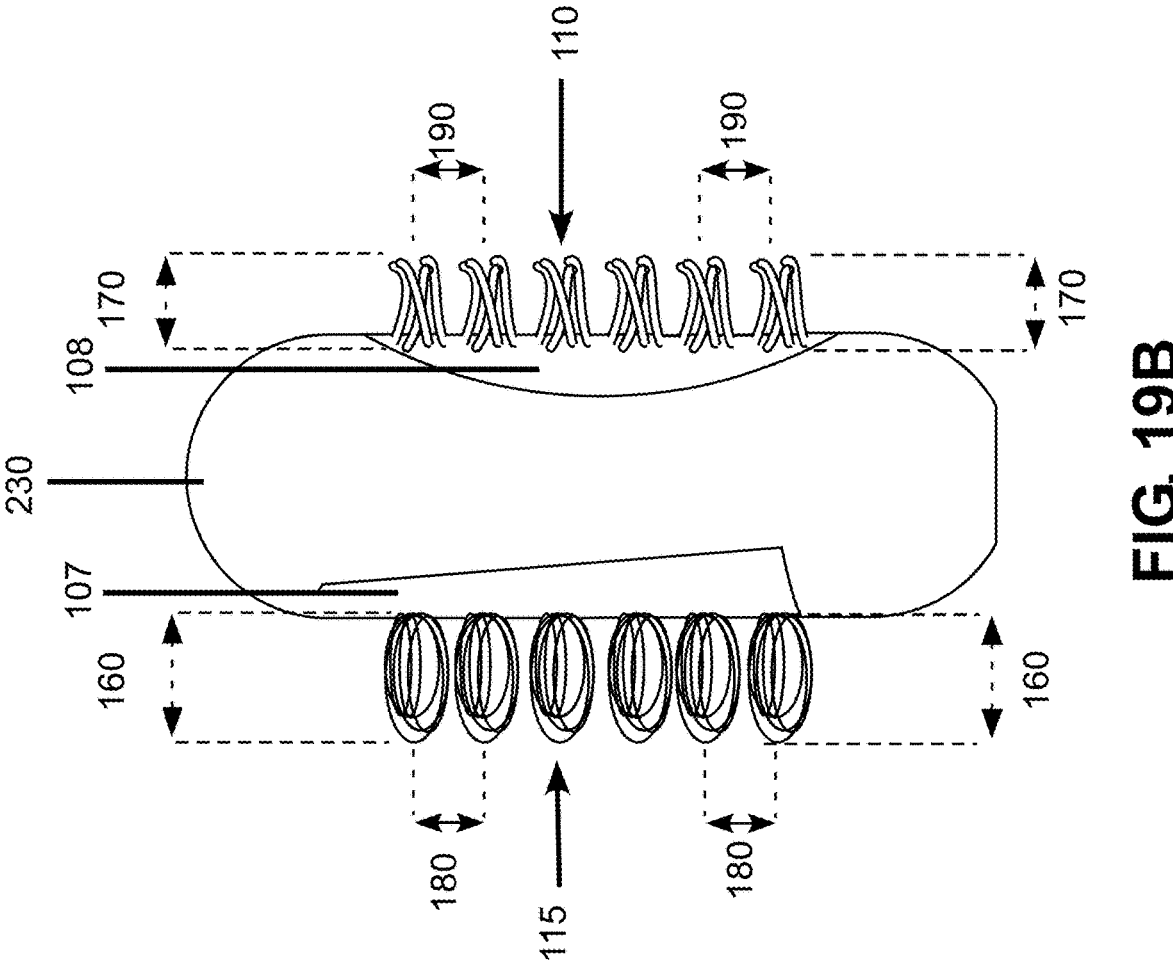
FIG. 19B is an expanded side view of a K swab oral sampling device (230) including a plurality of hooks and a plurality of loops, in accordance with various embodiments of the invention.
Figure 19A:
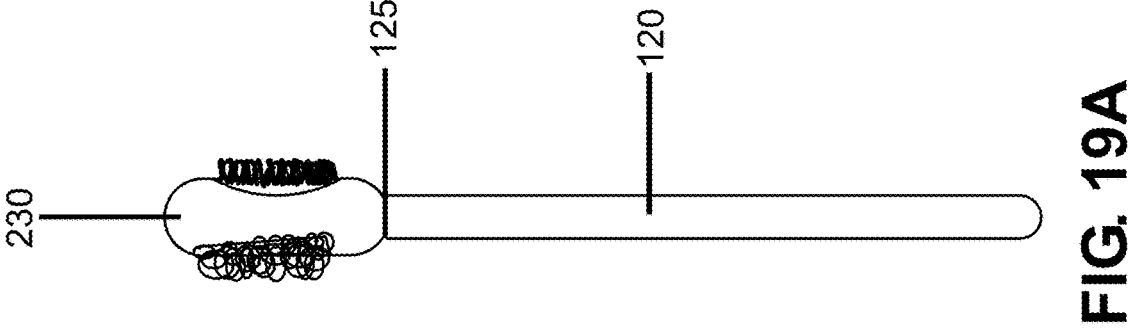
FIG. 19A is a schematic of a K swab oral sampling device (230) including a plurality of hooks and a plurality of loops, in accordance with various embodiments of the invention.

FIG. 18A is a schematic of a SweepBiopsy tissue sampling device including an abrasive material and a collector material. FIG. 18B is an expanded side view of a SweepBiopsy tissue sampling device (210) including a (210) including an abrasive material 110 (made up of a plurality of hooks of length 171 and spacing 191) and a collector material 115 (made up of a plurality of loops of length 161 and spacing 181) attached to material 106. FIG. 19A is a schematic of a K swab oral sampling device (230) including an abrasive material and a collector material. FIG. 19B is an expanded side view of a K swab oral sampling device (230) including an abrasive material 110 (made up of a plurality of hooks of length 170 and spacing 190) attached to material 108 and a collector material 115 (made up of a plurality of loops of length 160 and spacing 180) attached to material 107. In an unexpected result, the utilization of both an abrasive material e.g., a plurality of hooks and a collector material i.e., an array of loops can result in a more consistent and reliable sampling method and apparatus. The utilization of an abrasive material e.g., hooks including fenestrated loops can dislodge tissue and entrap large tissue fragments. In an embodiment of the invention, the utilization of a collector material i.e., an array of loops can entrap both large and small tissue fragments. In an embodiment of the invention, the utilization of hooks and loops enables the large histogical biopsy material isolated by the abrasive material hooks and enables the further/additional smaller histogical biopsy material retrieved by the collecter material loops to be trapped.

Figure 20:
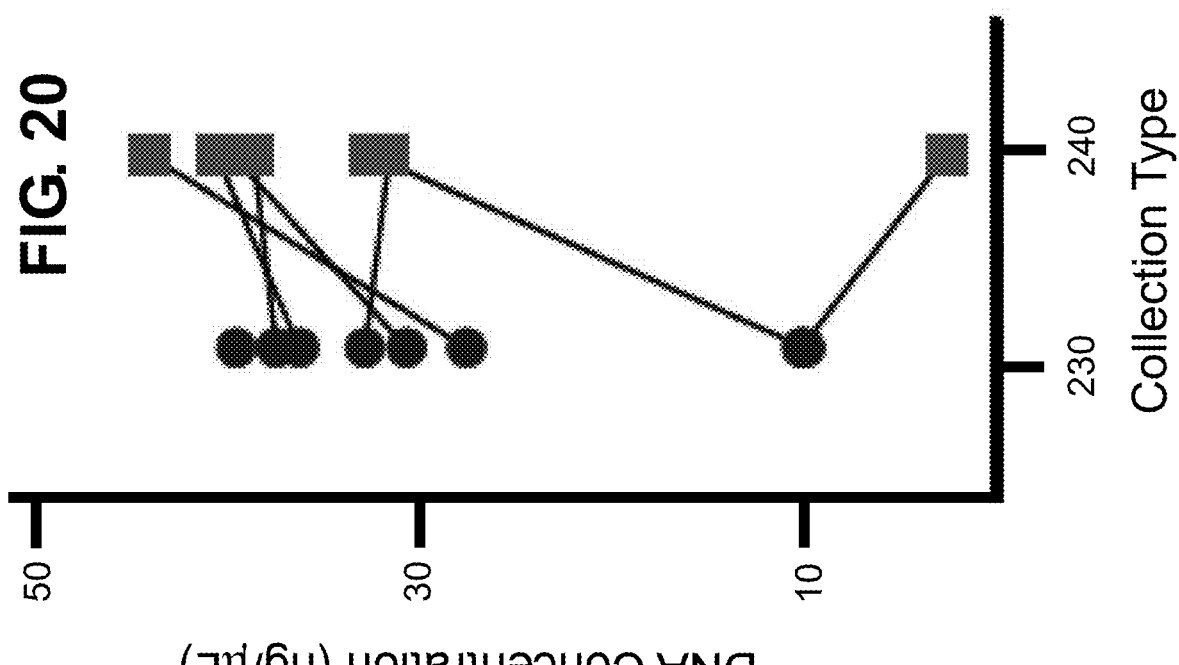
FIG. 20 is a plot of DNA concentration (ng/μL) versus collection devices (a K swab oral sampling device applied to cheek in accordance with an embodiment of the invention (230), and a Sponge based standard cheek swab collection device applied to cheek (240))
Figure 21:
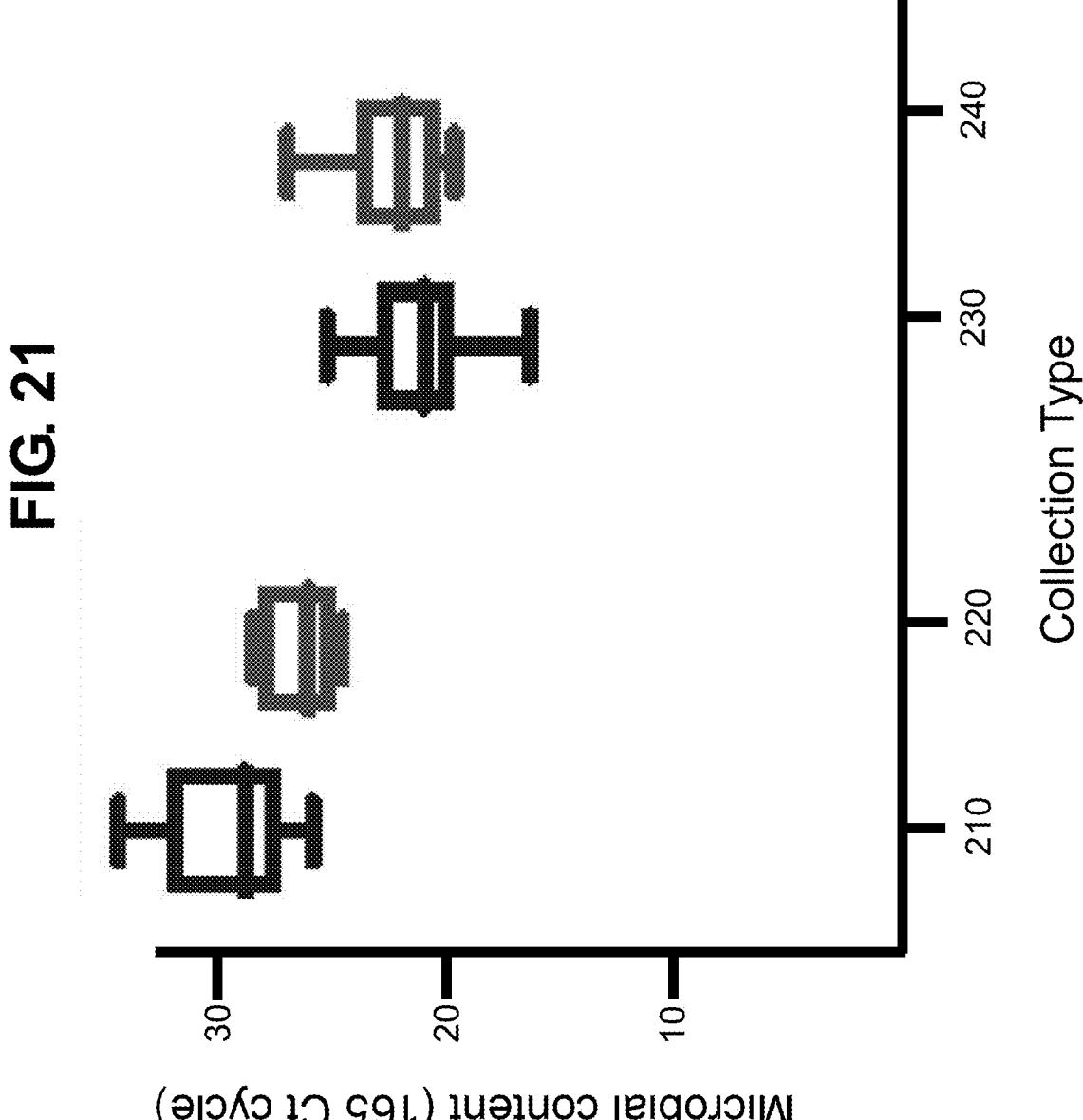
FIG. 21 is a plot of microbial content (16S cycle threshold) versus collection devices (a SweepBiopsy tissue sampling device applied to skin (elbow) in accordance with an embodiment of the invention (210), a Flock based skin standard swap collection device (220) applied to skin (elbow), a K swab oral sampling device applied to cheek in accordance with an embodiment of the invention (230), and a Sponge based standard swap collection device applied to cheek (240))
Figure 22:
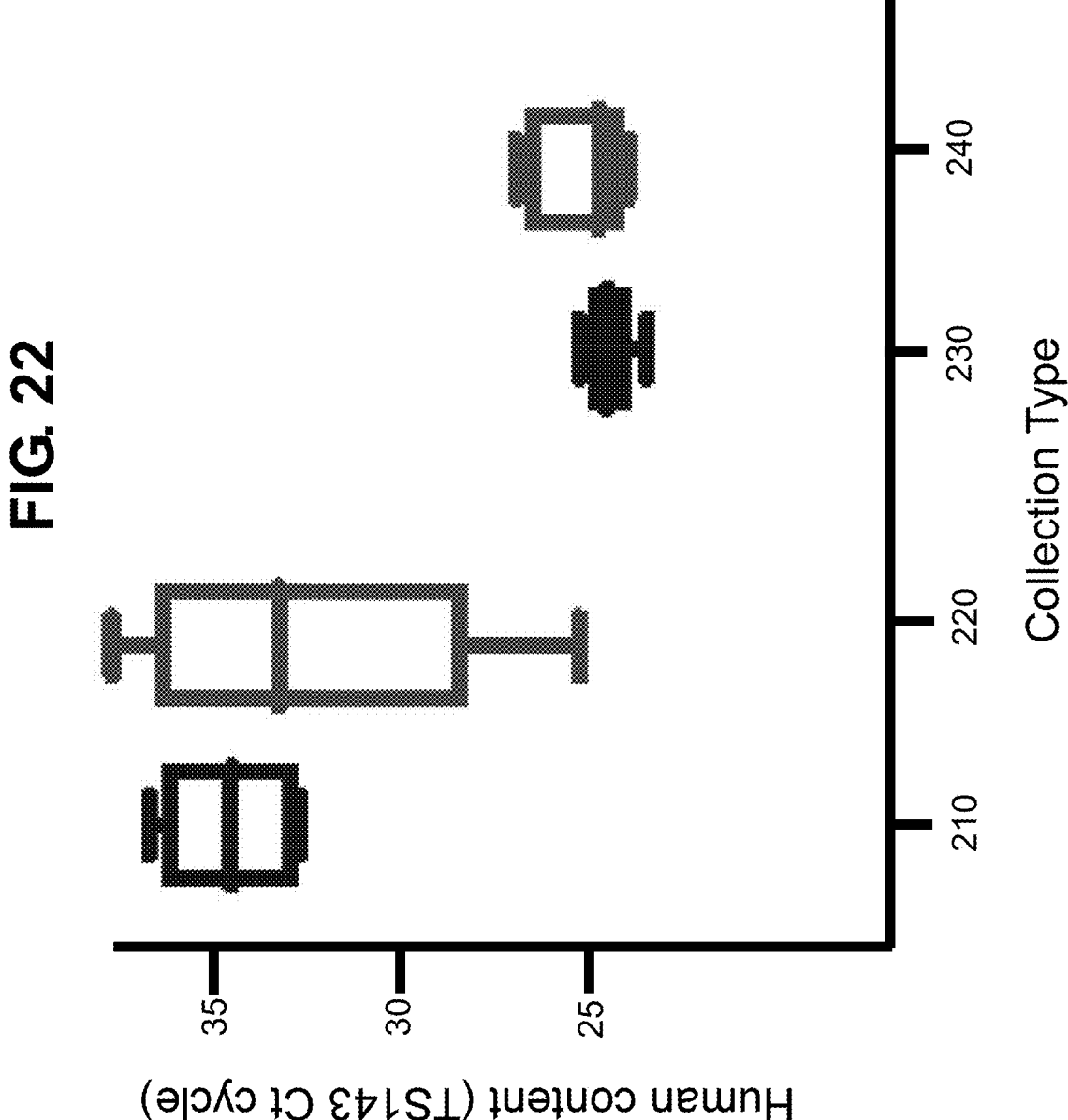
FIG. 22 is a plot of human content (TS143 cycle threshold) versus collection devices (a SweepBiopsy tissue sampling device applied to skin (elbow) in accordance with an embodiment of the invention (210), a Flock based skin standard swap collection device (220) applied to skin (elbow), a K swab oral sampling device applied to cheek in accordance with an embodiment of the invention (230), and a Sponge based standard swap collection device applied to cheek (240)).

FIG. 20 is a plot of DNA concentration (ng/μL) versus collection devices (a K swab oral sampling device applied to cheek (230), and a Sponge based standard cheek swap collection device applied to cheek (240). FIG. 21 is a plot of microbial content (16S cycle threshold) versus collection devices (a SweepBiopsy tissue sampling device applied to skin (elbow) (210), a Flock based skin standard swap collection device (220) applied to skin (elbow), a K swab oral sampling device applied to cheek (230), and a Sponge based standard swap collection device applied to cheek (240)). FIG. 22 is a plot of human content (TS143 cycle threshold) versus collection devices (a SweepBiopsy tissue sampling device applied to skin (elbow) (210), a Flock based skin standard swap collection device (220) applied to skin (elbow), a K swab oral sampling device applied to cheek (230), and a Sponge based standard swap collection device applied to cheek (240). Equal volumes of eluted material were used for all devices for qPCR input. Although there was a slight advantage in yields for the Flock based skin (220) and the Sponge based standard swap collection (240) collection devices, the SweepBiopsy tissue sampling device (210) and the K swab oral sampling device (230) consistently recovered more amplifiable material.

Further Embodiments contemplated herein include Embodiments P1-P20, S1-S25 and T1-T12 following.

Embodiment P1. A FTSC device for obtaining a histological sample from an epithelial layer including a first paddle with a first side and a second side, a second paddle, where the second paddle is smooth, a connector with a main axis of rotation, adapted to connect the first paddle at a first position to the second paddle at a second position, where a rotation of the connector around the main axis of rotation rotates the first position of the first paddle to the second position of the second paddle.

Embodiment P2. The FTSC device of embodiment P1, where the abrasive material is selected from the group consisting of a steel wool gauze, steel wool pad, metal mesh scouring pad, plastic mesh scouring pad, VELCRO® hooks, KYLON®, glass fiber, cat gut, rayon hooks, nylon hooks, fenestrated wire loops, radial DREMEL® brush, bristle brush, loofah, sterile pads, cotton swab with salt, and shark skin.

Embodiment P3. The FTSC device of embodiment P1, where the abrasive material comprises a plurality of fenestrated loops.

Embodiment P4. The FTSC device of embodiment P1, where an orientation and a spacing of the plurality of fenestrated loops are adapted to abrade the epithelial layer to dislodge the histological sample.

Embodiment P5. The FTSC device of embodiment P1, where the rotation is between a lower limit of approximately one hundred (100) degrees and an upper limit of approximately two hundred and fifty (250) degrees.

Embodiment P6. The FTSC device of embodiment P1, where the rotation is approximately one hundred and eight (180) degrees.

Embodiment P7. A FTSC device for obtaining a histological sample from an epithelial layer including a first paddle with a first side and a second side, a second paddle with a third side and a fourth side, where the third side is smooth, where the fourth side is smooth, a connector with a main axis of rotation, adapted to connect the first paddle at a first position to the second paddle at a second position, where a rotation of the connector around the main axis of rotation rotates the first position of the first paddle to the second position of the second paddle.

Embodiment P8. The FTSC device of embodiment P7, where the collector material is selected from the group consisting of dry sponges, wool, plastic, cotton, cloth, fabric, tissue, hair, paper, paper towels, felt, monofilament cloth, poly filament cloth, loops woven perpendicular to cloth material, and VELCRO® loop material.

Embodiment P9. The FTSC device of embodiment P7, where the collector material is an absorbent.

Embodiment P10. The FTSC device of embodiment P7, where the rotation is between a lower limit of approximately one hundred (100) degrees and an upper limit of approximately two hundred and fifty (250) degrees.

Embodiment P11. The FTSC device of embodiment P7, where the rotation is approximately one hundred and eight (180) degrees.

Embodiment P12. A FTSC device for obtaining a histological sample from an epithelial layer including a first paddle with a first side and a second side, a second paddle with a third side and a fourth side, where the third side is smooth, where the fourth side is smooth, a connector with a main axis of rotation, adapted to connect the first paddle at a first position to the second paddle at a second position, where a rotation of the connector around the main axis of rotation rotates the first position of the first paddle to the second position of the second paddle, an abrasive material associated with the first side, where the abrasive material is adapted to abrade the epithelial layer to dislodge the sample and a collector material associated with the second side, where the collector material is adapted to collect the sample dislodged by the first side of the first paddle.

Embodiment P13. The FTSC device of embodiment P12, where the collector material is selected from the group consisting of dry sponges, wool, plastic, cotton, cloth, fabric, tissue, hair, paper, paper towels, felt, monofilament cloth, poly filament cloth, loops woven perpendicular to cloth material, and VELCRO® loop material.

Embodiment P14. The FTSC device of embodiment P12, where the collector material is an absorbent.

Embodiment P15. The FTSC device of embodiment P12, where the abrasive material is selected from the group consisting of a steel wool gauze, steel wool pad, metal mesh scouring pad, plastic mesh scouring pad, VELCRO® hooks, KYLON®, glass fiber, cat gut, rayon hooks, nylon hooks, fenestrated wire loops, radial DREMEL® brush, bristle brush, loofah, sterile pads, cotton swab with salt, and shark skin.

Embodiment P16. The FTSC device of embodiment P12, where the abrasive material comprises a plurality of fenestrated loops.

Embodiment P17. The FTSC device of embodiment P12, where an orientation and a spacing of the plurality of fenestrated loops are adapted to abrade the epithelial layer to dislodge the sample.

Embodiment P18. The FTSC device of embodiment P12, further including an antimicrobial agent associated with one or more of the first paddle, the second paddle, the abrasive material and the collector material.

Embodiment P19. The FTSC device of embodiment P12, where the abrasive material is separated from the collector material by a distance between a lower limit of approximately $10^{-5}$ meter and an upper limit of approximately $10^{-2}$ meter. In this range, approximately means plus or minus twenty percent (20%). In an alternative embodiment of the invention the abrasive material is separated from the collector material by a distance between a lower limit of approximately $10^4$ meter and an upper limit of approximately $10^{-3}$ meter. In this range, approximately means plus or minus twenty percent (20%).

Embodiment P20. The FTSC device of embodiment P12, where the first paddle is adapted to immerse one or both the collector material and the abrasive material in a preserving solution.

Embodiment S1. A FTSC device for obtaining a sample from an epithelial layer including a paddle with a main axis including a first side and a second side, where rotation of the paddle around the main axis rotates the first side away from a user and brings the second side towards the user, an abrasive material associated with the first side, where the abrasive material is adapted to abrade the epithelial layer to dislodge the histological sample, and a collector material associated with the second side, where the collector material is adapted to collect the histological sample dislodged by the first side of the paddle.

Embodiment S2. The FTSC device of embodiment S1, where the collector material is an absorbent.

Embodiment S3. The FTSC device of embodiment S1, where the abrasive material is selected from the group consisting of a steel wool gauze, steel wool pad, metal mesh scouring pad, plastic mesh scouring pad, VELCRO® hooks, KYLON®, glass fiber, cat gut, rayon hooks, nylon hooks, fenestrated wire loops, radial DREMEL® brush, bristle brush, loofah, sterile pads, cotton swab with salt, and shark skin.

Embodiment S4. The FTSC device of embodiment S1, where the FTSC device is adapted to immerse one or both the collector material and the abrasive material in a preserving solution.

Embodiment S5. The FTSC device of embodiment S1, where the abrasive material comprises a plurality of fenestrated loops.

Embodiment S6. The FTSC device of embodiment S1, where one or more of the paddle, the abrasive material and the collector material comprise an antimicrobial agent.

Embodiment S7. The FTSC device of embodiment S1, where one or both the first side and the second side contains both the abrasive material and the collector material.

Embodiment S8. The FTSC device of embodiment S1, where the abrasive material is separated from the collector material by a distance d, where d is between a lower limit of approximately $10^{-5}$ meter, and an upper limit of approximately $10^{-2}$ meter. In this range, approximately means plus or minus twenty percent (20%).

Embodiment S9. A method of obtaining a sample from a FTSC device including receiving a FTSC device including a paddle with a main axis including a first side and a second side, where rotation of the paddle around the main axis rotates the first side away from a user and brings the second side towards the user, an abrasive material associated with the first side, where the abrasive material is adapted to abrade the epithelial layer to dislodge the histological sample, and a collector material associated with the second side, where the collector material is adapted to collect the histological sample dislodged by the first side of the paddle, the method including applying the FTSC device to an epithelial surface, rotating the FTSC device a plurality of rotations around the main axis, and obtaining the histological sample from the collector material.

Embodiment S10. The FTSC device of embodiment S9, where the sample is a histological sample, further including placing one or both the histological sample and the collector material in a preservative solution.

Embodiment S11. The FTSC device of embodiment S9, where the solution is formalin free.

Embodiment S12. The FTSC device of embodiment S9, where the preservative solution is maintained at ambient temperature.

Embodiment S13. A device for obtaining a cell and biopsy tissue sample including a finger cot including two or more patches, where a first patch is located on a distal palmar aspect of the finger cot and a second patch, an abrasive attached to the first patch, and a collector attached to the second patch.

Embodiment S14. The device of embodiment S13, where the collector is an absorbent.

Embodiment S15. The device of embodiment S13, where the abrasive material is selected from the group consisting of a brillo pad, fine steel wool pad gauze, Velcro hooks, Kylon, steel wool, glass fiber, cat tongue, rayon hooks, nylon hooks, wire fenestrated loops, plastic helix, radial Dremel brush, bristle brush, loofah, sterile pads, cotton swab with salt, and shark skin.

Embodiment S16. The FTSC device of embodiment S9, adapted to immerse one or both the first patch and the second patch in a preserving solution.

Embodiment S17. The FTSC device of embodiment S9, where the abrasive is arranged in a plurality of fenestrated loops.

Embodiment S18. The FTSC device of embodiment S9, where the second patch is located on a dorsal aspect of the finger cot.

Embodiment S19. The FTSC device of embodiment S9, where the first patch is separated from the second patch.

Embodiment S20. The FTSC device of embodiment S9, where one or more of the finger cot, the first patch and the second patch comprise an antimicrobial agent.

Embodiment S21. A FTSC device for obtaining a histological sample from an epithelial layer including a propeller with a nose cone, a main axis, a first blade, and at least a second blade, an abrasive material including a plurality of fibers associated with the first blade, where the abrasive material is adapted to abrade the epithelial layer to dislodge the histological sample, where rotation of the propeller around the main axis rotates the abrasive material, and a collector material including a plurality of loops associated with the second blade, where rotation of the propeller around the main axis rotates the collector material, where the collector material is adapted to collect the histological sample dislodged by the abrasive material, where contacting the propeller with the epithelial layer and rotation of the propeller moves the abrasive material and the collector material over the epithelial layer thereby obtaining the histological sample from the epithelial layer.

Embodiment S22. A FTSC device for obtaining a sample from an epithelial layer including a paddle with a main axis including a first side and a second side, where rotation of the paddle around the main axis rotates the first side away from a user and brings the second side towards the user, an abrasive material including a plurality of fibers associated with the first side, where the abrasive material is adapted to abrade the epithelial layer to dislodge the histological sample, where the abrasive material is adapted to entrap the histological sample which lodge between the plurality of fibers, and a collector material associated with the second side, where the collector material is not the abrasive material, where the collector material is adapted to collect the histological sample dislodged by the abrasive material which are not entrapped by the abrasive material.

Embodiment S23. A method of obtaining a sample from a FTSC device including receiving a FTSC device including a paddle with a main axis including a first side and a second side, where rotation of the paddle around the main axis rotates the first side away from a user and brings the second side towards the user, an abrasive material including a plurality of fibers associated with the first side, where the abrasive material is adapted to abrade the epithelial layer to dislodge the histological sample, where the abrasive material is adapted to entrap the histological sample which lodge between the plurality of fibers, and a collector material associated with the second side, where the collector material is not the abrasive material, where the collector material is adapted to collect the histological sample dislodged by the abrasive material which are not entrapped by the abrasive material, the method including applying the FTSC device to an epithelial surface, rotating the FTSC device a plurality of rotations around the main axis, and obtaining the histological sample from the collector material.

Embodiment S24. A device for obtaining a cell and biopsy tissue sample including a finger cot including two or more patches, where a first patch is located on a distal palmar aspect of the finger cot and a second patch, an abrasive including a plurality of fibers attached to the first patch, where the abrasive material is adapted to abrade the epithelial layer to dislodge the histological sample, where the abrasive material is adapted to entrap a histological sample which lodge between the plurality of fibers, and a collector attached to the second patch, where the collector material is not the abrasive material, where the collector material is adapted to collect the histological sample dislodged by the abrasive material which are not entrapped by the abrasive material.

Embodiment S25. A FTSC device for collecting a histological sample from an epithelial layer including a handle with a main axis, a platform at a distal end of the handle, an abrasive material comprising a plurality of fibers associated with the distal end of the platform, where the abrasive material is adapted to abrade the epithelial layer to dislodge the histological sample, and a collector material comprising a plurality of loops associated with the distal end of the platform, where contacting the platform with the epithelial layer and rotation of the handle moves the abrasive material and the collector material over the epithelial layer, where the collector material is adapted to collect the histological sample dislodged by the abrasive material thereby collecting the histological sample from the epithelial layer.

Embodiment T1. A FTSC device for collecting a histological sample from an epithelial layer including a paddle with a circumference, a first included angle, a second included angle, and a main axis, where the first included angle delineates a first portion of the circumference, where the second included angle delineates a second portion of the circumference, an abrasive material comprising a plurality of fibers associated with the first portion, where the abrasive material is adapted to abrade the epithelial layer to dislodge the histological sample, where rotation of the paddle around the main axis rotates the abrasive material, and a collector material comprising a plurality of loops associated with the second portion, where rotation of the paddle around the main axis rotates the collector material, where the collector material is adapted to collect the histological sample dislodged by the abrasive material, where contacting the paddle with the epithelial layer and rotation of the paddle moves the abrasive material and the collector material over the epithelial layer thereby obtaining the histological sample from the epithelial layer.

Embodiment T2. The FTSC device of embodiment T1, where the collector material is an absorbent.

Embodiment T3. The FTSC device of embodiment T1, where the abrasive material is selected from the group consisting of a brillo pad, fine steel wool pad gauze, Velcro hooks, Kylon, steel wool, glass fiber, cat tongue, rayon fenestrated hooks, nylon fenestrated hooks, wire fenestrated loops, plastic helix, radial Dremel brush, bristle brush, loofah, sterile pads, cotton swab with salt, and shark skin.

Embodiment T4. The FTSC device of embodiment T1, where the paddle is adapted to immerse one or both the collector material and the abrasive material in a preserving solution.

Embodiment T5. The FTSC device of embodiment T1, where the plurality of fibers comprise a plurality of fenestrated loops.

Embodiment T6. The FTSC device of embodiment T1, where one or more of the paddle, the abrasive material and the collector material comprise an antimicrobial agent.

Embodiment T7. The FTSC device of embodiment T1, where one or both the first side and the second side contains both the abrasive material and the collector material.

Embodiment T8. The FTSC device of embodiment T7, where the abrasive material is separated from the collector material by a distance d, where d is between a lower limit of approximately $10^{-5}$ meter, an upper limit of approximately $10^{-2}$ meter. In this range, approximately means plus or minus twenty percent (20%).

Embodiment T9. A method of obtaining a histological sample from a FTSC device including receiving the FTSC device including a paddle with a circumference, a first included angle, a second included angle, and a main axis, where the first included angle delineates a first portion of the circumference, where the second included angle delineates a second portion of the circumference, an abrasive material comprising a plurality of fibers associated with the first portion, where the abrasive material is adapted to abrade an epithelial layer to dislodge the histological sample, where rotation of the paddle around the main axis rotates the abrasive material, and a collector material comprising a plurality of loops associated with the second portion, where rotation of the paddle around the main axis rotates the collector material, contacting the FTSC device to an epithelial surface, rotating the FTSC device around the main axis, where the abrasive material dislodges the histological sample from the epithelial surface, and collecting the histological sample in at least the collector material.

Embodiment T10. The method of embodiment T9, further comprising placing one or more of the histological sample, the abrasive material and the collector material in a preservative solution.

Embodiment T11. The method of embodiment T10, where the preservative solution is formalin free.

Embodiment T12. The method of embodiment T10, where the preservative solution is maintained at ambient temperature.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A method of collecting a tissue sample from a dry skin using a Frictional Tissue Sampling and Collection (FTSC) device comprising:

(a) receiving a FTSC device comprising:

(i) a platform associated with a palmar aspect of a finger region comprising a proximal region, a gap and a distal region, where the proximal region and the distal region are adjacent, where the proximal region is proximal to a middle phalanx, where the distal region is distal to the middle phalanx;

(ii) an abrasive material comprising a plurality of fibers associated with the platform, where the abrasive material is associated with the distal region, where the abrasive material is adapted to abrade an epithelial layer to dislodge the tissue sample from the dry skin; and (iii) a collector material comprising a plurality of loops associated with the platform, where the collector material is not a fenestrated loop, where the collector material is associated with the proximal region, where contacting the dry skin with the platform and rotation of the platform moves initially the abrasive material and subsequently the collector material over the dry skin, where the collector material is adapted to collect the tissue sample from the dry skin that is dislodged by the abrasive material and that falls between the plurality of fibers of the abrasive material or are otherwise not collected by the abrasive material;

(b) contacting the FTSC device to the dry skin;

(c) rotating the FTSC device, where the abrasive material is adapted to dislodge the tissue sample from the dry skin; and (d) collecting the tissue sample in at least the collector material.

2. The method according to claim 1, further comprising placing one or more of the tissue sample, the abrasive material and the collector material in a preservative solution.

3. The method according to claim 1, where the abrasive material does not contact the collector material.

4. The method according to claim 1, where the tissue sample comprises exfoliated cells and diseased tissue.

5. The method according to claim 1, where the platform is a finger cot adapted to be supported on a gloved finger.

6. The method according to claim 1, where the abrasive material is selected from the group consisting of a fine steel wool pad gauze, hooks from a hook and loop fastener, steel wool, glass fiber, cat tongue, rayon fenestrated hooks, nylon fenestrated hooks, wire fenestrated loops, a plastic helix, a radial brush, a bristle brush, loofah, a sterile pad, cotton swab with salt, and a shark skin.

7. The method according to claim 1, where the plurality of fibers comprise a plurality of fenestrated loops.

8. The method according to claim 1, where a plurality of dry skin cells are dislodged from a site, where the plurality of dislodged dry skin cells are collected in a sweep action of a loop array adjacent to a hook array.

9. The method according to claim 8, where the gap allowing collection of the plurality of dislodged dry skin cells is between:

a lower limit of approximately $10^{-5}$ meter; and an upper limit of approximately $10^{-2}$ meter.

10. The method according to claim 8, where the gap allowing collection of the plurality of dislodged dry skin cells is between:

a lower limit of approximately $10^{-5}$ meter; and an upper limit of approximately $3\times10^{-3}$ meter.

* * * * *